US007166699B2

(12) United States Patent
Zwiebel

(10) Patent No.: US 7,166,699 B2
(45) Date of Patent: Jan. 23, 2007

(54) MOSQUITO ARRESTIN 1 POLYPEPTIDES

(75) Inventor: Laurence J Zwiebel, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 398 days.

(21) Appl. No.: 10/056,405

(22) Filed: Jan. 24, 2002

(65) Prior Publication Data

US 2003/0166013 A1 Sep. 4, 2003

Related U.S. Application Data

(60) Provisional application No. 60/264,649, filed on Jan. 26, 2001.

(51) Int. Cl.
*C07K 14/00* (2006.01)
*A61K 38/16* (2006.01)
(52) U.S. Cl. .................... 530/350; 424/198.1; 514/2; 514/12; 530/324
(58) Field of Classification Search ............. 424/198.1; 514/2, 12; 530/300, 350
See application file for complete search history.

(56) References Cited

U.S. PATENT DOCUMENTS

| 5,011,909 | A | 4/1991 | Borovsky et al. |
| 5,030,722 | A | 7/1991 | Snyder et al. |
| 5,128,246 | A | 7/1992 | Snyder et al. |
| 5,130,253 | A | 7/1992 | Borovsky et al. |
| 5,439,821 | A | 8/1995 | Borovsky et al. |
| 5,501,976 | A | 3/1996 | Borovsky et al. |
| 5,629,196 | A | 5/1997 | Borovsky et al. |
| 5,670,354 | A | 9/1997 | Burns et al. |
| 5,702,916 | A | 12/1997 | Molin et al. |
| 5,993,778 | A | 11/1999 | Firestein et al. |
| 6,008,046 | A | 12/1999 | Ffrench-Constant et al. |
| 6,071,878 | A | 6/2000 | Delecluse et al. |
| 6,610,511 | B1 | 8/2003 | Carlson ................ 435/69 |
| 2002/0064817 | A1 | 5/2002 | Buck et al. |
| 2003/0045472 | A1 | 3/2003 | Axel et al. |
| 2003/0143679 | A1 | 7/2003 | Vosshall et al. |
| 2003/0186359 | A1 | 10/2003 | Vosshall et al. |
| 2004/0003419 | A1 | 1/2004 | Carlson ................ 800/8 |

OTHER PUBLICATIONS

Pierce et al. (2001). Classical and new roles of B-arrestins in the regulation of G-protein-coupled receptors. Nature Reviews. 2:727-733.*
Fukuto et al. (2004). G protein-coupled receptor kinase function is essential for chemosensation in C. elegans. Neuron 42:581-593.*
Dolph, P.J. (2002). Arrestin: roles in the life and death of retinal neurons. The Neuroscientist 8(4):347-355.*
McDonald et al. (2000). B-arrestin 2: a receptor-regulated MAPK scaffold for the activation of JNK3. Science 290:1574-1577.*

Gurevich et al. (1995). Visual arrestin binding to rhodopsin. The Journal of Biological Chemistry. 270(11):6010-6016.*
Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Problem and Tertiary Structure Prediction. Birkhauser:Boston, pp. 492-495.*
Bentrop, et al.; *An arrestin homolog of blowfly photoreceptors stimulates visual-pigment phosphorylation by activating a membrane-associated protein kinase*; Eur. J. Biochem (1993) 216: 67-73.
Boekhoff, et al.; *Termination of second messenger signaling in olfaction*; Proc. Natl. Acad. Sci.; Jan. 1992; 89: 471-474.
Clyne, et al.; *A Novel Family of Divergent Seven-Transmembrane Proteins: Candidate Odorant Receptors in Drosophila*; Neuron, Feb. 1999; vol. 22, 327-338.
Fox, et al.; *Candidate Odorant Receptors from the Malaria Vector Mosquito, Anopheles Gambiae AND evidence of Down-Regulation in Response to Blood Feeding*; PNAS, vol. 98, No. 25, Dec. 2001, 14693-14697.
Hyde, et al.; *Twenty Drosophila visual system cDNA clonse: One is a homolog of human arrestin*; Proc. Natl. Acad. Sci.; Feb. 1990; 87: 1008-1012.
Levine III, et al.; *Isolation of a Novel Visual-System-Specifc Arrestin: An In Vivo Substrate for light-Dependent Phosphorylation.*, Mechanisms of Development, Dec. 1990, 1:19-25.
Merrill, et al.; *Visual Arrestins in Olfactory Pathways of Drosophila and the Malaria Vector Mosquito Anopheles Gambiae*; PNAS, vol. 99, No. 3; Feb. 5, 2002; 1633-1638.
Raming, et al.; *Arrestin-Subtypes in Insect Antennae*; Cellular Signaling; 1993; 5: 69-80.
Roman, et al.; *Kurtz, a Novel Nonvisual Arrestin, Is an Essential Neural Gene in Drosophila*; Genetics; Jul. 2000; 155: 1281-1295.
Smith, et al.; *Isolation and structure of an arrestin gene from Drosophila*; Proc. Natl. Acad. Sci; Feb. 1990; 87: 1003-1007.
Smith, et al.; *Isolation and expression of an arrestin cDNA from the horseshoe crab lateral eye*; Journal of Neurochemistry; 1995; 64: 1-12.
Vosshall; *The Molecular Logic of Olfaction in Drosophila*; Chem. Senses (2001) 26: 207-213.
Vosshall, et al.; *A Spatial Map of Olfactory Receptor Expression in the Drosophila Antenna*; Cell, vol. 96; Mar. 5, 1999; 725-736.
Yamada, et al.; *A 49-Kilodalton Phosphoprotein in the Drosophila Photoreceptor is an Arrestin Homolog*; Science, vol. 248 (Apr. 27, 1990); 483-486.

(Continued)

*Primary Examiner*—Christine J. Saoud
*Assistant Examiner*—Jon M Lockard
(74) *Attorney, Agent, or Firm*—Wyatt, Tarrant & Combs, LLP.

(57) ABSTRACT

The invention discloses polynucleotides and polypeptides of arrestin and odorant receptors. Also disclosed are methods for producing such polypeptides and methods of making antibodies. This invention also discloses a method of identifying compounds that bind to arrestins or odorant receptors. A method of identifying compounds that inhibit the binding of mosquito arrestin to a mosquito odorant receptor is also disclosed.

2 Claims, 28 Drawing Sheets

OTHER PUBLICATIONS

Vosshall, et al.; International Publication No. WO 00/50566; International Application No. PCT/US00/04995; International Publication Date: Aug. 31, 2000; International Filing Date: Feb. 25, 2000; Title: *Genes Encoding Insect Odorant Receptors and Uses Thereof*; International Patent Classification: C12N; Published by the World Intellectual Property Organization, International Bureau.

Nighorn, et al.; *Dissecting the Molecular Mechanisms of Olfaction in a Malaria-Vector Mosquito*; PNAS, vol. 99, No. 3; Feb. 5, 2002; 1113-1114.

U.S. Appl. No. 10/094,240, filed Mar. 8, 2002, Zwiebel.

Merril et al. Molecular characterization of arrestin family members in the malaria vector mosquito, Anoopheles gambaie. Insect Molecular Biology, Dec. 2003, vol. 12, No. 6, pp. 641-650.

Xu et al. Identification of a distinct family of genes encoding atypical odorant-binding proteins in the malaria vector mosquito, Anopheles gambiae. Insect Molecular Biology. Dec. 2003, vol. 12, No. 6, pp. 549-560.

\* cited by examiner

*Anopheles gambiae* odorant receptor 1 genomic sequence (SEQ ID NO: 9)

Features:
1) Presumed Untranslated 5' and 3' regions are underlined.
2) Potential TATA box transcription initiation signal is double underlined.
3) Putative Start (ATG) and Stop (TAA) codons are in BOLD.
4) Introns are tentatively assigned and are shown in lower case.
Exons are boxed.

AGCTTTGTTCATTTATGTTGAAATCTAGCCCATTTGTATAGTGCTGAAGAAGAACATACGAAAGTACCTCGT
CCGAACACTATCAACATTAATTATACCAAGCTAGAAGAGATATTTATGTCAAGCCTCAACATCATAGGAAACTTT
AGCAAAACCATTAATTTACATGATAAGTCCCACCTCTTACCCCAGCACAGTTTGAGAAGGACGAAAGTATCT
TTACGATAATATTACTCTAAGGTAGTTTTTGAATAAAAATTACGTGCAAGTGGTGCATCGGACATCATTC
GAAAGAAATCTACTAAGTCATACACACCAAGACGACGAGTAGTTTCATCTAGAAAAAAACGGTCAGCTCCATC
GAACACGTCAGGACATAACTGCGACATGCTATGGTCAGTCCCACTAGTGCCAACACTGGTTCCAGGCACTACCTT
CCGAAGCAGTAGAACCTAATGTATTGGAAATTATTAGGACATACTGCAACATGCATATGGCTAGTTCCGCTGGTACC
AACGATGGCACCAGGACACTATCGCGGCTGAGGCTGGATTGCTTCAAAGCATTAGAAATCACTGTAAATCTATACAAAAACGGCTTTACCATACT
TTATCACAAAAACGGCAGTGAGGCTGGATTGCTTCAAAGCATTAGAAATCACTGTAAATCTATACAAAAACGCTTTACCATACT
TTAAAAGATAGACAaCAGTAGAGAACACATTAGTGCTTCTCGAGTTAGTGCCTTCAAGTAAGCGTTT
AATGCTCAATTGTTGTAGATTCGTTGGATGACTCTCGCTACGTGCTATAGTGGTCAATACTTCCAATTAGATTCAT
AATTAGTTTCCAATTGTGCCACGGAAAACCCaCAAAAGAAAAAAAACTTGTATCTAGGGTGGAATTTTTCGAGAACA
ATTGGACACTTCATATGAAAAAGGACAGCTTTTTCAAATGTTAAATAAACACCGTTGGATCCTTTgttggatttca
attctccaaattctgcagaatatctgcaatttacaaactgctcaaccaccaataatccaattcattcatcctg

```
TTTTCTGTTACGTAGGGAATGAAATCTCCTATACGgtaggttggacacgtagaggaattaaatgttgggaagaata
tcaataccaaatagtatgatgtttcgttacagACGGATAAATTACAGAGTTTGTTGGGTTTTCCAACTACTTCAAG
TTCGATAAGCGTACCAGCCAAGCAATGATATTTTTCTGCAAAgtgagatagcggtgtatttgtgcagtcagtaca
ttaaatacgttctctatttcagGACTCTTAAAGAGTTCACATCAAGGTGGAAGTGTCTTGAAGGTTACGCTAAAT
CTTCACACATTTTGCAGgtatgtaattatgctgtggtattagcttgaaataagctacaaactttgaaagtaattt
caatctgttttgtadATTATGAAGCTATCGTACTCCTATCTGGCCGTACTTCAGAGCATGAATCAGAGTAATGGtG
tTAATATCCtTAATGTTGAAATTATATTTGTTAGATTTATTGCATAAAGTAATAATTTAATCATCAAACGT
AAGCCCGCtaGTTTTCAATTAGCCTTTCCAAATTTATCAAATTGATTGCAGAGTTTCAGGAATT
TAATCTGATAGGATATCTTGTTTATCCAATAGAGGTGTGAAGCGTTCCCAAGCCATTCGTTGATAGTTTATAGCA
CCGTCGAGCAGTTGATCGCTGATGTGCTAGGCGCACATGTATAAGAGATTAGACTTTGTTACATATATAACC
CTTTCACACGTTTCACACAATATAATGCACAACGATTAGAGATGACTTCACAAAGTCCATCAGTGGTAGGAGTATAC
AAATTATGCATTTTATTCTCACGCAACAtAATGAGAAACAAAGGATACCAAGCATACCCTTTTTACTTGACAATT
TCATTTGATTTATGTAATAAAGCACTGCaCGTCGACTTCCTAAAA
```

*FIG. 1C*

*Anopheles gambiae* odorant receptor 2 genomic sequence (SEQ ID NO: 10)

Features:
1) Presumed Untranslated 5' and 3' regions are underlined.
2) Potential TATA box transcription initiation signal is double underlined.
3) Putative Start (ATG) and Stop (TAA) codons are in BOLD.
4) Introns are tentatively assigned and are shown in lower case.
5) Exons are boxed.

GGGATCCTCTAGAGTCGACCTGTGCCTTCCCTCACCGTGACGTGCTAGAAATGTTCAACATACTCGT
CCGCAGAGCGAAGAGACGAACAGCGAATGTCCCAGGAAATGTCACAGCAAGTGAACCCAAACCG
AGCTGTGCGCTTTGTGTGCGCTTAAAAATGCCCTTCCTTGCCGCATCTGCTTGGTTTCACACGCTTTCCCAGG
AAATCCACTGACCACCTGCCACACATCAACACCGGAGCGGGAGCCTCAGTGCCCAGCGAAGCATATAATTGCTCA
AAAGTCACGGTACTCAATTAATTGATTATAATCAATTTCGTGCCTTGCTCACTAACACCCTTCTTCCACAATCATCG
CCGAGTGAGCGAGTATAAAGGTGAAGAAACGTACCTTGCTCACTAACTGAACCGGATTTCAAAAGGAACA
TAAACCGCAACCGAGCCGAAATGCTGATCGAAGAGTGTCCGATAATTGGTGTGCGAGTGTGGCTGTTC
TGGTCGTATCGCGGCGCGTTGTCCGCGTTTCTGTTCGGCATGCTGCCGTGCTGAACGTTTCCA
GTTCCTGAAGCTGTACTCGTGCCGCCGAGCTGAGCGAGCTCATCATCAACGATACTTTACCGTGCTGTACTTTA
ACCTCGTGtacgtgggcgaggggaggggccaatcccactggtggatatttcataccttttcatgtgtt
ttttattctctgttgtgccatccagCTCCGAACCTCCTTTCTCGTGATCAATCGACGGAAATTGAGACATTTT
TTGAAGGCGTTGCCGCCGAGCTGAGCGAGgtaagtcattggttttctagttttggggagttgttacaAAAAATGACGACATCCGACCCGT
ccataaccaccccgacggtaacatttgatcgtcccgcgaaatgtttgtacagAAAAATGACGACATCCGACCTGCT
GCTGGAGCGTACACGGGACGCATGCTATCGATATCGAATCTGTGCCGCCCTTCATTAGTGCCGTGCT
TTGTGACCTATCCTCTGTTTGTGCTGCAGTTGCAGTTTACCTTACCTTTACCTGCTGACGATACGGCGTGACGTGCTGGCC
ACCCCGACCTACCAGTCGTGTTTGTGCTGCAGTTACCTTTACCTTCCCGCCTGCTGCATGTACATCCCGTTCAC

*FIG. 2A*

```
CAGCTTCTACGCGGACCTGCACGCTGTTTGCGCTCGTCCAGATAGCGGCCCTAAAAGCAACGGCTCGGACGCTTGGGGC
GCCACAGCGGCACGATGGCTTCGACGGACACAGCGCGGCACACTGTTCGCGGAGCTGAAGGAGTGTCTAAAGTAT
CACAAACAAATCATCCAGtaagtagacgctagtagacgcatacacaaaccgaagctcgaccggattgccctcccgggaggggagttttgct
atttcgggatgcgcagcacgcatacacaaaccgaagccattaattctcccgttttcatgcccgcacggcact
gggtcatgtttcacatccttccttctctgtctccaaacacacacacgcgcgtgcacgtacagATATGTTCATGATCTC
AACTCACTCGTCACCCATCTGTCTCTGGAGTTCCTGTCTTCCGGAGTTCCTGTCTCTGCGCCACTCTGTTTCTGCT
AAGCATTGtaagtaaaatcgaccgacgtgcgtcgctagtccgtctccggactctcatttcggactcaatcgttcc
atctctcaatadAGCAATCAGCTGGCACAGATGATAATGATTGATCGTACATCTTCATGATACTCTCGCAGATGTT
TGCCTTCTATTGGCATGCGAACGAGTACTGGAGCAGGtaatgcgctgaagctgagtttggttgagcggttcgcta
tagatcggctgtcttacattgttgttttctgcatggggatcggttcctctccatttcagAGCCTAGGC
ATTGGCGATGCCATTTACAATGCGACCGATGGTGGTAAGtttggctgatcgatcgtgttcaatgacatggcacagaaggctgtgta
ACGTGCTCAGCGACCGATGGTGGTAAGtttggctgatcgatcgtgttcaatgacatggcacagaaggctgtgta
aatagctgttcattaataagtttttcagaatgtatcgtttttagttgattgaatcgcattgttctatgcaatggta
gcaacaatagaccgccttaatccaagctccttaggattgatttttatttaagaagaaagataaaccatttt
tagtaaccaattagttacagagaaccaaatacagaatttattattattattattattattattattattatta
ttattattattattattattattattattattactattattattttattattattttattattat
tattattattattattattactattattattactattattatactattattattattattattattat
attattattattattattattactattactatactattattaattattaattattaattattattatta
attattattattgttcattattgttcattattcttatcattattcttataattattttttattattgttgtt
ttattattactattctattattcttattattattatttttattattctattatcctattattattattatta
attattattactattctattattcttgttattattgttattattgctattgttattattcttattgttgtt
gttgttgttgttcttattattgttgttgttgttgttgttgttgttattattgttttttttattcctaatta
```

*Anopheles gambiae* odorant receptor 3 genomic sequence (SEQ ID NO: 11)

Features:
1) Presumed Untranslated 5' and 3' regions are underlined.
2) Putative Start (ATG) and Stop (TAA) codons are in BOLD.
3) Introns are tentatively assigned and are shown in lower case.
4) Exons are boxed.

AAGCAGAACACATCAAGAGAAGCAATTAGGTTGTCGTAGCAAGTAGTTCGGAGGAGGAATAAAATACATGCC
TTCTGAGCGGCTTCGTCTCATTACTTCCTTCGGAACTCCTCAAGACAAACGCACGATGGTACTGCCAAATTAAAGG
ATGAAACAGCAGTGATGCCGTTTCTGCTGCAAATTCAAACCATTGCCGGACAAACGTGGGGTGACCGTTCCCAGCGGTAC
CGTTTTATCTCATCTTTCTGCTACTTCTGCGCAGGCCGATGGTGGTTCTACCAAAGTGCTGTTCGGTTATCCAGATCTCGA
GGTTGCGGTACCGCGGCACGCGGCCGAGCTGCATGTTCGAATGGAATCGAACGCATTCTTCGGCATGCTAATGTTTTCCTTTCAAC
GCGACAACTACGAGGATTGGTGCATCAGCTGCAGGATCTGCAGCTCTAGgtgagtatgcagccaatcgattgttc
caaacccttcgcaacatccttcgtaacactgctacactttcagTCCTCCAAGACCTACCCACAGAGCTGGGAGAGTAC
CTGATCTCAGTGAACCGACGGGTCGATGGTTCTCCAAAATTACTTCTGCTGTCACTTTTCATGGCAACGTTCTT
TTGGTTCATGCCCCGTCTGGACGCTATTCGGACTGTACTTCCTGAACATTCGGACTTCGATGGCGCACTATACGTTTATGTGGCCATTATG
TGCACCTCGAGGAAGAGCTGTACTTCCTGGGTTTACCGGTTGGCACAAAGCTCGTGACCATTTTCAGCAATGTTAAGTACTGTTC
TGGCCCACGATCTATACGCTCGTTGCAATCCGAATCCACTGTCTAGCGAGAGTAGCCGCCAAGACCGAGCGGAAAAGGAGCTGA
GGCCATGTCGAAGCTCGTTGCAATCCGAATCCACTGTCTAGCGAGAGTAGCCGCCAAGACCGAGCGGAAAAGGAGCTGA
ACGAGATTATTTCCATGCATCAGCGGGTACTCAAgtaagtaaattcaaattgaaagtttttgcagggaataacttgag
tgtgtctgaccgtgcacatcctagCTGCGTGTTCCTGCTGGAGACGACATTCCGCTGGGTATTTTTGCGAGTTC
ATTCAGTGTACAATGATCTGGTGCAGTCTCATCCTCTACATAGCGGTGACGgtaatagcatttttcgtcattcgtta
GcttattcaatccattttttgtgaacgtgaattcccccagGGGTTCAGTCTCGACGGTAGCGAGTCGAATGTATGTGTCCAG
ATCATTTTGGTGACGGTGGAACTTACGGCTACTTCGAACAGATCTAACCACGGAGTGCTTTGgtacc

```
ctttggatgaagcttcaaaagtaattccaaattctgtttcgattttccccttttccactagAGCTATGGCGTTG
CCCTCGCCATTTACGATAGCGAGTGGTACAAGTTTCCATTCGATGCGCCGCAAACTTCGACTGCTACTGCAACGA
TCCCAAAAACCGCTCGGCGTAACGGCGGAAAGTTTCGCTTCGTCAATGTGGCCCAGTTTGGCAAGtaacattaat
tacagtttgaaaattctgaagaatgcatcttacttgccttactgttgttccagATGCTCAAGATGTCCTATTCATT
TTACGTAGTACTGAAGGAGCAGTTTAGGAGCTGCTGTTTCCCACCCTGACGCACTGAGCTATTTTCGCACTGTCTTCTGT
TTGTTGGACGCAGCAGGTACAATTTTGCTGTGTTATTACGGCAGCTTTTTCCaCAATAAACACACAATAACGTACGACAG
ACAGCTGAAGGACAGGGTACAATTTTGCTGTGTTATTACGGCAGCTTTTTCCaCAATAAACACACAATAACGTACGACAG
TTCTACGATTTAGCGTTTATTTACTGTAGGATAGAGAAACGGGAGAAGCCCGGCCAGCAGTAAACAACGAAAGGGGCCACCG
TATTCTTTTCATTGTAGGATAGAGAAACGGGAGAAGCCCGGCCAGCAGTAAACAACAAAACCGGCGAACAACAAACGGTGCCGAA
GGGGAAAAACACGGGAGCAAAACGGGAGAAGCCCGGCCAGCAGTAAACAACAAAACCGGCGAACAACAAACGGTGCCGAA
ACGA
```

*FIG. 3B*

*Anopheles gambiae* odorant receptor 4 genomic sequence (SEQ ID NO: 12)

Features:
1) Putative Start (ATG) and Stop (TAA) codons are in BOLD.
2) Introns are tentatively assigned and are shown in lower case.

GGGGAACTCCCCACCCGACCAGACGACGAGACGGAAAGCTAACGATGTGCAATTGAATAGTCATTAGT
AGCGTTTTTGCTCGCAAACGAACTAACCCTTTGACTTTTTAAGTTCACTACGGTGAGGACAAAAA
TCAATAAATAAATCGAGACCGTTGATGAGCAAAAAGAAAAAAAATATTTACTGATTTTCATTT
CGTTCCATCGACTACATAATTCATATAGCCACATTTTATTTATAAGTTTTTGTATCATTTTTA
AACAACACAAAATGCATCCTTTCGAATATTAGTCAGGTTGTATCAACAATGAAGTTTGAACTGT
TTCAAAATATTCCTCCCGACACGGTCTTATCCTTCGTGTCGTAAGGCTTTTGCATATCGTGGGC
ATGAATGGGGGCAGGATTTCGGTCGCGAATTGGAGTTGGTGCCACGATGGTCACCACGAGTGTG
TCTTGTAATACCGCCACTAACGGGGGCTAAATATTACGGCGCAGTATGTTCTTGCCTACGATGTGCCACTTT
GAATTCCTGTTTAATGCAATATTACGGCGCAGTATGTTCTTTGCCTACGATGTGCCACTTT
CCAAGCGTTCATCCAGGAACTGAAGAGACCCTTTCGGTTTTGGgtaatatttaattaattaaattgcgttattgcat
catcatttgttctctttgcagTATGCTCACATTCCTACAGACTAAAGTATAAGCTGACCCGGTTCAACCGTC
GAGCGGATATTATCGCCAAAGTGCAAACGACCTGCATGGGTGCTGTAAGCTTTCTACTGGAT
TGCACCGATACCTTCCATCTGTGCGCACTACAGGTCGACCAATTCCACGAACCGTGCGG
TTTGTGCAACATTTAGAGGTGAAGTTCTATGGCTGACCACTCAGTCGAGGACTACAT
AACCTTCGTCTGATCATGCTACCCGTCGTTATGTGTTACCATTGCAATTGAAGGTGA
TGACCATCTGCCTGCAGCATTGGACACTGTACACTGTACACCAGGATGACTATAGAGATGGTAGA
GCAGTTGGAAAGCATGCATCAGCGGAACGAACTGCCAGCGCCATACGCAACGTGGGGCAGAT
GCACAGTGGTTTACTGAAATGCATTAGGCTTTGAACACGTCAATCCGATCGATGCTGATGCTGC

*FIG. 4A*

AGTGGTTGACCTGCGTGTTAAACTGGAGCATTTCTCTCATCTATCTAACGAACCTGgttagttttgtctt
gtttggaaatccaaaaaccaaaaagatggctataattgaacttctattacagGGCCATTCGCTACAATCGGTTACCGTGGT
GGTAATGTTTTTCTTGCCACTGCGGAAACTTTCCTGTATGTTACTTGGGACGCGGCTTGCGA
CACAACAGCAGCTGCTGGAGCACGCACTCTATGCTACACGGTGTACAACTACCCAATAGCCTT
TCGCAGCAGCATTAGGATGATGTTGAGACAGTCGCAAAGGCATGCACACATAACGGTCGGGAAG
TTTTTCGGTTAATTTGAAGAATTTAGCAGGATTGTCAACTTATCCTACTTCTCTGCTTACGTCCT
ACTTAAGGATGTAATAAAGATGGATGTACAGTGAATGTTTTTTTTTTGCTTGGCAACGAATGA
AGTTTTCCGAATCTATATTAGATCTAGAATTTAATCTAGATGTCATAATATGATCTTGGCCATGA
CCGGTTCCTGGTTTTTGGAACTTCAAAACAATTTGAACTTAGGGCGAGGCATGAAATGTC
CCAAGAACCTATCCAAGTTCTGGAACTACATATTACCGAATCTATCCCATTATTGCCTCGAACT
GGTTTGGGTGCTAAATATTGTCAAATGTTGGTCCTGGACCTATCCAGACAAAGATCTTCAATTA
TTCCTACCACTGGAACTGATTAATTGATGTAGGAAGTCATGGAGGTGTTCAGGGAGAATTTAAA
CACTAATGTTCCAACTCATTATTTCAAGGCAATTTCTATTTTTATGCCCCTACGGATTGATAC
GTATGTATTACTCCATTTCTTATTTATGAGTGATACAGAGCCTTAAATACTCCTACGTTGTTTAA
GAAAAAGATTCTTATTTATTGATGATACAAGTCGAGATAACTGCAAACGATACCTACCTTCGAT
GTATGGCCAGGCTAATCACAATCGCTACTACATGCAAAGAATTCTCTAATTAAACCCTTCGAT
TGATAGTGTCAATGTCAATGTCGAGATAATTGAACTGCAAACTGCAAACGATACCTACCTTAAACGAGCAG
AACACATCAAGAAGCAATTAGGTGTCCGTACGTTAGCAAGTAGTTCGCGAGGAGGAATAAAAT
AG

*FIG. 4B*

ANOPHELES GAMBIAE

Preferred DNA Codons

| Amino Acids | | | Preferred Codons | | | | | |
|---|---|---|---|---|---|---|---|---|
| Alanine | Ala | A | GCC | GCG | GCT | GCA | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGT | GGA | GGG | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCG | CCC | CCA | CCT | | |
| Glutamine | Gln | Q | CAG | CAA | | | | |
| Arginine | Arg | R | CGC | CGG | CGT | CGA | AGA | AGG |
| Serine | Ser | S | TCG | AGC | TCC | AGT | TCT | TCA |
| Threonine | Thr | T | ACG | ACC | ACT | ACA | | |
| Valine | Val | V | GTG | GTC | GTT | GTA | | |
| Tryptophan | Trp | W | TGG | | | | | |
| Tyrosine | Tyr | Y | TAC | TAT | | | | | http://www.kazusa.or.jp/codon/cgi-bin/showcodon *(con'd on next line)*
.cgi?species=Anopheles+gambiae+[gbinv]

FIG. 5

| Name | SEQ ID NO |
|---|---|
| Arrestin 1(cDNA) | SEQ ID NO: 1 |
| Arrestin 1(polypeptide) | SEQ ID NO: 2 |
| Odorant Receptor 1(cDNA) | SEQ ID NO: 3 |
| Odorant Receptor 1(polypeptide) | SEQ ID NO: 4 |
| Odorant Receptor 2(cDNA) | SEQ ID NO: 5 |
| Odorant Receptor 2(polypeptide) | SEQ ID NO: 6 |
| Odorant Receptor 3(cDNA) | SEQ ID NO: 7 |
| Odorant Receptor 3(polypeptide) | SEQ ID NO: 8 |
| Odorant Receptor 4(cDNA) | SEQ ID NO: 13 |
| Odorant Receptor 4(polypeptide) | SEQ ID NO: 14 |
| Odorant Receptor 5(cDNA) | SEQ ID NO: 15 |
| Odorant Receptor 5(polypeptide) | SEQ ID NO: 16 |
| Odorant Receptor 6(cDNA) | SEQ ID NO: 17 |
| Odorant Receptor 6(polypeptide) | SEQ ID NO: 18 |
| Odorant Receptor 7(cDNA) | SEQ ID NO: 19 |
| Odorant Receptor 7(polypeptide) | SEQ ID NO: 20 |

*FIG. 6*

*Anopheles gambiae* odorant receptor 5 genomic sequence (SEQ ID NO: 21)

Predicted Exons: *ITALICIZED*, UNDERLINED AND BOXED
Introns: lowercase.

tctagacttgaaccatgacgggcattattgagtcgttcgagttgacgactgtaccacggaccacccgtttatcactatcactatt
aattaattaaatatgctttgtagcgatcagcctaccgggttttgttctctggatatcttaagttccattgattatcaagatagaa
caacaacttgtacctaaataatcattacgtaccctaatcaacctgtcatcaaggagtttcgcgaaagcaaaaatccgattgtct
gatgtgtcttgattccatccgattcgttactggttctgcaaatatgttattgcaaagaaggcaaggtaatgtgctaagagtaatacaattcgctg

| *TGCCTACCGAAGCTGTCCGAACCGTGTCCGACGCCCGTGATGCCGCTTCTACTACGCCGCCTGCAGCG* |
| --- |
| *TTTCGTTGGGGTCGTGTGGGTGAAGACGCTATCCCGAAGGTTGCCTGCTACAAGTTCCGGTTGGCATTTTA* |
| *AGCTTCGTCTGCTAGTAGTCGCGGAACAGCAGCCTGATTTCGAACGTGATTTCCAGATTAGAGAC* |
| *AATGGTTCGCGGAACAGCAGCCTAGACGACTATGACGACTATCTGGTGATCGTTGTTGGATGTTG* |
| *CTGTTTCTCAAGCTAGACGACTATGATGATCGTGGTGTACCGGTACAAGGACATATC* |
| *AAAGATTG*gtgcgtgataatgattgataaaggaacctttgagcaactcctatcccttcaag*CTTTCCGTAAGGAC* |
| *GTTCCCTCCGGCACAGCTACTCCTGTGTGCCGACATCTGTGTTGCCTATCATCATCCGATCCGGTTTC* |
| *CAAGATCACTGTCCTGGCAGCCATCCTGTGTTCTGCCCATCTCTACTGCCGTCCGGCTCCTTCGT* |
| *CCAGCACCTAGCACCTAGGAGCTGTACTGCCTAGCACCGGAAACAGACCCGGTCCGGAACATGT* |
| *GCTACACCTGGAGCTGTACTGCCTAGCACCGGTCGGGTCTACACCTATTTACCGGTAGATTAC* |
| *TCCATATTCACGCCAGCTCAGCTGTACTGCCTAGCACCGGTCGGGTCTCCTACTCCGGTGACT* |
| *AAGCTGCTAACCATCTTCAAGGTGAAGTACTGTTCGGAATGCTGGTGGTG* |

*Anopheles gambiae* odorant receptor 6 partial genomic sequence (SEQ ID NO: 22)

These are the predicted last three exons of another candidate *Anopheles gambiae* odorant receptor.

Predicted Exons: *ITALICIZED*, UNDERLINED AND BOXED.
Introns: lowercase.

aacaccccatcttatcggcaaaattagtattaccgtttgaaagcggcttccctcctggctgtttctcactctctctctgtctctctta
ttgatgccgtatgccgccgtgctataggctag*TATGCTTACGCACTGATGTTGCCGATGCCGTCTGCTTT*
*TCCCGCATACGGCCACTGCCACTGATGGCGGTTCCTGCAGTTGCTGCTGCGCACCGTT*
*TTCTGCTCGTGAGTCAGACCTTTCATTTGCAATATCCTGTTCTTCCGACCCC*
*ACAGACGGGTAGACGGATATGCTGCTGTGCCTACGCGGTGAGGATATTGTGGCTGCTTCTG*
*ATCGAGCCTGCTGATGCCTGCCTACGCGGTGAGGATATTGTGGAATCG*gtaaggcaccaggc
ggtgatgagcgagtcgcgagtaattgaagctttgctttaaaacacatcagag*CCTGGGGTGATTGATGCCGCT*
*TACGGTTGCCAATGGTACCGGGAAGGGTCCGGTTCCATCCGTCCCTGCTGCAAA*
*TTATACACCCAGCCAGTCCGTCATACTGACCGCATGGAAAATTTGGCCCATCCAA*
*ATGAGTACTTCAGTCAG*gtgagttgccaattgattgccgtttgcgttttgccttaatatttcagtaagagtgcgctctttccttag
*ATCCCTGCAAGCTTCCTGGTCCTTACCCTCCTGAAGACCGTCTACGGGAATAA*gtaa
gcgcgagagagagagagcagtatcgttcacccttggatgaatcaatagatttctaatcatgaaccattgaaaaatgaatca
acatttcgctagttgcacacaatattgtaccattctatacagcttcaccacgaccaagcgtttgttgttgcatcaggaccaaacacgtttcga
caagccgcgtcacctggc

FIG. 8

| FIG. 9A |
|---|
| FIG. 9B |
| FIG. 9C |
| FIG. 9D |
| FIG. 9E |
| FIG. 9F |
| FIG. 9G |

*FIG. 9*

*Anopheles gambiae* odorant receptor 7 genomic sequence (SEQ ID NO: 23)

Features
1. Predicted Exons (7): ALL CAPS, ITALICIZED, UNDERLINED, BOXED
2. Introns (6): lowercase
3. 5' and 3' sequences: lowercase, dotted underlined ccgccccgggcaggtgacttacgccggtctgacttgctggtgcgctctgacttgctgctgactcgttgtacggcaaacggctacacaagcgaatcgaattattttcc
tatcacgctgcgcttaccagcctgctgtggtaggcaaagaatgtgcaaagtttcatttggctcttgttgtctgctgtgtgtgaacgtgt
gcacggttgcatcgctaaggttcggttgtgagccgagaagttgcagatcgaagaagttgcgagatcgaaatctctttgtgtgtgtgcagtgggaa
gcattgtgtttagtgagagtgaaaagaaagtgctgaaaatgcgaccaagtccagccgaccaagtacgtcggccttcgttgccgacct
gatgccgaacattcggttgatgcaggccaggcggtcaacttctctgttccgctacgtcaccgccccgatactgatccgcaagtgtac
tcctggtgacgctcgccATGGTTGCTGATCCCAGTTCTTGATCCCATCCTTCGGCAACCTGGCAACCTGGCGACGA
ACGGACGACGAACGAGCGCCAACACGGCCAACGATCACGACCGTTCTTCACGCA
CTCGGTTCACCAAGTTCATTCTACTTTGCCGCAACACGGCCAACTTCTTACCCGGACCTC
GCCATCTGGAACCAGACCAGACCCAAGATCGCCAACGATGCGGAAGAGCGCCGGTACC
ATTCGATTGCGAACTCGCAAGAGCTGTTGCCGAATCGGTGCTGGTGATGGCCACCGT
CCTGTCGGTGTCGgtatgtgtatgtgtggtgcgtttggagaagtgtctttgcggcagaacccaatctactgttacgc
ttgactggttttgttttttctcggtggagggacgggataaaatatctgaaagaataattgatgcaaccacaggggatgcaag
acatcgcaggcaggaggatttgggtttgatttatcaccgcacaccgaatatcttcacgttcataagcttcaccgcggtgaaaaggga
actcccccattccctgcagagagtttgcttttctttcgtttgtgctgttctttctttcttcatc

*FIG. 9A* cctactagCCTGGGTTACGATAACATTTTCGGGAGAGGTCAAGACTGTGCTGGATAAG
GCAACCAAGAGACTACACGGTGGATATACCCGGCTGCCATCAAGTCCTGTATC
CGTGGAATGCAATGACGGCTACATTTCTTTCATCTACCAGGTACGTTG
GCGGAATgtcctgcgtcacagttgcagtcagtgagcggcaacacggcaaaaatggactaaaccggtcttcacaga
gccaacacattcctacagcaattgcatacctcggggcgtcggactgcagtgcagtacaacatctcgcctaaagttatgcaat
tcgagcgacaaatgttgccgtgttagggctgttttttgtgataatagtcgttttttgtcctctcgctatcaaactctatcaacggaggaaa
tccattttgctacaatgcctacacagctcaagttcaaggtcaagctgaggtgggatcaacttttatcattgctaacgcccca
tcaacaaattctatgttctcaatgcaaagattactgcccgcaccaatcgcccaacgaaacggcaaaagaaaagcgacgattatga
agatgtccaaaccattgcccgccccgacgctgtttatctgatgatttgcggatggctttactgtctgctactttcaggcacaaaggaa
atgaaaccagcgcaggctcgtttgccgctgccgaggttcttcaggacgtcgagtactaaatcgaacgattttttacgattc
tggatccagtgttttatgatgtggcctgcattacagtggcaattataccctgatgttcattcattgtgctggtaacg
ccgtaacgattaattctttcaaagagattctttaaaatattcatcacaatctctgcaaactgttaattaatgctcacaataagttaaact
agggttgcggaaagtaacgttttaaagtttaaatgtgtgctcgcttaattggtgtgcacaataagttggcacaataagcgttgtg
gtggcggcagatgtgtccgctccgctccgcttccctgccgaaataattattccatcattttaatacagccgttgtg
cattttaattagcaaagcaatataaaagcagctaacaccatccccattaaaaacaaagtgcttccggccccaattgttatggccggtgga
aagtaatggttttaccagtggaagtgtccttttccatcgtgttaaagtgcttacaagtgcatacagaaaaaaa
ggacaaatctccttgctatggtctaaggccagctttgtaccgcttcgttgtcgtcgggatgtcataaagtttgatggtgttttaacatt
acttccgctcttaaccaccactaatgactttcatgctgagctaaagtaaaccagccgtacgcgaccggttcacgagcacggagttgatt

*FIG. 9B*

```
tcggcggcggcctcatcccagtttgcgccaccaatattgccttcattaatctgtacctcggagcgttagggccgcggacgagtcct
cgttgtaatgcaccgccatgccacggacggatataatccgtgggacggcgcgaaagcgactatcgcggacggattggttcgaccg
tgctacaacacatttatgcttcacagatttactcctgctgtttcgatggtcgtcagagcaactcgcggatgtcatgtttctgtcctggt
tgctgctagcctgcgagcagctgcaacacttgaaggtaggtacggtagcaacgtggtcttacatccgcgtgcagcattatcct
tatcgacgtgtagtgtgtaacgtgtctctctctctctctctctctcacacctgatctctctttatttctctctct
ctctctctctctctctctcctcgacacctaccggcccaactcttcgcaactgttccgagcaaGGTATTATGGATGGTTGATG
GAGCTTCGCTCCCTGGACACCTACCGGCCCAACTCTTCGCAACTGTTCCGAGCAA
TTTCAGCCGGTTCCAAATGCGAGCTGATCATCAACGAAGgtatgtgaaacgtgtgctgtggcagacg
gactcaaagagagagcataacacaatccctgtagttcattcaatgacttaacactcggcaagctaagcgagacagtggggacag
tgagaaagagagaacaagaaaaaaaaccatcatcgtacgacatcatcgctacggtatttcaggatgaggaataaaac
gctagggaatgaaagtgcgacagagaatgataaacaatcccaccagcccccacatttcccgtccatcagtgagtgtgcgaagc
gagcaaaaaagtcaaataaattgaagttaaaaatagatttcccgtcctgtggagcgtaaagcccggcgacaactt
cgagcacggcgaccgtgcacagtactgtgccacagtgtgtaggacgtgatagctcgttcttttatctcttttttggagattgt
ttgcgttcgcatcgttagacgagctcgttagtgccgtgttgctctcaattgctattattataaagcttccaatagaagatcggttctctc
cattaatctatcgccgcctacgcctgaaactacactgtgctgtgaacaaacctttgcctaccatccaatccgtgtgaaattgcccgctctcttt
acgcccgtggtgccaaagccgcaacgcatgcatgttaacacgcgaattgcatgtttcctttttttactttgcgtgtgtgttttttaataaccgctccagttcgttgaacg
ctgacggtggtgggttttcgaaaaaaagagcgattctttctgcgtgtgtgttttttaataaccgctccagttcgttgaacg
ctgcaggaccgatcggagctagttattatcagctttagtgttatccaccatgcccacatcacgtctgtggagagtggggaag
cttaagtccaatgtaattaccgtgttctgttctgtcgtcacctcttcgtgatggagattggtgccggttgcacgataaaagcccact
gcacgttacggaccgagggaaaggtcttttgtaggcctagcaacgtcctcattcaccgcatggggggtgtagctcagatggtagag
cgctcgcttacggacccgaggtacggtaccggatatacccggcgatctccaaccacaacaaaacgttttaagaaagattttagggaa
gatattaacgcggtacactgtgctcctcaagttggaagagtagatgatgacaaggagaaggaagaacatgtgtacgtgttt
```

*FIG. 9C* gatagcaaacacacaacaacatatctgataataatctgatatgtgtgatgtgtgtgtattgtgttatgctgctttgccatct
tgtccctctctcctgttcaactcctaaagaattgtttggagtcctctcagttcctcgtaaagatccttcgagatctcttcctttt
attatttattccacgagcctctgacataagtagcctccgcttattctcctgcactgtcagttccgttcgtgagagcgtcattttgag
gtttacacatttcccaccgacgcctgattgttacattgtcatctacattgcttcgcttaccgttccgccctttttttttaacgctaccaca
gAAAGGATCCGGACTTAAGGACTTGATCTGAGGCATCTAGGGCATCTACAGCTCGAAGGCGG
ACTGGGGCCGGCCAGTTCCGTGGCGCGTGACGCTGCAAACGTTCGACGAGAATGGCAG
GAACGGAAATCGAACGGGCTACCGGAAGCGAAATGATGCTGCGCCAGGCCATC
AAGTACTGGGTCCAGCGGCCACAAGCACGTTGTACCgtaggtatggtaatttctaaggtgtggtgtaaag
cctccaggttccatgaaaagggatacttaccacagtaagagtttgttgtctggacttacattcttggagcattgtttggtgtgtg
ctgaaaccggttgcaatatcgtttgcgaagaaatttgtaaagcgtattacaatctcattcctcgttaatctgtaccaattgtc
agccccgaccgaaagcaggcctaattcgtaccagaaaaaaccacaagctgtttgtaagcatcgatacgcccgaagctttcaatccagc
caaggcgccacctactattgacgtgactttttgcacttcacactctccctcccattcttctataaccaatcgtcgtcagcagcat
cgcccggagtgaagttttattgaacgatatcacccgtatcgatttccactaaacatgcttaaatgttcacaaagctccccaaa
atcccatttcaccaatccaccaattgaagtccgtcgtcgtcttgtgtttgtgtgtgagctggagacatggggagt
gagtaaccgaacaacctctgccgctcttcacgatatcgaacagcaccaagataagcatccctttcctagccgatgtctccgata
tctcgattccgcttccagcgaggcaaagaaaagcgaactgctgacctcaccgctgacctgacgtttccattaccgcctgcgagtgcacacgtgaag
gagcagcagagttgtgattctttctctggttcctctgttcctataaatcgctcccttcgtttttggtgaagatccttatcggtgaccact
ggaaaagcgaaaacgtttagattccagcaacgcagcagcagcgcggcaaatgaatcatctgacgcgat
gagttgtctgagagcgaggttccggttttcgggtggttggcttacagcaccaccacatctgctgcagctaatacagctgtaaattcgttagacatagactt
gatttacaatattacaacacttacacacagctatagatttgtcgctggcctggcgtacggcgtgccgtacatgccgc
gagccgtgttgtgctgctggttgcatacgatcacgtccgattcagtcgattggaaaagctaggctcgattcaaagggccattgtgccagtgttctt
ttcagtgtgtcgagagcgaggtcactatggcgcctgtcagttggaaaagctaggctcgattcagttggaaaagggccattgtgccagtgttctt
ttaagatagcgataaagcttttgatcgaaatagtaaatcaaacattgttttcttttcctattccaaactgttgccaacctcattattacg

FIG. 9D

```
tttttgcagcgggtgtatagtaaattgcatactttaaggcgtgatttcaaatgtagcgttccgtatgcagaaacgccatggattatgc
aatttaaacaatgcttcctttaacattcaaataacgcttattaaggaactttttgtgcaatttgtttttaacagcaaatagttagc
tcagaacgatcacattagtatcgcttcaacacaagaactcttttaaacacacacaatttgtaatgccattccctgagaaagttcttgtc
agtcctcctctgcatcacacagcaacaaccaaacctgctcatgttcctgcctcgtttctagctgttttgaacgttattccgattcctgtct
tgcccgcttttcttacaatcaaccacaatgttcagatttcgctctatttattgaccactgctttcgtgctgaagccgtggaaacaa
tgcgccaagctcagcatccagccatgcatgtaaaatgagccacgcgatgtaaatttagacatcgcttcgctctgcaccgaggtggt
ttattcttgtttccgattcccacgtccattcgtcctgggtccgtccgcgaaaccgtaagcgtgcgggaattacgcaatcga
aacgagccagacgaaaatgagcacgccaaatgcaaagaaacatccctttgagtggtgctcctgccaccactcatctcccaactggtgg
gtgaaaacctgtgcgcccctctcttccagaaaaaaaacgcctcgctgcacaaaaacatgctcgccggtgaagctgcgtatgt
cgcagaagctcaaaccaacgccgcagcatcaacaatttctattcaaaacaccaacgcagcgccaaacgggtgcactgta
ctcagtagcgaagatgctcagattgtccgtgcgctgcctttcgatgcccgtttcgagcggaagcatcgttgccaacgttggcgat
gtctttagcgcgtggatttgaatttctgaatatcacaggcggggcgcgttgcctgcaaggttgttgcttcccacacgagcattgcttt
ccgtaccgcggtggggcgagttttcaacgcaaccttctacaagcaacgccacaacgcctgggagcgatatttaacagaaacaagaa
catcccgaacttcagcacgcacatgccgtgattgcctgttggaaaagctttgtgagcgtgtgagttgaacgagctctatttccagcgat
gggtggcatttgtgtggcatgctatcgtcagctttctcgaatctttcttacctctccattcgcctccattagtacacgctatggaaatgg
gtgcaacgatcagaacggatttccgcgacagactaataataacagtttttttgaaagcaacgcgtttttgcatgtgtagtgttatgagcttt
atgccgttactttgcaattaaaatagcaaaaataagaatagatagtttgtaacacggattgcaacactgccggtatcggttacatttcgccta
aaacattcattcatgctgttaacgctcaaatagaataagtttgaacacggattgcaacacaaatatcagaatattacgtg
acagtatgcaatctgttagctttgttgttaatgactgcgttggtagtacaatattatttaccacggtaatttatctcacaaattgc
aaaaaaatgtcaatctgtatcgattatcacacaatcagatcccgaaccagtgtagccaatgtgctcttattgaattaccacga
acaaatcaacctgacccggttggcaaacagcttgcgccgaagccgctgcactaccgtgtttcgtgcactaccgtgctgcatttgct
gccctcatcgaacagataaacagaagggcaactcttgtgagcatcgcaatgcccgtctgaagttccgtcgaaaatgggctaaattc
aatttgacgcattaccgcgaacaattgccgcgaaggctgtcaagtgttccacgaactgcgacaacaagcacacacaacac
```

FIG. 9E aaatgttatcgttctcggcatgtttctcggtacaaagcgtgtggcgctatgtggcatgccgattcccagacagagtgatcgtagtaaa
tgtagcctatccggtagcattcaattccttctatcctcgcaaacaaagcccattctggggaggcgtggtgaagctttcaaaggcat
tgtgaaacaaatgtcctggttcggaggagcaaacacggtcgccgccatcgctgctacggtcaatcgatcatgcat
atgtgattaatatttgtgttattcacctgcgtatctatgcgtcgtgtcgttcggatttccgaagtcaaggaaaaagcgactca
tttgggattggttttttgcagcgaaatcaaaacattcgcacaaacgtcctccatttcaattgcctacactgtcactgtatatctct
ctttctctcgttttgcccacgttgcagTCTCGTTTCAGCAGTCGAGATACGTAGCGTCCTCCCTGCT
GCTACACATGGTGCTGACCTGACCTCCACCATCCAGCCTCGGCTTACCAGGCAACGAAA
ATCGACGGTGTCAAGGTGTAGGATTGACCGGTAATCGGTATATTGTGTCTACGGTGG
CTCAGGTTTTCGTTTTTCCTGTGTTTTGCATCTTGGCAATGGCTCATGAGGAGgtacgtgcgctcggcgtg
ttgccgtgggaaagcattctccctgccccatatcgcttcattctccagatcgctcacacatttgcatcacaaagccagcacactttgcttcg
ccgctgccatctcggcttctgaatgttttcacttctcccatactcctcccgtgcagAGCTCATCCGTGATGAAGGGGC
CTATTCCTCCCACTGGTACGGGCGTCCGAGGCGAAGGGCGAGATGATCCATTGGTT
TGTCAGCAGTGCCAGAAGCAGCGATGACTATTTCCGGAGCCAAGTTTTTCACGGTTTCGC
TCGATCTGTTTGCTTCCggtaagtgtagcctggtggtggcacagaacaggctggcaaaacagggactttggctctagc
ctgatggctgtatatgtgtgctggtgctacccattctgcatccctccctttccagGTTCTTGGAGCCGTTGTGTCAC
CTACTTCATGGTGCTGGTTGCAGCTGAAGTAAacagccgtgcccgaaggatgtgttttttcgctcgttcg
gttgtttgtttgtgcacactttctcttgacactttctctactgcaaaggtttaacaacacagcaacaacaaatatccaagttttctttt
acagatctttgcaaaatttgattagatttataaatgctgattatctgtcctgtagcaaccgggctgaagaacgttgatt
tggtaaagtacaaggacgttggaaattgaaccaccagagagagtcacctaccaaggaaaatcatgtat
gtgtgatttgcctcatcaagcactgtatgtgccttaactagtgcagcaataagagtacaaaatgttcttagcgcaccgtacattg
tcgtttcggcgtttaaccgttgttgataatacacacaaaagatgtaataataacaaaatgtaatatgagtaagtacta
aatagagaaatcgttttagtatgatcatacctccaatcatttgtttgaaattaacttaatttaactcaaattaaccgatgttttact
ttctgtgagaattattgtgaagaacttaatggaagtataattaattgattgctaactttatcgtttcattacgaacgctagt

*FIG. 9F* cttcaaacatcgcttcaaaagtattactaccacattattcattacttatagttatatttattgcctcttcatctttcatggccagaact
actgcagaaaagcttcttttttgctcgctttccgatggttggttgttggacgagttggtaacaaacggcaagcaattagcataaactatt
ttcgcatcgagatggaaatgaatgtaccactagaaccgagtgaatgaattactttcaacttgcacgccaaaccattatctaaag
tacggcacaacttaaaaacaaacccaaattgtcgtccaccttcattcttcctacacttcttgctacacttcctgaccgagttctgtagcgccag
cagcaaaaatacatataaaaccttcatcactcaagctgtatcgagccagcgtgggttgtgtttgactgctgtgaaagaaaga
agaaaaaaacacttccacgggaagctagcaattggaaatgcataaattaaccggaagaaattcgcaaaacccgcaccgac
gtaccgcaccgcatccgtaccgatccggaacaaacgtgtgccgcaaaatccgctagcagtcgagccccactgccagccctttgctt
ttggttctgtgttttcttccactggttgggtgcctggggcgaaggctagctcggctacttccgggccgcaattttctgcagcccaag
gcgggcgtgctcgtggggccaaaagaat

FIG. 9G

SEQUENCE LISTING

<160> NUMBER OF SEQ ID NOS: 23

<210> SEQ ID NO 1
<211> LENGTH: 1964
<212> TYPE: DNA
<213> ORGANISM: Anopheles gambiae

<400> SEQUENCE: 1

| | | | | | |
|---|---|---|---|---|---|
| acaggaacga | cggttgtgat | ccctccactg | gtggtgacac | gaatcataag | cattatttca | 60 |
| tacctaaaaa | acaaaatcta | caaaaaaaag | cttcattccc | atcgaaaaaa | ctttcttgtg | 120 |
| aaatcaaccg | agctaacaaa | caacatcctg | tgcaaaatct | agcagtgaaa | gtgtgatatc | 180 |
| gtatacctgt | acctgtaaac | cgttgtgcgc | gtgtgtgcct | ttgtgtatca | attttgtgga | 240 |
| aaacagaaaa | tacatcaaaa | tggtttacaa | tttcaaagtc | ttcaagaagt | gcgcccctaa | 300 |
| tggaaaggtt | acgctgtaca | tgggcaagcg | tgactttgta | gaccacgttt | ccggcgttga | 360 |
| accgatcgat | ggtatcgtcg | tcctcgatga | tgagtacatt | cgtgacaacc | gtaaggtatt | 420 |
| cggtcagatt | gtctgcagtt | tccgctacgg | ccgcgaagag | gacgaggtga | tgggactaaa | 480 |
| cttccagaag | gagttatgcc | tcgcttccga | acagatctac | ccgcgtccgg | aaaagtcgga | 540 |
| caaggagcag | accaagctcc | aggagcgact | gctgaagaag | ctgggttcga | acgccatccc | 600 |
| gttcacgttc | aacatctcgc | cgaatgctcc | gtcttcggtc | acgctgcagc | agggcgaaga | 660 |
| tgataatgga | gacccgtgcg | gtgtgtcgta | ctacgtgaag | atctttgccg | gtgagtcgga | 720 |
| aaccgatcgt | acgcaccgtc | gcagcaccgt | tacgctcggc | atacgcaaga | tccagttcgc | 780 |
| accgaccaag | cagggccagc | agccgtgcac | gctggtgcgc | aaggacttta | tgctaagccc | 840 |

```
gggagagctg agctcgagg tcacactaga caagcagctg tacctgcacg gggagcgaat      900
aggcgtcaac atctgcatcc gcaacaactc gaacaaaatg gtcaagaaga ttaaggccat     960
ggtccagcag ggtgtggatg tggtgctgtt ccagaatggt agctaccgca acacagtggc    1020
atcgctggag actagcgagg gttgcccaat tcagcccggc tccagtctgc agaaggtaat    1080
gtacctcacg ccgctgctgt cctcgaacaa gcagcgacgt ggcatcgccc tggacggtca    1140
gatcaagcgt caggatcagt gtttggcctc gacaaccctc ttggctcaac cggatcagcg    1200
agatgctttc ggcgttatca tatcgtatgc cgtaaaggtt aagcttttcc tcggcgcact    1260
cggcggcgag ctgtcggcgg aacttccatt tgtgctgatg cacccaaagc ccggcaccaa    1320
ggctaaggtc atccatgccg acagccaggc cgacgtagaa actttccgac aggatacaat    1380
cgaccagcag gcatcagttg actttgaata gacgacgcaa cggtttggaa atgctaccta    1440
ctacccagg catgggctaa cacgacgaac gaactactac tactaagcat aaaaaacagg     1500
aaaaaaatg gaaacttaa aaatggatc atacaaccga acgcaaacga cctacgacga       1560
tcgatctcac ttccccgtct ttttcatcct aagcaataga acgatggtag aaaaggaaga    1620
taaagatgga gagaaagtca cgtgtatcaa tgacgacgac taccaaaact gaagacgtaa    1680
cacatgttcc ccagcgagcg gtaactgttc tgttctgaca ccttccgctc gacaatgtac    1740
cttttaaaaa catacaaatt agaagtcgtc ttcactacct tcaaccaatc cagccacttt    1800
ggtatatact tttcatagaa tccttctgag cgcaaggacc ctattgaaat tcagtgttat    1860
tttgtaactg cgaccaaatg cctagctgaa tgttgttgaa cgagttatgt acatcaaaag    1920
attgaataaa acaaaaaaaa aaaaaaaaa aaaaaaaaa aaaa                       1964
```

<210> SEQ ID NO 2
<211> LENGTH: 383
<212> TYPE: PRT
<213> ORGANISM: Anopheles gambiae

<400> SEQUENCE: 2

```
Met Val Tyr Asn Phe Lys Val Phe Lys Lys Cys Ala Pro Asn Gly Lys
 1               5                  10                  15

Val Thr Leu Tyr Met Gly Lys Arg Asp Phe Val Asp His Val Ser Gly
            20                  25                  30

Val Glu Pro Ile Asp Gly Ile Val Leu Asp Asp Glu Tyr Ile Arg
        35                  40                  45

Asp Asn Arg Lys Val Phe Gly Gln Ile Val Cys Ser Phe Arg Tyr Gly
    50                  55                  60

Arg Glu Glu Asp Glu Val Met Gly Leu Asn Phe Gln Lys Glu Leu Cys
65                  70                  75                  80

Leu Ala Ser Glu Gln Ile Tyr Pro Arg Pro Glu Lys Ser Asp Lys Glu
                85                  90                  95

Gln Thr Lys Leu Gln Glu Arg Leu Leu Lys Lys Leu Gly Ser Asn Ala
            100                 105                 110

Ile Pro Phe Thr Phe Asn Ile Ser Pro Asn Ala Pro Ser Ser Val Thr
        115                 120                 125

Leu Gln Gln Gly Glu Asp Asp Asn Gly Asp Pro Cys Gly Val Ser Tyr
    130                 135                 140

Tyr Val Lys Ile Phe Ala Gly Glu Ser Glu Thr Asp Arg Thr His Arg
145                 150                 155                 160

Arg Ser Thr Val Thr Leu Gly Ile Arg Lys Ile Gln Phe Ala Pro Thr
                165                 170                 175
```

-continued

| | | | | | | | | | | | |
|---|---|---|---|---|---|---|---|---|---|---|---|
|Lys|Gln|Gly|Gln|Gln|Pro|Cys|Thr|Leu|Val|Arg|Lys|Asp|Phe|Met|Leu|
| | |180| | | |185| | | |190| |

Ser Pro Gly Glu Leu Glu Leu Glu Val Thr Leu Asp Lys Gln Leu Tyr
 195 200 205

Leu His Gly Glu Arg Ile Gly Val Asn Ile Cys Ile Arg Asn Asn Ser
 210 215 220

Asn Lys Met Val Lys Lys Ile Lys Ala Met Val Gln Gln Gly Val Asp
225 230 235 240

Val Val Leu Phe Gln Asn Gly Ser Tyr Arg Asn Thr Val Ala Ser Leu
 245 250 255

Glu Thr Ser Glu Gly Cys Pro Ile Gln Pro Gly Ser Ser Leu Gln Lys
 260 265 270

Val Met Tyr Leu Thr Pro Leu Leu Ser Ser Asn Lys Gln Arg Arg Gly
 275 280 285

Ile Ala Leu Asp Gly Gln Ile Lys Arg Gln Asp Gln Cys Leu Ala Ser
 290 295 300

Thr Thr Leu Leu Ala Gln Pro Asp Gln Arg Asp Ala Phe Gly Val Ile
305 310 315 320

Ile Ser Tyr Ala Val Lys Val Lys Leu Phe Leu Gly Ala Leu Gly Gly
 325 330 335

Glu Leu Ser Ala Glu Leu Pro Phe Val Leu Met His Pro Lys Pro Gly
 340 345 350

Thr Lys Ala Lys Val Ile His Ala Asp Ser Gln Ala Asp Val Glu Thr
 355 360 365

Phe Arg Gln Asp Thr Ile Asp Gln Gln Ala Ser Val Asp Phe Glu
 370 375 380

<210> SEQ ID NO 3
<211> LENGTH: 1239
<212> TYPE: DNA
<213> ORGANISM: Anopheles gambiae

<400> SEQUENCE: 3

```
atgaagctga acaaactgaa cccacggtgg gatgcgtacg atcgacggga ttcgttctgg      60
ttgcagttgc tttgttttgaa atatttaggc ctatggccac cggaagatac ggatcaggca     120
acgcggaacc ggtacatcgc gtacggttgg gctttgcgga tcatgtttct acatctgtac     180
gctctaacgc aagccctata cttcaaggat gtgaaggata ttaatgacat cgcaaatgca     240
ttgttcgtgc ttatgactca agtgacgttg atctacaagc tggaaaagtt taactacaac     300
atcgcacgga ttcaggcttg tctgcgcaag cttaactgca cactgtatca cccgaaacag     360
cgcgaagaat tcagccccgt tttacaatcg atgagtggag tgttttggct gatgatcttt     420
ctcatgtttg tggctatctt caccatcatc atgtgggtta gtcgccagc cttcgacaat     480
gaacgtcgtc tgcccgtgcc ggcctggttc ccggtggact atcaccattc ggacatagtg     540
tacggtgtac tgttcctgta tcaaaccatt ggaatcgtca tgagcgcaac gtacaacttc     600
tcgaccgata ccatgttttc cggcttgatg ctacacataa atggacaaat tgtgcggctt     660
ggtagtatgg ttaaaaagct tggacatgac gtccctcccg aacgccaatt ggtcgcaacg     720
gatgcggaat ggaaagagat gcgaaagcgc atcgaccatc actccaaagt gtacggtacg     780
atgtacgcta agtaacgga gtgtgtgctg tttcacaagg acatcttaag gatctatctt     840
cgcgcaagta tgcgcgtctg taattatcat ttgtatgaca ctgctgcaac taccgggggc     900
gatgttacga tggccgatct gctgggctgt ggggtctatt tgctagtaaa gacatcgcaa     960
```

-continued

```
gtgtttatttt tctgttacgt agggaatgaa atctcctata cgacggataa atttacagag   1020
tttgttgggt tttccaacta cttcaagttc gataagcgta ccagccaagc aatgatattt   1080
tttctgcaaa tgactcttaa agatgttcac atcaaggtgg gaagtgtctt gaaggttacg   1140
ctaaatcttc acacattttt gcagattatg aagctatcgt actcctatct ggccgtactt   1200
cagagcatgg aatcagagta atggtgttaa tatccttaa                          1239
```

<210> SEQ ID NO 4
<211> LENGTH: 394
<212> TYPE: PRT
<213> ORGANISM: Anopheles gambiae

<400> SEQUENCE: 4

```
Met Lys Lys Asp Ser Phe Phe Lys Met Leu Asn Lys His Arg Trp Ile
  1               5                  10                  15

Leu Cys Leu Trp Pro Pro Glu Asp Thr Asp Gln Ala Thr Arg Asn Arg
             20                  25                  30

Tyr Ile Ala Tyr Gly Trp Ala Leu Arg Ile Met Phe Leu His Leu Tyr
         35                  40                  45

Ala Leu Thr Gln Ala Leu Tyr Phe Lys Asp Val Lys Asp Ile Asn Asp
     50                  55                  60

Ile Ala Asn Ala Leu Phe Val Leu Met Thr Gln Val Thr Leu Ile Tyr
 65                  70                  75                  80

Lys Leu Glu Lys Phe Asn Tyr Asn Ile Ala Arg Ile Gln Ala Cys Leu
                 85                  90                  95

Arg Lys Leu Asn Cys Thr Leu Tyr His Pro Lys Gln Arg Glu Glu Phe
            100                 105                 110

Ser Pro Val Leu Gln Ser Met Ser Gly Val Phe Trp Leu Met Ile Phe
        115                 120                 125

Leu Met Phe Val Ala Ile Phe Thr Ile Ile Met Trp Val Met Ser Pro
    130                 135                 140

Ala Phe Asp Asn Glu Arg Arg Leu Pro Val Pro Ala Trp Phe Pro Val
145                 150                 155                 160

Asp Tyr His His Ser Asp Ile Val Tyr Gly Val Leu Phe Leu Tyr Gln
                165                 170                 175

Thr Ile Gly Ile Val Met Ser Ala Thr Tyr Asn Phe Ser Thr Asp Thr
            180                 185                 190

Met Phe Ser Gly Leu Met Leu His Ile Asn Gly Gln Ile Val Arg Leu
        195                 200                 205

Gly Ser Met Val Lys Lys Leu Gly His Asp Val Pro Pro Glu Arg Gln
    210                 215                 220

Leu Val Ala Thr Asp Ala Glu Trp Lys Glu Met Arg Lys Arg Ile Asp
225                 230                 235                 240

His His Ser Lys Val Tyr Gly Thr Met Tyr Ala Lys Val Thr Glu Cys
                245                 250                 255

Val Leu Phe His Lys Asp Ile Leu Arg Ile Tyr Leu Arg Ala Ser Met
            260                 265                 270

Arg Val Cys Asn Tyr His Leu Tyr Asp Thr Ala Ala Thr Thr Gly Gly
        275                 280                 285

Asp Val Thr Met Ala Asp Leu Gly Cys Gly Val Tyr Leu Leu Val
    290                 295                 300

Lys Thr Ser Gln Val Phe Ile Phe Cys Tyr Val Gly Asn Glu Ile Ser
305                 310                 315                 320
```

```
Tyr Thr Asp Lys Phe Thr Glu Phe Val Gly Phe Ser Asn Tyr Phe Lys
            325                 330                 335

Phe Asp Lys Arg Thr Ser Gln Ala Met Ile Phe Phe Leu Gln Met Thr
            340                 345                 350

Leu Lys Asp Val His Ile Lys Val Gly Ser Val Leu Lys Val Thr Leu
            355                 360                 365

Asn Leu His Thr Phe Leu Gln Ile Met Lys Leu Ser Tyr Ser Tyr Leu
            370                 375                 380

Ala Val Leu Gln Ser Met Glu Ser Glu Glx
385                 390

<210> SEQ ID NO 5
<211> LENGTH: 1142
<212> TYPE: DNA
<213> ORGANISM: Anopheles gambiae

<400> SEQUENCE: 5
atgctgatcg aagagtgtcc gataattggt gtcaatgtgc gagtgtggct gttctggtcg      60
tatctgcggc ggccgcggtt gtcccgcttt ctggtcggct gcatcccggt cgccgtgctg     120
aacgttttcc agttcctgaa gctgtactcg tcctggggcg acatgagcga gctcatcatc     180
aacggatact ttaccgtgct gtactttaac ctcgtcctcc gaacctcctt tctcgtgatc     240
aatcgacgga aatttgagac attttttgaa ggcgttgccg ccgagtacgc tctcctcgag     300
aaaaatgacg acatccgacc cgtgctggag cggtacacac ggcggggacg catgctatcg     360
atatcgaatc tgtggctcgg cgccttcatt agtgcctgct tgtgacccta tcctctgttt     420
gtgcccgggc gcggcctacc gtacggcgtc acgataccgg cgtggacgt gctggccacc      480 ccgacctacc aggtcgtgtt tgtgctgcag gtttacctta ccttcccgc ctgctgcatg      540 tacatcccgt tcaccagctt ctacgcgacc tgcacgctgt ttgcgctcgt ccagatagcg     600
gccctaaagc aacggctcgg acgcttgggg cgccacagcg gcacgatggc ttcgaccgga     660
cacagcgccg gcacactgtt cgccgagctg aaggagtgtc taaagtatca aaacaaatc      720 atccaatatg ttcatgatct caactcactc gtcacccatc tgtgtctgct ggagttcctg     780
tcgttcggga tgatgctgtg cgcactgctg tttctgctaa gcattagcaa tcagctggca     840
cagatgataa tgattggatc gtacatcttc atgatactct cgcagatgtt tgccttctat     900 ggcatgcga acgaggtact ggagcagagc ctaggcattg gcgatgccat ttacaatgga     960
gcgtggccgg actttgagga accgataagg aaacggttga ttctaattat tgcacgtgct    1020
cagcgaccga tggtggtaag attaaagtcg gcaacgtgta cccgatgacg ttggaaatgt    1080
ttcaaaaatt gctcaacgtg tcctactcct atttcacact gctgcgccga gtgtacaact    1140
aa                                                                   1142

<210> SEQ ID NO 6
<211> LENGTH: 380
<212> TYPE: PRT
<213> ORGANISM: Anopheles gambiae

<400> SEQUENCE: 6

Met Leu Ile Glu Glu Cys Pro Ile Ile Gly Val Asn Val Arg Val Trp
1               5                   10                  15

Leu Phe Trp Ser Tyr Leu Arg Arg Pro Arg Leu Ser Arg Phe Leu Val
                20                  25                  30

Gly Cys Ile Pro Val Ala Val Leu Asn Val Phe Gln Phe Leu Lys Leu
            35                  40                  45
```

```
Tyr Ser Ser Trp Gly Asp Met Ser Glu Leu Ile Ile Asn Gly Tyr Phe
 50                  55                  60

Thr Val Leu Tyr Phe Asn Leu Val Leu Arg Thr Ser Phe Leu Val Ile
 65                      70                  75                  80

Asn Arg Arg Lys Phe Glu Thr Phe Phe Glu Gly Val Ala Ala Glu Tyr
                 85                  90                  95

Ala Leu Leu Glu Lys Asn Asp Asp Ile Arg Pro Val Leu Glu Arg Tyr
                100                 105                 110

Thr Arg Arg Gly Arg Met Leu Ser Ile Ser Asn Leu Trp Leu Gly Ala
            115                 120                 125

Phe Ile Ser Ala Cys Phe Val Thr Tyr Pro Leu Phe Val Pro Gly Arg
130                 135                 140

Gly Leu Pro Tyr Gly Val Thr Ile Pro Gly Val Asp Val Leu Ala Thr
145                 150                 155                 160

Pro Thr Tyr Gln Val Val Phe Val Leu Gln Val Tyr Leu Thr Phe Pro
                165                 170                 175

Ala Cys Cys Met Tyr Ile Pro Phe Thr Ser Phe Tyr Ala Thr Cys Thr
                180                 185                 190

Leu Phe Ala Leu Val Gln Ile Ala Ala Leu Lys Gln Arg Leu Gly Arg
        195                 200                 205

Leu Gly Arg His Ser Gly Thr Met Ala Ser Thr Gly His Ser Ala Gly
210                 215                 220

Thr Leu Phe Ala Glu Leu Lys Glu Cys Leu Lys Tyr His Lys Gln Ile
225                 230                 235                 240

Ile Gln Tyr Val His Asp Leu Asn Ser Leu Val Thr His Leu Cys Leu
                245                 250                 255

Leu Glu Phe Leu Ser Phe Gly Met Met Leu Cys Ala Leu Leu Phe Leu
                260                 265                 270

Leu Ser Ile Ser Asn Gln Leu Ala Gln Met Ile Met Ile Gly Ser Tyr
        275                 280                 285

Ile Phe Met Ile Leu Ser Gln Met Phe Ala Phe Tyr Trp His Ala Asn
290                 295                 300

Glu Val Leu Glu Ala Ser Leu Gly Ile Gly Asp Ala Ile Tyr Asn Gly
305                 310                 315                 320

Ala Trp Pro Asp Phe Glu Glu Pro Ile Arg Lys Arg Leu Ile Leu Ile
                325                 330                 335

Ile Ala Arg Ala Gln Pro Thr Asp Gly Gly Lys Ile Lys Val Gly Asn
            340                 345                 350

Val Tyr Pro Met Thr Leu Glu Met Phe Gln Lys Leu Leu Asn Val Ser
        355                 360                 365

Tyr Ser Tyr Phe Thr Leu Leu Arg Arg Val Tyr Asn
        370                 375                 380

<210> SEQ ID NO 7
<211> LENGTH: 1236
<212> TYPE: DNA
<213> ORGANISM: Anopheles gambiae

<400> SEQUENCE: 7
atgccttctg agcggcttcg tctcattact tccttcggaa ctcctcaaga caaacgcacg      60
atggtactgc aaaattaaa ggatgaaaca gcagtgatgc cgtttctgct gcaaattcaa     120
accattgccg gactgtgggg tgaccgttcc cagcggtacc gtttttatct catcttttcc     180
tacttctgcg cgatggtggt tctacccaaa gtgctgttcg gttatccaga tctcgaggtt     240
```

-continued

```
gcggtacgcg gcacggccga gctgatgttc gaatcgaacg cattcttcgg catgctaatg    300 tttccttc aacgcgacaa ctacgagcga ttggtgcatc agctgcagga tctggcagct     360
ctagtcctcc aagacctacc cacagagctg gagagtacc tgatctcagt gaaccgacgg    420
gtcgatcggt tctccaaaat ttactgctgc tgtcactttt ccatggcaac gttcttttgg   480
ttcatgcccg tctggacgac ctattccgcc tactttgctg tgcgcaacag cacgaaccg    540 gtcgagcacg tgttgcacct cgaggaagag ctgtacttcc tgaacattcg acttcgatg    600 gcgcactata cgttttatgt ggccattatg tgccccacga tctatacgct cgggtttacc   660
ggtggcacaa agctgctgac cattttcagc aatgttaagt actgttcggc catgctgaag   720
ctcgttgcac tccgaatcca ctgtctagcg agagtagcgc aagaccgagc ggaaaaggag   780
ctgaacgaga ttatttccat gcatcagcgg gtactcaact gcgtgttcct gctggagacg   840
acattccgct gggtattttt cgtgcagttc attcagtgta caatgatctg gtgcagtctc   900
atcctctaca tagcggtgac ggggttcagc tcgacggtag cgaatgtatg tgtccagatc   960
attttggtga cggtggaaac ttacggctac ggctacttcg gaacagatct aaccacggag   1020
gtgctttgga gctatggcgt tgccctcgcc atttacgata gcgagtggta caagttttcc   1080
atttcgatgc gccgcaaact tcgactgcta ctgcaacgat cccaaaaacc gctcggcgta   1140
acggcgggaa agtttcgctt cgtcaatgtg gcccagtttg gcaagatgct caagatgtcc   1200
tattcatttt acgtagtact gaaggagcag ttttag                              1236
```

```
<210> SEQ ID NO 8
<211> LENGTH: 411
<212> TYPE: PRT
<213> ORGANISM: Anopheles gambiae

<400> SEQUENCE: 8

Met Pro Ser Glu Arg Leu Arg Leu Ile Thr Ser Phe Gly Thr Pro Gln
  1               5                  10                  15

Asp Lys Arg Thr Met Val Leu Pro Lys Leu Lys Asp Glu Thr Ala Val
             20                  25                  30

Met Pro Phe Leu Leu Gln Ile Gln Thr Ile Ala Gly Leu Trp Gly Asp
         35                  40                  45

Arg Ser Gln Arg Tyr Arg Phe Tyr Leu Ile Phe Ser Tyr Phe Cys Ala
     50                  55                  60

Met Val Val Leu Pro Lys Val Leu Phe Gly Tyr Pro Asp Leu Glu Val
 65                  70                  75                  80

Ala Val Arg Gly Thr Ala Glu Leu Met Phe Glu Ser Asn Ala Phe Phe
                 85                  90                  95

Gly Met Leu Met Phe Ser Phe Gln Arg Asp Asn Tyr Glu Arg Leu Val
            100                 105                 110

His Gln Leu Gln Asp Leu Ala Ala Leu Val Leu Gln Asp Leu Pro Thr
        115                 120                 125

Glu Leu Gly Glu Tyr Leu Ile Ser Val Asn Arg Arg Val Asp Arg Phe
    130                 135                 140

Ser Lys Ile Tyr Cys Cys Cys His Phe Ser Met Ala Thr Phe Phe Trp
145                 150                 155                 160

Phe Met Pro Val Trp Thr Thr Tyr Ser Ala Tyr Phe Ala Val Arg Asn
                165                 170                 175

Ser Thr Glu Pro Val Glu His Val Leu His Leu Glu Glu Glu Leu Tyr
            180                 185                 190
```

```
Phe Leu Asn Ile Arg Thr Ser Met Ala His Tyr Thr Phe Tyr Val Ala
        195                 200                 205
Ile Met Trp Pro Thr Ile Tyr Thr Leu Gly Phe Thr Gly Gly Thr Lys
    210                 215                 220
Leu Leu Thr Ile Phe Ser Asn Val Lys Tyr Cys Ser Ala Met Leu Lys
225                 230                 235                 240
Leu Val Ala Leu Arg Ile His Cys Leu Ala Arg Val Ala Gln Asp Arg
                245                 250                 255
Ala Glu Lys Glu Leu Asn Glu Ile Ile Ser Met His Gln Arg Val Leu
            260                 265                 270
Asn Cys Val Phe Leu Leu Glu Thr Thr Phe Arg Trp Val Phe Phe Val
        275                 280                 285
Gln Phe Ile Gln Cys Thr Met Ile Trp Cys Ser Leu Ile Leu Tyr Ile
    290                 295                 300
Ala Val Thr Gly Phe Ser Ser Thr Val Ala Asn Val Cys Val Gln Ile
305                 310                 315                 320
Ile Leu Val Thr Val Glu Thr Tyr Gly Tyr Gly Tyr Phe Gly Thr Asp
                325                 330                 335
Leu Thr Thr Glu Val Leu Trp Ser Tyr Gly Val Ala Leu Ala Ile Tyr
            340                 345                 350
Asp Ser Glu Trp Tyr Lys Phe Ser Ile Ser Met Arg Arg Lys Leu Arg
        355                 360                 365
Leu Leu Leu Gln Arg Ser Gln Lys Pro Leu Gly Val Thr Ala Gly Lys
    370                 375                 380
Phe Arg Phe Val Asn Val Ala Gln Phe Gly Lys Met Leu Lys Met Ser
385                 390                 395                 400
Tyr Ser Phe Tyr Val Val Leu Lys Glu Gln Phe
                405                 410

<210> SEQ ID NO 9
<211> LENGTH: 3895
<212> TYPE: DNA
<213> ORGANISM: Anopheles gambiae

<400> SEQUENCE: 9
agctttgttc atttatgttg aaatctagcc cattttgtat agtgctgaac gacgaagaac      60
atacgaaagt acctcgtccg aacactatca acattaatta taccaagcta gaagaagata     120
tttatagtca agcctcaaca tcataggaaa ctttagcaaa accatttaat ttacatgatg     180
ataagtccca cctcttaccc cagcacaggt ttgagaagga cgaaagtatc tttacgataa     240
tattactcta aggtagtttt tgaataaaat aaaaatttac gtgcaagtgg tggcatcgga     300
catcattcga aagaatctac taagtcatac acacacccaa gacgaccgac gtagtttcat     360
ctagaaaaaa cgggtcagct ccatcgaaca cgtcaggaca taactgcgac atgcgtatgg     420
tcagttccac tagtgccaac actggttcca gggcactacc ttccgaagca gtagaaccta     480
atgtattgga aattattagg acatactgca acatgcatat ggctagttcc gctggtacca     540
acgatggcac caggacacta tctgcggcct tgtaaaatca ctgtaaaatc tatacaaaaa     600
cggctttacc catactttat cacaaaaacg gcaggtgagg gctggattgc ttcaaagcat     660
tagaaatata taatttcaaa gtccataatc tccttaaaag atagacaaca gtagagaaca     720
catttagtgc tcttttcgtt cgagttagtt gccttctcaa gtaagcgttt aatgctcaat     780
tgttgtagat tcgttggatg actctcgcta cgtgctatag tggtcaatac ttccaattag     840
atttcataat tagtttccaa ttgtccacgg aaaacccaca aagaaaaaa aaacttgtat      900
```

-continued

```
ctagggtgga attttcgag aacaattgga cacttcatat gaaaaaggac agctttttca    960
aaatgttaaa taaacaccgt tggatccttt gttggatttc aattctccaa attctgcaga   1020
ataattctgc aaattttaca aaactgctca accaccaata attccaatta atcatctgaa   1080
catttaaaac tgataattaa gatgagtaat tgcttcgtca tcacctaaga aatcgattag   1140
tttggataaa agaacaaat tgaaatacaa taaagtccct gaattttatt cgaataacgg    1200
cttgaactca tttatttcaa aaacctttga gaattcctc gttgaaaatt ggtctcctat    1260
agttctgcta acgggccact tcaaaagcaa gaactaacaa atcataatt atggtgcaag    1320
taactatcag taccagtaat cgccattaaa aacttttcct caatttgcgg ctcgttaccg   1380
gctaaataca gagcagagta acgggaagtg atcaacgtcg ctattagtat aacgaggaac   1440
gccctccgaa ggtgtgttga aggacctttt caaattgaaa ccaagtactg tttccagttt   1500
taaattggat agttataaaa tgagccgttc aacgatcggg catcatttga gtttcatctt   1560
cgaggagaaa tagatcagtg ccactgttta accgaaagta atgaagctga acaaactgaa   1620
cccacggtgg gatgcgtacg atcgacggga ttcgttctgg ttgcagttgc tttgtttgaa   1680
atatttaggc ctatggccac cggaagatac ggatcaggca acgcggaacc ggtacatcgc   1740
gtacggttgg gctttgcgga tcatgttct acatctgtac gctctaacgc aagccctata    1800
cttcaaggat gtgaaggata ttaatgtgag tctctagtta gctattagtg ttccacctgt   1860
ccataatctg tctttattg ggtaggacat cgcaaatgca ttgttcgtgc ttatgactca    1920
agtgacgttg atctacaagc tggaaaagtt aactacaaac atcgcacgga ttcaggcttg   1980
tctgcgcaag cttaactgca cactgtatca cccgaaacag cgcgaagaat tcaggtaagc   2040
ctgctgggaa atatgactaa aaagagtgct aacaaacgac tctcctccaa atgtagcccc   2100
gttttacaat cgatgagtgg agtgttttgg ctgatgatct ttctcatgtt tgtggctatc   2160
ttcaccatca tcatgtgggt tatgtcgcca gccttcgaca atgaacgtcg tctgcccgtg   2220
ccggcctggt tcccggtgga ctatcaccat tcggacatag tgtacggtgt actgttcctg   2280
tatcaaacca ttggaatcgt catgagcgca acgtacaact tctcgaccga taccatgttt   2340
tccggcttga tgctacacat aaatggacaa attgtgcggc ttggtagtat ggttaaaaag   2400
gtgagttacg gcgactactt gcctccagta aggacaggga gtttgtttcc gttatgatat   2460
cattttatca gcttggacat gacgtccctc ccgaacgcca attggtcgca acggatgcgg   2520
aatgaaaga gatgcgaaag cgcatcgacc atcactccaa agtgtacggt acgatgtacg   2580
ctaaagtaac ggagtgtgtg ctgtttcaca aggacatctt aaggtacgaa ttgggccaat   2640
taattgtgtc atttaaaaag cttgacccaa cttttcacag cttcggcgat gaagtgcagg   2700
acatttccca aggatctatc ttcgcgcaag tatgcgcgtc tgtaattatc atttgtatga   2760
cactgctgca actaccgggg gcgatgttac gatggccgat ctgctgggct gtggggtcta   2820
tttgctagta aagacatcgc aagtgtttat tttctgttac gtagggaatg aaatctccta   2880
tacggtaggt tggacacgta gaggaattaa atgtttggga agaatatcaa taccaaatag   2940
tatgatgttt cgttacagac ggataaattt acagagtttg ttgggttttc caactacttc   3000
aagttcgata agcgtaccag ccaagcaatg atatttttc tgcaaatgtg agatagcggt    3060
gtatttgtgc agtcagtaca ttaaatacgt tctctatttc aggactctta aagatgttca   3120
catcaaggtg ggaagtgtct tgaaggttac gctaaatctt cacacatttt tgcaggtatg   3180
taattatgct gtggtattta gcttgaaata agctacaaac tttgaaagta atttcaatct   3240
```

-continued

```
gttttgtaga ttatgaagct atcgtactcc tatctggccg tacttcgag catggaatca  3300 gagtaatggt gttaatatcc ttaatgttga aattatattt tgttagattt attgcataaa  3360
gtaatattta atttataca tcaaacgtaa gcccgctagt tttcaattag ccttttccaa   3420
aatttatcaa attgatttcg aattgattgc agagtttcag gaatttaatc tgataggata  3480
tcttgtttat ccaatagagg tgtggaagcg ttcccaagcc attcgtttga tagtttatag  3540
caccgtcgag cagttgatcg ctgtgatcgc taggcgcacc tgattttatc tttatctcgc  3600
acctgttatg gcaagggcgc ttttcacacg tttcacacaa tataatgcac atgtataatg  3660
cattcttact ttagcatttt tgttacatat aataccaaaa ttatgcattt ttattctcac  3720
gcaacgatta gaggatgact tcacaaaggt ccatctagtg gtaggaggta tacaattata  3780
cctctcaaaa tctcacagca taatgagaaa caaaaggata ccaagcatac cctttttta   3840 cttgacaatt tcatttgatt tatgtaataa agcactgcac gtcgacttcc taaaa        3895
```

<210> SEQ ID NO 10
<211> LENGTH: 4985
<212> TYPE: DNA
<213> ORGANISM: Anopheles gambiae

<400> SEQUENCE: 10

```
gggatcctct agagtcgacc tgcaggcatg caagcttccc tcaccgtgac gtgctagaaa    60
tggttcaaca tactcgtccg gcagagcgaa gacgacgaac agcggaatgt cccaggaaat   120
gtaatgagat atcacagcaa gtgaacccaa accgagctgt gcgctttgtg ttgcgcttta   180
aaaatggccc ttccttcgcc gcatctgctt ggtttcacac gctttcccag gaaatccact   240
gaccactggc cacacatcaa ccaccggagc gggagcctca gtgcccagcg aagcatataa   300
tttgctcaaa aagtcacggt actcaattaa tttgattata atcaatttcg tggcttccaa   360
cacacccttc ttccacaatc catcgccgag tgagcgagta aaaggtgaa gaaacgtacc    420 ttgcgcttgc tcactaactg aaccggattt caaaaaggaa cataaaccgc aacccacagc   480
cgaaaatgct gatcgaagag tgtccgataa ttggtgtcaa tgtgcgagtg tggctgttct   540
ggtcgtatct gcggcggccg cggttgtccc gctttctggt cggctgcatc ccggtcgccg   600
tgctgaacgt tttccagttc ctgaagctgt actcgtcctg gggcgacatg agcgagctca   660
tcatcaacgg atactttacc gtgctgtact ttaacctcgt cgtacgtggg cgaggggagg   720
ggcaataacc ttcccacttg gtggatattt tcatacctt tccatgtgtt tttttattct   780
ctgtttgttg ccatccagct ccgaacctcc tttctcgtga tcaatcgacg gaaatttgag   840 acatttttg aaggcgttgc cgccgagtac gctctcctcg aggtaagtca ttggtttttc    900 tagttttttgg gggagttgtt tacaccataa ccaccccga cggtaacatt tgatcgtccc    960
gcgaaaatgt ttgtacagaa aaatgacgac atccgacccg tgctggagcg gtacacacgg  1020
cggggacgca tgctatcgat atcgaatctg tggctcggcg ccttcattag tgcctgcttt  1080
gtgacctatc ctctgtttgt gcccgggcgc ggcctaccgt acggcgtcac gataccgggc  1140
gtggacgtgc tggccacccc gacctaccag gtcgtgtttg tgctgcaggt ttaccttacc  1200
ttccccgcct gctgcatgta catcccgttc accagcttct acgcgacctg cacgctgttt  1260
gcgctcgtcc agatagcggc cctaaagcaa cggctcggac gcttggggcg ccacagcggc  1320
acgatggctt cgaccggaca cagcgccggc acactgttcg ccgagctgaa ggagtgtcta  1380
aagtatcaca acaaatcat ccagtaagta gacgctagta gactcgaccg gattgccctt   1440
ccctcgggga ggggaggttt gctatttcgg gatgcggcag cacgcataca cacaaaccgg  1500
```

-continued

```
aagccattaa ttctcccgtt ttcatgcccg cacgggcact gggtcatgtt tcacatcctt    1560
ccttcctttc caaacacaca cacgcgcgcg tgcacgtaca gatatgttca tgatctcaac    1620
tcactcgtca cccatctgtg tctgctggag ttcctgtcgt tcgggatgat gctgtgcgca    1680
ctgctgtttc tgctaagcat tgtaagtaaa atcgaccgac gtgcggtcgc tagtccgtct    1740
ccggactctc atttcgggac tcaatcgttc catctctcaa tagagcaatc agctggcaca    1800
gatgataatg attggatcgt acatcttcat gatactctcg cagatgtttg ccttctattg    1860
gcatgcgaac gaggtactgg agcaggtaat ggcgctgaag ctgagtttgg ttgagcggtt    1920
cgctatagat cggctgtctt acattgttgt gtttctgcat ggggatcggt tttgtttttc    1980
ctctccattt cagagcctag gcattggcga tgccatttac aatggagcgt ggccggactt    2040
tgaggaaccg ataaggaaac ggttgattct aattattgca cgtgctcagc gaccgatggt    2100
ggtaagtttg gctgatcgat gctctgttca atgaacatgg cacagaaggc tgtgtaaata    2160
gctgttcatt aataagtttt ttcagaatgt atcgttttta gttgatttaa acgcattgtt    2220
ctatgcaatg gtagcaacaa tagaccgcct ttattaatcc aagcttcctt taggattgat    2280
ttttatttta agagaaagat aaaccatttt tagtaaccaa tttagttaca ggaaccaaaa    2340
tacagaattt attattatta ttattattat tattattatt attattatta ttattattat    2400
tattattatt attattatta ttattattat tattataatt attattatta ttattattat    2460
tattattatt attattatta atattattat tattattatt attattacta ttattattat    2520
aattattact tttattatta ttattattat tattattatt attattatta ttattattat    2580
tattattatt attataatta tgattattat tattattatt attattatta ttattattat    2640
aacaataata attattatta ttatttatta ttaattaatt aatttattat tattaattat    2700
tattattgtt attcattatt atacattatt atcataataa taattttatt atgattatta    2760
ttattattat tattattatt attattatta ttattattat tcttattatt attattatta    2820
ttattattat taatattatt tttaatatta ttattattat tattactatt cttattataa    2880 ttatttttt ttattattat tattattatt attattatta ttattattat tattattatt    2940
gctattgtta ttattattct tattattgct attgttatta ttattattct tattattgtt    3000
gttgttgttg ttcttattat tgttgttgtt gttattctta ttattgttta ttattattgt    3060 tttttttttat tctctaatta ttccagtaat ccataataaa aaataataaa gtaaataaat    3120
agtaaatagt aaataattcc agtaactgta gtaatacaca ataatctcta agaattaaaa    3180
ttgcattttg taatgaaata tgttgattgt tcgaatagtt cagaaaaact taaaaatgcc    3240
tcagcattaa acagttttga ggttgttcag ggcatttagt ttagatattt tagtatttta    3300
aagcatttgt tttcattact acaaaaaagc aaatttatga gtgaattact ttcagttctt    3360
ctaaacgcct atgtgtatgc aattacataa caatagctct cttttttatt gcatttttcc    3420
ttagtaatct aaatccaatc tcttctttcc ctcttgcaga ttaaagtcgg caacgtgtac    3480
ccgatgacgt tggaaatgtt tcaaaaattg ctcaacgtgt cctactccta tttcacactg    3540
ctgcgccgag tgtacaacta aacttaaccg gtaaacaaac aaaaatcccc tcatcactat    3600
gcaaagacag caagcagccg atcatcaaac accattagca gccacaaagt taccagccgc    3660
ttatcccacg ggatttggtg gaaagttatt gcactgaagc tctttcaccc aaatttttcat    3720 ggaggttccc tctcaaccaa cccattgaag cgaataaaag tatcagcaac caggcgacgg    3780
tgaaaaaacg ctgcattatt gtgcttgctt cagcattcca gcgaatgact cttaaacttt    3840
```

-continued

```
tccattcaaa agtcgcgatg ctcacgatac ggagcggtgt gttgttcgat ccgccgagtg    3900
cactcgcaag ccggtgatgt tgccggtgga aatgcacaga tcgacacagc gatagataat    3960
cgtttgttcg cgtaaatggg agggaaaaaa gtaagctgcc agctacttca tttccatgtt    4020
aattgaaact caagccaacg aacatgcaga acccggttgg ttgtgtgtct ccgctccggg    4080
aaaggtctct gctccggggc atggattctt tccccctccg ggtggttggg ggtattgttt    4140
aggtttttat tttacaaatt catatccttc cgcttccgca tcagccgacc cggtgggtgc    4200
gccagacaga tgtgcggcgg gcaacaaaac tatgcacgaa catggccaac aaacacagct    4260
tctatctcat ctctgtgtcg cactgtctcg ctttcccgct gcgttgcttg tagtactatc    4320
attgttttag tccacgggtt tacttctaat tccattgcac cacgcaaaaa ggctcatcct    4380
ttgctcgttc cggttgcaac ttcgacaagc gcatggttgg gatacgaaca aaaaccaac    4440
tactccaccc actactacta ctactgccac caccactaac aacactacac ttggttggga    4500
gcttgcagac ccacaagcaa acaacgatac aagctagcta gctgctgtgt gcgctcgagt    4560
cagccgacgg tacaaggttt aaccggtaca agcaactccc ggaccgatcc caaaactctg    4620
acaaggcacg gggccgcatc cggcagtacg gtcggaaaac atggaaatgt ttaattaaaa    4680
ctgtaattgt caatcgctgc tacaagttgt gacacaggga gagagagaga cagagcgcgc    4740
ccgatggtga tggtgtaaaa gatagataca ggaaaagagc gagaaacatt ggtacgattt    4800
ggtgtggtta gcaaatttga tttccactga ttttgagtgc aaatttaatg catcgaaaat    4860
ttgccattca gggtaaagtt gctcgtggac ggatcccccg ggctgcagga attcgatatc    4920
aagcttatcg ataccgtcga cctcgagggg gggcccggta cccagctttt gttccctta    4980
gtgga                                                                4985
```

<210> SEQ ID NO 11
<211> LENGTH: 2083
<212> TYPE: DNA
<213> ORGANISM: Anopheles gambiae

<400> SEQUENCE: 11

```
aagcagaaca catcaagaag caattaggtg tgtcgtacgt tagcaagtag ttcgcgagga      60
ggaataaaat agatgccttc tgagcggctt cgtctcatta cttccttcgg aactcctcaa     120
gacaaacgca cgatggtact gccaaaatta aaggatgaaa cagcagtgat gccgtttctg     180
ctgcaaattc aaaccattgc cggactgtgg ggtgaccgtt cccagcggta ccgtttttat     240
ctcatctttt cctacttctg cgcgatggtg gttctaccca aagtgctgtt cggttatcca     300
gatctcgagg ttgcggtacg cggcacggcc gagctgatgt tcgaatcgaa cgcattcttc     360
ggcatgctaa tgttttcctt tcaacgcgac aactacgagc gattggtgca tcagctgcag     420
gatctggcag ctctaggtga gtatgcagcc aatcgattgt tccaaacctt cgcaacatcc     480
ttcgtaacac tgctacactt tcagtcctcc aagacctacc cacagagctg ggagagtacc     540
tgatctcagt gaaccgacgg gtcgatcggt tctccaaaat ttactgctgc tgtcactttt     600
ccatggcaac gttcttttgg ttcatgcccg ctggacgac ctattccgcc tactttgctg     660
tgcgcaacag cacggaaccg gtcgagcacg tgttgcacct cgaggaagag ctgtacttcc     720
tgaacattcg gacttcgatg gcgcactata cgttttatgt ggccattatg tggcccacga     780
tctatacgct cgggtttacc ggtggcacaa agctgctgac cattttcagc aatgttaagt     840
actgttcggc catgctgaag ctcgttgcac tccgaatcca ctgtctagcg agagtagcgc     900
aagaccgagc ggaaaaggag ctgaacgaga ttatttccat gcatcagcgg gtactcaagt     960
```

-continued

```
aagtaaattc aaattgaaag ttttgcaggg aataacttga gtgtgtctga cccgtgcaca    1020
tcctagctgc gtgttcctgc tggagacgac attccgctgg gtattttcg tgcagttcat    1080 tcagtgtaca atgatctggt gcagtctcat cctctacata gcggtgacgg taatagcatt    1140
ttcgtcattt cgttagcctt attcaatcca tttttgtgaa cgtgaatttc ccccagggt    1200 tcagctcgac ggtagcgaat gtatgtgtcc agatcatttt ggtgacggtg gaaacttacg    1260
gctacggcta cttcggaaca gatctaacca cggaggtgct ttgggtaccc tttggatgaa    1320
gcttcaaaaa gtaattccaa attctgtttt cgattttttcc ccttttccac tagagctatg    1380
gcgttgccct cgccatttac gatagcgagt ggtacaagtt ttccatttcg atgcgccgca    1440
aacttcgact gctactgcaa cgatcccaaa aaccgctcgg cgtaacggcg ggaaagtttc    1500
gcttcgtcaa tgtggcccag tttggcaagg taacattaat tacagtttga aaattctgaa    1560
gaatgcatct tacttgcctt acttgttgtt ccagatgctc aagatgtcct attcatttta    1620
cgtagtactg aaggagcagt tttaggagct gctgtttccc accctggaaa tggccttttc    1680
gcactgtctt ctgtttgttg gacgcacgca gcaccgagag cgcccctgca cgcactgacg    1740
tattttggct actttgacgt ttgcaccttt gacagctgaa ggacagggta caattttttgc    1800 tgctgttatt acgcgcagcg cattggatac gaaaacattg gccacaagtt ctacgatttt    1860
agcgtttatt tactgttcgt agcagctttt ttccacaata aacacacaca ataacgtacc    1920
gacagtattc ttttcattgt aggatagaga agccgccggc cagcagccaa aacgcgccgc    1980
aaaacgaaag gcggcaccac cgggggaaaa acacgggagc aaaacgagaa cagaacgcag    2040
taaacaacaa aaccggccgg aacaacaacg gtgccggaaa cga                      2083
```

<210> SEQ ID NO 12
<211> LENGTH: 2374
<212> TYPE: DNA
<213> ORGANISM: Anopheles gambiae

<400> SEQUENCE: 12

```
ggggaactcc cccacccgac cagacgacgg aaagctaacg atgtgcaatt gaatagtcat     60
tagtagcgtt tttgctcgca aacgaactaa ccctttgact tttttaagttc actacggtga    120 ggacaaaaat caataaatta aatcgagacc gttgatgagc aaaagaaaaa aaatatttt     180 actgattttc atttcgttcc atcgactaca taatcataat tatatgccac attttattat    240 aagttttttgt atcattttta aacaacacaa aaatgcatcc tttcgaatat tagtcaggtt    300
gtatcaacaa tgaagtttga actgttttcaa aaatattcct ccccggacac ggtcttatcc    360
ttcgtgctaa ggcttttgca tatcgtgggc atgaatgggg caggatttcg gtcgcgaatt    420
cgagttggtg gcattttttct gttctatttta atctttcttg taataccgcc actaacgggc    480
gggtacaccg atggtcacca gcgtgtacgc accagtgtgg aattcctgtt taattgcaat    540
atttacggcg gcagtatgtt ctttgcctac gatgtggcca ctttccaagc gttcatccag    600
gaactgaaga gcctttcggt tttgggtaat atttaattaa ttaaaattgc gtttattgca    660
tcatcatttg tttctctttg cagtatgctc acattcgtac agactaaagt ataagctgac    720
ccggttcaac cgtcgagcgg atattatcgc caaagtgcaa acgacctgca tgggtgctgt    780
aacgcttttc tactggattg caccgatacc ttccatctgt gcgcactact acaggtcgac    840
caattccacc gaaccgtgc ggtttgtgca acatttagag gtgaagttct attggctcga    900
gaatcgcacc tcagtcgagg actacataac cttcgtgctg atcatgctac ccgtcgtggt    960
```

```
tatgtgtggt tacgtatgca atttgaaggt gatgaccatc tgctgcagca ttggacactg   1020
tacactgtac accaggatga ctatagagat ggtagagcag ttggaaagca tggcatcagc   1080
ggaacgaact gccagcgcca tacgcaacgt ggggcagatg cacagtggtt tactgaaatg   1140
cattaggctt ttgaacacgt caatccgatc gatgctgatg ctgcagtggt tgacctgcgt   1200
gttaaactgg agcatttctc tcatctatct aacgaacgtg gttagttttg tcttgtttgg   1260
aaatccaaaa acaaaaagat ggctataatt gaactttcta ttacagggca tctcgctaca   1320
atcggttacc gtggtggtaa tgttttttct tgccactgcg gaaactttcc tgtattgttt   1380
acttgggacg cggcttgcga cacaacagca gctgctggag cacgcactct atgctacacg   1440
gtggtacaac tacccaatag cctttcgcag cagcattagg atgatgttga cagtcgca    1500 aaggcatgca cacataacgg tggggaagtt ttttcgcgtt aatttggaag aatttagcag   1560
gattgtcaac ttatcctact ctgcttacgt cgtacttaag gatgtaataa agatggatgt   1620
acagtgaatg ttttttttt tggcttggca acgaatgaag ttttccgaat ctatattaga   1680
tctagaattt aatctagatg tcataatatg atcttggcca tgaccggttc ctggttttgg   1740
aaccaattct caaacaatt ttgaacttag ggcgaggcat gaaatgtccc aagaacctat   1800
ccaagttctg gaactacata ttaccgaatc tatcccatta ttgcctcgga actggtttgg   1860
tgctaaatat ttgtccaaat gttggtcctg gacctatcca gacaaagatc ttcaattatt   1920
cctaccactg gaactgatta attgatgtag gaagtcatgg aggtgttcag ggagaattta   1980
aacactaatg ttccaactca ttatttcaag ggcaattcta ttttttatat gccccctacgg   2040 attgatacgt atgtattact ccatttcctg gactttgtct tattcttgct gctgattgga   2100
cgtgaaatgt tgagaaaaag attcttattt atgagtgata cagagccttt aaatactcct   2160
acgttgtttg ctatttaagt atggccaggc taatcacaat cgctactaat gaacagaatc   2220
tcttctaatt aaacccttc gattgatagt gtcaatgtca atgtcgagat aattgaactg   2280
caaacgatac ctaccttaaa cggagcagaa cacatcaaga agcaattagg tgtgtcgtac   2340
gttagcaagt agttcgcgag gaggaataaa atag                                2374
```

<210> SEQ ID NO 13
<211> LENGTH: 1194
<212> TYPE: DNA
<213> ORGANISM: Anopheles gambiae

<400> SEQUENCE: 13

```
atgaagtttg aactgtttca aaaatattcc tccccggaca cggtcttatc cttcgtgcta    60
aggcttttgc atatcgtggg catgaatggg gcaggatttc ggtcgcgaat tcgagttggt   120 ggcattttc tgttctattt aatctttctt gtaataccgc cactaacggg cgggtacacc   180
gatggtcacc agcgtgtacg caccagtgtg gaattcctgt ttaattgcaa tatttacggc   240
ggcagtatgt tctttgccta cgatgtggcc actttccaag cgttcatcca ggaactgaag   300
agcctttcgg ttttggtatg ctcacattcg tacagactaa agtataagct gacccggttc   360
aaccgtcgag cggatattat cgccaaagtg caaacgacct gcatgggtgc tgtaacgctt   420
ttctactgga ttgcaccgat accttccatc tgtgcgcact actacaggtc gaccaattcc   480
accgaacccg tgcggtttgt gcaacattta gaggtgaagt tctattggct cgagaatcgc   540
acctcagtcg aggactacat aaccttcgtg ctgatcatgc tacccgtcgt ggttatgtgt   600
ggttacgtat gcaatttgaa ggtgatgacc atctgctgca gcattggaca ctgtacactg   660
tacaccagga tgactataga gatggtagag cagttggaaa gcatggcatc agcggaacga   720
```

```
actgccagcg ccatacgcaa cgtggggcag atgcacagtg gtttactgaa atgcattagg     780
cttttgaaca cgtcaatccg atcgatgctg atgctgcagt ggttgacctg cgtgttaaac     840
tggagcattt ctctcatcta tctaacgaac gtgggcatct cgctacaatc ggttaccgtg     900
gtggtaatgt ttttcttgc cactgcggaa actttcctgt attgtttact tgggacgcgg      960
cttgcgacac aacagcagct gctggagcac gcactctatg ctacacggtg gtacaactac    1020
ccaatagcct ttcgcagcag cattaggatg atgttgagac agtcgcaaag gcatgcacac    1080
ataacggtgg ggaagttttt tcgcgttaat ttggaagaat ttagcaggat tgtcaactta    1140
tcctactctg cttacgtcgt acttaaggat gtaataaaga tggatgtaca gtga          1194
```

<210> SEQ ID NO 14
<211> LENGTH: 412
<212> TYPE: PRT
<213> ORGANISM: Anopheles gambiae

<400> SEQUENCE: 14

```
Met Lys Phe Glu Leu Phe Gln Lys Tyr Ser Ser Pro Asp Thr Val Leu
  1               5                  10                  15

Ser Phe Val Leu Arg Leu Leu His Ile Val Gly Met Asn Gly Ala Gly
                 20                  25                  30

Phe Arg Ser Arg Ile Arg Val Gly Gly Ile Phe Leu Phe Tyr Leu Ile
             35                  40                  45

Phe Leu Val Ile Pro Pro Leu Thr Gly Gly Tyr Thr Asp Gly His Gln
         50                  55                  60

Arg Val Arg Thr Ser Val Glu Phe Leu Phe Asn Cys Asn Ile Tyr Gly
 65                  70                  75                  80

Gly Ser Met Phe Phe Ala Tyr Asp Val Ala Thr Phe Gln Ala Phe Ile
                 85                  90                  95

Gln Glu Leu Lys Ser Leu Ser Val Leu Val Cys Ser His Ser Tyr Arg
            100                 105                 110

Leu Lys Tyr Lys Leu Thr Arg Phe Asn Arg Arg Ala Asp Ile Ile Ala
        115                 120                 125

Lys Val Gln Thr Thr Cys Met Gly Ala Val Thr Leu Phe Tyr Trp Ile
    130                 135                 140

Ala Pro Ile Pro Ser Ile Cys Ala His Tyr Tyr Arg Ser Thr Asn Ser
145                 150                 155                 160

Thr Glu Pro Val Arg Phe Val Gln His Leu Glu Val Lys Phe Tyr Trp
                165                 170                 175

Leu Glu Asn Arg Thr Ser Val Glu Asp Tyr Ile Thr Phe Val Leu Ile
            180                 185                 190

Met Leu Pro Val Val Met Cys Gly Tyr Val Cys Asn Leu Lys Val
        195                 200                 205

Met Thr Ile Cys Cys Ser Ile Gly His Cys Thr Leu Tyr Thr Arg Met
    210                 215                 220

Thr Ile Glu Met Val Glu Gln Leu Glu Ser Met Ala Ser Ala Glu Arg
225                 230                 235                 240

Thr Ala Ser Ala Ile Arg Asn Val Gly Gln Met His Ser Gly Leu Leu
                245                 250                 255

Lys Cys Ile Arg Leu Leu Asn Thr Ser Ile Arg Ser Met Leu Met Leu
            260                 265                 270

Gln Trp Leu Thr Cys Val Leu Asn Trp Ser Ile Ser Leu Ile Tyr Leu
        275                 280                 285
```

```
Thr Asn Val Gly Ile Ser Leu Gln Ser Val Thr Val Val Met Phe
    290                 295                 300

Phe Leu Ala Thr Ala Glu Thr Phe Leu Tyr Cys Leu Leu Gly Thr Arg
305                 310                 315                 320

Leu Ala Thr Gln Gln Gln Leu Leu Glu His Ala Leu Tyr Ala Thr Arg
                325                 330                 335

Trp Tyr Asn Tyr Pro Ile Ala Phe Arg Ser Ser Ile Arg Met Met Leu
            340                 345                 350

Arg Gln Ser Gln Arg His Ala His Ile Thr Val Gly Lys Phe Phe Arg
                355                 360                 365

Val Asn Leu Glu Glu Phe Ser Arg Ile Val Asn Leu Ser Tyr Ser Ala
    370                 375                 380

Tyr Val Leu Lys Asp Val Ile Lys Met Asp Val Gln Asn Val Ser
385                 390                 395                 400

Tyr Ser Tyr Phe Thr Leu Leu Arg Arg Val Tyr Asn
                405                 410
```

<210> SEQ ID NO 15
<211> LENGTH: 1176
<212> TYPE: DNA
<213> ORGANISM: Anopheles gambiae

<400> SEQUENCE: 15

```
atggtgctac cgaagctgtc cgaaccgtac gccgtgatgc cgcttctact acgcctgcag      60
cgtttcgttg gctgtggggg tgaacgacgc tatcgctaca agttccggtt ggcattttta     120
agcttctgtc tgctagtagt tattccgaag gttgccttcg gctatccaga tttagagaca     180
atggttcgcg gaacagctga gctgattttc gaatggaacg tactgtttgg gatgttgctg     240
ttttctctca gctagacga ctatgatgat ctggtgtacc ggtacaagga catatcaaag     300
attgctttcc gtaaggacgt tccctcgcag atgggcgact atctggtacg catcaatcat     360
cgtatcgatc ggttttccaa gatctactgc tgcagccatc tgtgtttggc catcttctac     420
tgggtggctc cttcgtccag cacctaccta gcgtacctgg gggcacgaaa cagatccgtc     480
ccggtcgaac atgtgctaca cctggaggag gagctgtact ggtttcacac ccgcgtctcg     540
ctggtagatt actccatatt caccgccatc atgctgccta caatctttat gctagcgtac     600
ttcggtggac taaagctgct aaccatcttc agcaacgtga agtactgttc ggcaatgctc     660
aggcttgtgg cgatgagaat ccagttcatg gaccggctgg acgagcgcga agcggaaaag     720
gaactgatcg aaatcatcgt catgcatcag aaggcgctaa aatgtgtgga gctgttggaa     780
atcatctttc ggtgggtttt tctgggacag ttcatacagt gcgtaatgat ctggtgcagc     840
ttggttctgt acgtcgccgt tacgggtctc agcacaaaag cggcaaacgt gggtgtactg     900
tttatactgc taacagtgga aacctacgga ttctgctact ttggcagtga tcttacctcg     960
gaggcaagtt gttattcgct gacacgtgct gcgtacggta gcctctggta tcgccgttcg    1020
gtttcgattc aacggaagct tcgaatggta ctgcagcgtg cccagaaacc ggtcggcatc    1080
tcggctggga gttttgcttt cgtcgacatt gagcagtttg gcaatatggc aaaaacatca    1140
tactcgttct acatcgttct gaaggatcaa ttttaa                              1176
```

<210> SEQ ID NO 16
<211> LENGTH: 391
<212> TYPE: PRT
<213> ORGANISM: Anopheles gambiae

<400> SEQUENCE: 16

```
Met Val Leu Pro Lys Leu Ser Glu Pro Tyr Ala Val Met Pro Leu Leu
 1               5                  10                  15

Leu Arg Leu Gln Arg Phe Val Gly Leu Trp Glu Arg Arg Tyr Arg
             20                  25                  30

Tyr Lys Phe Arg Leu Ala Phe Leu Ser Phe Cys Leu Leu Val Val Ile
             35                  40                  45

Pro Lys Val Ala Phe Gly Tyr Pro Asp Leu Glu Thr Met Val Arg Gly
         50                  55                  60

Thr Ala Glu Leu Ile Phe Glu Trp Asn Val Leu Phe Gly Met Leu Leu
 65                  70                  75                  80

Phe Ser Leu Lys Leu Asp Asp Tyr Asp Asp Leu Val Tyr Arg Tyr Lys
                 85                  90                  95

Asp Ile Ser Lys Ile Ala Phe Arg Lys Asp Val Pro Ser Gln Met Gly
             100                 105                 110

Asp Tyr Leu Val Arg Ile Asn His Arg Ile Asp Arg Phe Ser Lys Ile
         115                 120                 125

Tyr Cys Cys Ser His Leu Cys Leu Ala Ile Phe Tyr Trp Val Ala Pro
130                 135                 140

Ser Ser Ser Thr Tyr Leu Ala Tyr Leu Gly Ala Arg Asn Arg Ser Val
145                 150                 155                 160

Pro Val Glu His Val Leu His Leu Glu Glu Leu Tyr Trp Phe His
                 165                 170                 175

Thr Arg Val Ser Leu Val Asp Tyr Ser Ile Phe Thr Ala Ile Met Leu
                 180                 185                 190

Pro Thr Ile Phe Met Leu Ala Tyr Phe Gly Gly Leu Lys Leu Leu Thr
             195                 200                 205

Ile Phe Ser Asn Val Lys Tyr Cys Ser Ala Met Leu Arg Leu Val Ala
         210                 215                 220

Met Arg Ile Gln Phe Met Asp Arg Leu Asp Glu Arg Glu Ala Glu Lys
225                 230                 235                 240

Glu Leu Ile Glu Ile Ile Val Met His Gln Lys Ala Leu Lys Cys Val
                 245                 250                 255

Glu Leu Leu Glu Ile Ile Phe Arg Trp Val Phe Leu Gly Gln Phe Ile
             260                 265                 270

Gln Cys Val Met Ile Trp Cys Ser Leu Val Leu Tyr Val Ala Val Thr
         275                 280                 285

Gly Leu Ser Thr Lys Ala Ala Asn Val Gly Val Leu Phe Ile Leu Leu
         290                 295                 300

Thr Val Glu Thr Tyr Gly Phe Cys Tyr Phe Gly Ser Asp Leu Thr Ser
305                 310                 315                 320

Glu Ala Ser Cys Tyr Ser Leu Thr Arg Ala Ala Tyr Gly Ser Leu Trp
                 325                 330                 335

Tyr Arg Arg Ser Val Ser Ile Gln Arg Lys Leu Arg Met Val Leu Gln
             340                 345                 350

Arg Ala Gln Lys Pro Val Gly Ile Ser Ala Gly Lys Phe Cys Phe Val
         355                 360                 365

Asp Ile Glu Gln Phe Gly Asn Met Ala Lys Thr Ser Tyr Ser Phe Tyr
         370                 375                 380

Ile Val Leu Lys Asp Gln Phe
385                 390

<210> SEQ ID NO 17
<211> LENGTH: 474
```

-continued

```
<212> TYPE: DNA
<213> ORGANISM: Anopheles gambiae

<400> SEQUENCE: 17
ttatgcttac cggatgttgc gatcgcgcac gtgcttttcc gcatacgcca gtgcacactt    60
gatggcggtg gtgatgacgt ctgctgcgca ccgttttctg ctcgtgagtc agacctttc   120 atttcctgca atatcctgtt tctttcccga ccccacagac ggttagacgg atatatgctg   180
gtaaagtttg tcctcttcat gctgtgcttt ctgatcgagc tgctgatgct gtgtgcgtac   240
ggtgaggata ttgtggaatc gccttgggt gattgatgcc gcttacggtt gcgaatggta    300
ccgggaaggg tcggtggcgt tccatcgatc cgtgctgcaa attatacacc gcagccagca   360
gtccgtcata ctgaccgcat ggaaaatttg gcccatccaa atgagtactt tcagtcagat   420
cctgcaagct tcctggtcct actttaccct cctgaagacc gtctacggga ataa         474

<210> SEQ ID NO 18
<211> LENGTH: 157
<212> TYPE: PRT
<213> ORGANISM: Anopheles gambiae

<400> SEQUENCE: 18
```

Leu Cys Leu Pro Asp Val Ala Ile Ala His Val Leu Phe Arg Ile Arg
 1               5                  10                  15

Gln Cys Thr Leu Asp Gly Gly Asp Asp Val Cys Cys Ala Pro Phe
            20                  25                  30

Ser Ala Arg Glu Ser Asp Leu Phe Ile Ser Cys Asn Ile Leu Phe Leu
        35                  40                  45

Ser Arg Pro His Arg Arg Leu Asp Gly Tyr Met Leu Val Lys Phe Val
    50                  55                  60

Leu Phe Met Leu Cys Phe Leu Ile Glu Leu Leu Met Leu Cys Ala Tyr
65                  70                  75                  80

Gly Glu Asp Ile Val Glu Ser Pro Trp Gly Asp Glx Cys Arg Leu Arg
                85                  90                  95

Leu Arg Met Val Pro Gly Arg Val Gly Gly Val Pro Ser Ile Arg Ala
            100                 105                 110

Ala Asn Tyr Thr Pro Gln Pro Ala Val Arg His Thr Asp Arg Met Glu
        115                 120                 125

Asn Leu Ala His Pro Asn Glu Tyr Phe Gln Ser Asp Pro Ala Ser Phe
    130                 135                 140

Leu Val Leu Leu Tyr Pro Pro Glu Asp Arg Leu Arg Glu
145                 150                 155

```
<210> SEQ ID NO 19
<211> LENGTH: 1206
<212> TYPE: DNA
<213> ORGANISM: Anopheles gambiae

<400> SEQUENCE: 19
atggtgctga tccagttctt cgccatcctc ggcaacctgg cgacgaacgc ggacgacgtg    60
aacgagctga ccgccaacac gatcacgacc ctgttcttca cgcactcggt caccaagttc   120
atctactttg cggtcaactc ggagaacttc taccggacgc tcgccatctg gaaccagacc   180
aacacgcacc cgctgttttgc cgaatcggac gcccggtacc attcgattgc gctcgccaag   240
atgcggaagc tgctggtgct ggtgatggcc accaccgtcc tgtcggttgt cgcctgggtt   300
acgataacat ttttcggcga gagcgtcaag actgtgctcg ataaggcaac caacgagacg   360
```

-continued

```
tacacggtgg atataccccg gctgcccatc aagtcctggt atccgtggaa tgcaatgagc    420
ggaccggcgt acattttctc tttcatctac caggtacgtt ggcggaatgg tattatgcga    480
tcgttgatgg agctttcggc ctcgctggac acctaccggc ccaactcttc gcaactgttc    540
cgagcaattt cagccggttc caaatcggag ctgatcatca acgaagaaaa ggatccggac    600
gttaaggact tgatctgag cggcatctac agctcgaagg cggactgggg cgcccagttc     660
cgtgcgccgt cgacgctgca aacgttcgac gagaatggcg ggaacggaaa tccgaacggg    720
cttacccgga agcaggaaat gatggtgcgc agcgccatca agtactgggt cgagcggcac    780
aagcacgttg tacgtctcgt ttcagcaatc ggagatacgc acggtcctgc cctgctgcta    840
cacatgctga cctccaccat caagctgacg ctgctcgcct accaggcaac gaaaatcgac    900
ggtgtcaacg tgtacggatt gaccgtaatc ggatatttgt gctacgcgtt ggctcaggtt    960
ttcctgtttt gcatctttgg caatcggctc atcgaggaga gctcatccgt gatgaaggcg    1020
gcctattcct gccactggta cgacgggtcc gaggaggcaa aaaccttcgt ccagatcgtt    1080
tgtcagcagt gccagaaggc gatgactatt ccggagcca agttttcac cgtttcgctc      1140 gatctgtttg cttcggttct tggagccgtt gtcacctact tcatggtgct ggtgcagctg    1200
aagtaa                                                                1206
```

```
<210> SEQ ID NO 20
<211> LENGTH: 401
<212> TYPE: PRT
<213> ORGANISM: Anopheles gambiae

<400> SEQUENCE: 20
```

```
Met Val Leu Ile Gln Phe Phe Ala Ile Leu Gly Asn Leu Ala Thr Asn
  1               5                  10                  15

Ala Asp Asp Val Asn Glu Leu Thr Ala Asn Thr Ile Thr Thr Leu Phe
             20                  25                  30

Phe Thr His Ser Val Thr Lys Phe Ile Tyr Phe Ala Val Asn Ser Glu
         35                  40                  45

Asn Phe Tyr Arg Thr Leu Ala Ile Trp Asn Gln Thr Asn Thr His Pro
     50                  55                  60

Leu Phe Ala Glu Ser Asp Ala Arg Tyr His Ser Ile Ala Leu Ala Lys
 65                  70                  75                  80

Met Arg Lys Leu Leu Val Leu Val Met Ala Thr Thr Val Leu Ser Val
                 85                  90                  95

Val Ala Trp Val Thr Ile Thr Phe Phe Gly Glu Ser Val Lys Thr Val
            100                 105                 110

Leu Asp Lys Ala Thr Asn Glu Thr Tyr Thr Val Asp Ile Pro Arg Leu
        115                 120                 125

Pro Ile Lys Ser Trp Tyr Pro Trp Asn Ala Met Ser Gly Pro Ala Tyr
    130                 135                 140

Ile Phe Ser Phe Ile Tyr Gln Val Arg Trp Arg Asn Gly Ile Met Arg
145                 150                 155                 160

Ser Leu Met Glu Leu Ser Ala Ser Leu Asp Thr Tyr Arg Pro Asn Ser
                165                 170                 175

Ser Gln Leu Phe Arg Ala Ile Ser Ala Gly Ser Lys Ser Glu Leu Ile
            180                 185                 190

Ile Asn Glu Glu Lys Asp Pro Asp Val Lys Asp Phe Asp Leu Ser Gly
        195                 200                 205

Ile Tyr Ser Ser Lys Ala Asp Trp Gly Ala Gln Phe Arg Ala Pro Ser
    210                 215                 220
```

```
Thr Leu Gln Thr Phe Asp Glu Asn Gly Arg Asn Gly Asn Pro Asn Gly
225                 230                 235                 240

Leu Thr Arg Lys Gln Glu Met Met Val Arg Ser Ala Ile Lys Tyr Trp
            245                 250                 255

Val Glu Arg His Lys His Val Val Arg Leu Val Ser Ala Ile Gly Asp
            260                 265                 270

Thr Tyr Gly Pro Ala Leu Leu Leu His Met Leu Thr Ser Thr Ile Lys
            275                 280                 285

Leu Thr Leu Leu Ala Tyr Gln Ala Thr Lys Ile Asp Gly Val Asn Val
    290                 295                 300

Tyr Gly Leu Thr Val Ile Gly Tyr Leu Cys Tyr Ala Leu Ala Gln Val
305                 310                 315                 320

Phe Leu Phe Cys Ile Phe Gly Asn Arg Leu Ile Glu Glu Ser Ser Ser
                325                 330                 335

Val Met Lys Ala Ala Tyr Ser Cys His Trp Tyr Asp Gly Ser Glu Glu
            340                 345                 350

Ala Lys Thr Phe Val Gln Ile Val Cys Gln Gln Cys Gln Lys Ala Met
            355                 360                 365

Thr Ile Ser Gly Ala Lys Phe Phe Thr Val Ser Leu Asp Leu Phe Ala
    370                 375                 380

Ser Val Leu Gly Ala Val Val Thr Tyr Phe Met Val Leu Val Gln Leu
385                 390                 395                 400

Lys
```

<210> SEQ ID NO 21
<211> LENGTH: 2272
<212> TYPE: DNA
<213> ORGANISM: Anopheles gambiae

<400> SEQUENCE: 21

```
tctagacttg aacccatgac gggcatttta ttgagtcgtt cgagttgacg actgtaccac      60
gggaccaccc gttatcact atcactatta attaattata atatgctttt gtagcgatca     120
gcctaccggg ttttgtttct ctggatatct taagttccca tttgattatc aagatagaac     180
aacaacttgt accttaaata atcattacgt acccttaatc aacctgtgca tcaaggagtt     240
ttcgcgaaag caaaaatccg attgtctgat gttgtcttga ttccatccga ttcgttactg     300
gttctgcaaa tcgtccaat aatacggcaa tgtccttatc gatgcttgaa tcaacatcac     360
attgtttgca tttcgttttt tgcgtgcaaa tatgttattt gcaaagaagg caagtaatg     420
tgcttaagag taaatacaat tcgctgtcca tttttgtcc accagtgtgc cagaacccgt     480
gccttttagt ccttcgaata catccgacca gtcagcaagc aagtgcatca tggtgctacc     540
gaagctgtcc gaaccgtacg ccgtgatgcc gcttctacta cgcctgcagc gtttcgttgg     600
gctgtggggt gaacgacgct atcgctacaa gttccggttg gcattttaa gcttctgtct     660
gctagtagtt attccgaagg ttgccttcgg ctatccagat ttagagacaa tggttcgcgg     720
aacagctgag ctgattttcg aatggaacgt actgtttggg atgttgctgt tttctctcaa     780
gctagacgac tatgatgatc tggtgtaccg gtacaaggac atatcaaaga ttggtgcgtg     840
ataatgattg ataaaggaa cctttgagca actcctatcc ctttcaagct ttccgtaagg     900
acgttccctc gcagatgggc gactatctgg tacgcatcaa tcatcgtatc gatcggtttt     960
ccaagatcta ctgctgcagc catctgtgtt tggccatctt ctactgggtg gctccttcgt    1020
ccagcaccta cctagcgtac ctgggggcac gaaacagatc cgtcccggtc gaacatgtgc    1080
```

-continued

```
tacacctgga ggaggagctg tactggtttc acacccgcgt ctcgctggta gattactcca    1140
tattcaccgc catcatgctg cctacaatct ttatgctagc gtacttcggt ggactaaagc    1200
tgctaaccat cttcagcaac gtgaagtact gttcggcaat gctcaggctt gtggcgatga    1260
gaatccagtt catggaccgg ctggacgagc gcgaagcgga aaaggaactg atcgaaatca    1320
tcgtcatgca tcagaaggcg ctaaagtaag gtctgccggt atgttgtgga tagaatacat    1380
ttctagctgc tttcagatgt gtggagctgt tggaaatcat cttccggtgg gtttttctgg    1440
gacagttcat acagtgcgta atgatctggt gcagcttggt tctgtacgtc gccgttacgg    1500
taactaaaag cactgtagtg atctgtctgc cacaccattc actgctgtgt cttgttttgt    1560
cactcttccc agggtctcag cacaaaagcg caaacgtgg gtgtactgtt tatactgcta    1620
acagtggaaa cctacggatt ctgctacttt ggcagtgatc ttacctcgga ggcaagttgt    1680
tattcgctga gtttcagtta cttttccgtt cccctctaac cgtaccactt gtaccatttg    1740
tttgagacag agcttgagcg tagcacgtgc tgcgtacggt agcctctggt atcgccgttc    1800
ggtttcgatt caacggaagc ttcgaatggt actgcagcgt gcccagaaac cggtcggcat    1860
ctcggctggg aagttttgct tcgtcgacat tgagcagttt ggcaatgtat ggggagacct    1920
tccactgtgg caagaaagat tttctttatt aatgcatctt ttaatttaca gatggcaaaa    1980
acatcatact cgttctacat cgttctgaag gatcaatttt aaagggaac tccccaccc     2040 gaccagacga cggaaagcta acgatgtgca attgaatagt cattagtagc gttttttgctc    2100 gcaaacgaac taacccttg acttttaag ttcactacgg tgaggacaaa aatcaataaa      2160
ttaaatcgag accgttgatg agcaaaagaa aaaaaatat tttactgatt ttcatttcgt     2220
tccatcgact acataatcat aattatatgc cacattttat tataagtttt tg            2272
```

<210> SEQ ID NO 22
<211> LENGTH: 931
<212> TYPE: DNA
<213> ORGANISM: Anopheles gambiae

<400> SEQUENCE: 22

```
aacacccatc ttatcggcaa aattagtatt taccgtttga aagcggcttc ccttcctggc     60
tgtttctcac tctctctctc tctgtctctc ttattgatgc cgtatgcgcc gcgtgctata    120
ggctagttat gcttaccgga tgttgcgatc gcgcacgtgc ttttccgcat acgccagtgc    180
acacttgatg gcggtggtga tgacgtctgc tgcgcaccgt tttctgctcg tgagtcagac    240
cttttcattt cctgcaatat cctgtttctt tcccgacccc acagacggtt agacggatat    300
atgctggtaa agtttgtcct cttcatgctg tgctttctga tcgagctgct gatgctgtgt    360
gcgtacggtg aggatattgt ggaatcggta aggcaccagg cggtgatgag cgagtcgcga    420
gtaattgaag ctttttgcttt taaaacacat cagagccttg gggtgattga tgccgcttac    480
ggttgcgaat ggtaccggga agggtcggtg gcgttccatc gatccgtgct gcaaattata    540
caccgcagcc agcagtccgt catactgacc gcatggaaaa tttggcccat ccaaatgagt    600
actttcagtc aggtgagttg ccaattgatt gccgtttgcg ttaatatttc agtaagagtg    660 cgctcttttcc cttagatcct gcaagcttcc tggtcctact ttaccctcct gaagaccgtc    720
tacgggaata agtaagcgcg agagagagag agagagcagt atcgttcacc ctttggatga    780
atcaatagat ttctaatcat gaaccattga aaaatgaatc aacattttcg ctagttgcac    840
aatattgtac cattctatac agcttcacca cgaccaagcg tttgttgcat caggaccaaa    900
```

```
cacgtttcga caagccgcgt cacctgctgg c                          931
```

<210> SEQ ID NO 23
<211> LENGTH: 11103
<212> TYPE: DNA
<213> ORGANISM: Anopheles gambiae

<400> SEQUENCE: 23

```
ccgcccgggc aggtgactta cgcggtctga cttgctggtg cgctgctttg tacggcaaac    60
ggctacacaa gcgaatcgaa ttattttcct atcacgctgc gcttaccagc gcctgctggt   120
aggcaaagaa tgtgcaaagt ttcatttggc ttggttcgtc tgctttgctg tgaacgtgtg   180
cacggttgca tcgctaaggt ttcggtgtga gccgagaagt tgcagatcga aatctctttg   240
tgtgtgtgtg tgtgtgtgca gtgggaagca ttgtgtttag tgagaagtga aaagaaaagt   300
gctgaaaaat gcaagtccag ccgaccaagt acgtcggcct tcgttgccga cctgatgccg   360
aacattcggg ttgatgcagg ccagcggtca actttctgtt ccggctacgt caccggcccg   420
atactgatcc gcaaggtgta ctcctggtgg acgctcgccc atggtgctga tccagttctt   480
cgccatcctc ggcaacctgg cgacgaacgc ggacgacgtg aacgagctga ccgccaacac   540
gatcacgacc ctgttcttca cgcactcggt caccaagttc atctactttg cggtcaactc   600
ggagaacttc taccggacgc tcgccatctg gaaccagacc aacacgcacc cgctgtttgc   660
cgaatcggac gcccggtacc attcgattgc gctcgccaag atgcggaagc tgctggtgct   720
ggtgatggcc accaccgtcc tgtcggttgt cggtatgtgt gtatgtgtgt ggccgtttgg   780
gaaagtgtct ttgcggcaga accccaatct actgttacgc ttgactgggt ttttgttttt   840
ttctcggtgg agggacggga taaaatatct gaaagaataa ttgagtcaac ccacaggggg   900
atgcaagaca tcgcaggcag agagtttggg tttgatttat caccgcacac cgaatatctt   960
cacggttcat aagcttcacc gcggtgaaaa gggaactccc catttccctg ttttctttttt  1020
tttcttcctc tcgataaatt actcatcgct tttcgttttt tttttttgt tgttgcttct   1080
ttcttctttc atccctacta gcctgggtta cgataacatt tttcggcgag agcgtcaaga  1140
ctgtgctcga taaggcaacc aacgagacgt acacggtgga tataccccgg ctgcccatca  1200
agtcctggta tccgtggaat gcaatgagcg gaccggcgta catttctct ttcatctacc  1260
aggtacgttg gcggaatgtc ctgcgcgtca cagttggcag tcagtgagcg gcaacacggc  1320
gaaaaaatgg gactaaaacc ggtcttcaca gagccaacac attcctacag caattgcata  1380
ccttcgggcg gtcgggactg ggcaatgcag ctacaacatc ctcgcctaaa gttatgcaat  1440
tcgagcgaca aatgttgccg tgttagggct ttttgtgata atagtcgttt ttttgtcctc  1500
tcgcttatca aactctatca acggaggaaa tccattttcg ctacaatgcc tacagctcaa  1560
gtttcaaggt caatcgagcg ggtgggatc aactttttta ttcattttgc taacgcccca  1620
tcaacaaatt ctatgttctc aatggcaaag attactgccc gcaccaatcg cccaacgaaa  1680
cggcaaaaga aaagcgacga ttatgaagat gtccaaacca ttgcccgccc gacgctttat  1740
ctgatgattt gcgggatggc ttttacttgt ctgctacttt caggcacaaa aggaaatgaa  1800
accagcgcag gctcgtttgc cggcttgcgg aggttcttca ggcactgagg ctgagtactt  1860
aaatcgaacg atttttacga ttctggatcc agttttatga tgtggcctgc attacagtgg  1920
caattatacc ctgatgttca tttcattgca ttttgtaagt ttgtgctggt aacgcccgta  1980
acgattaatt cttttcaaag agattctttc aaagagattc aaaatgtgta taacaaatgc  2040
taacgaatgg accgtacttg gagggttgcg gaaagtaacg ttttaaaata ttcatcacaa  2100
```

-continued

```
tcctctgcaa acttgtgctt aattaattgg tgcacaataa gtttaaactg tggcggcaga    2160
tgtgtcgctg tccgcttcct tccttcccag caagctcgtg cgaaataatt tattccatca    2220
ttttaataca gccgtttgtg cattttaatt agcaaagcaa tataaaaagc agctaaccat    2280
ccccattaaa acaaagtgct tccgggccca attgttatgg cggtggaaag taatggtttt    2340
accagtggaa gtgtcctttc ccatcgtggg tacttcgcga tattcttgtc ttatacaagt    2400
gcatacagaa aaaaggaca atcctcctt gctatggtct aaggccagct tcggtaccgc      2460
ttccgcttcg ggatgtcata aagtttgatg ggtgttttta acattacttc cgctcttaac    2520
cacctaatgg acttttcatg cttgagctaa agttaaacca gccaccagcg gtacgcaccg    2580
agccacggtt gatttcggcg gcggcctcat ccccagtttt gcgccaccaa tattgccttc    2640
attaatctgt accctcggag cgttagggcc cgcggacgag tcctcgttgt aatgcaccgc    2700
catgccacgg gacgggataa tccgttggga cggcgcgaaa gcgactatcg cggacggatt    2760
ggttcgaccg tgctacaaca catttatgc ttcacagatt tacttcctgc tgttttcgat     2820
ggtccagagc aacctcgcgg atgtcatgtt ctgctcctgg ttgctgctag cctgcgagca    2880
gctgcaacac ttgaaggtag gtacggtagc aaacgtggtt gtctttacat ccgcgtgcag    2940
cattatcctt atcgacgtgt agtgttaacg gtaaaagagg aagcgataaa aaagcaacat    3000
tctctcacac cctcgatctc tctttatttt ctctctctct ctctctctct ctctctctct    3060
ctctctctct ctctctctct ctctccatct cctcgggcag ggtattatgc gatcgttgat    3120
ggagctttcg gcctcgctgg acacctaccg gcccaactct tcgcaactgt tccgagcaat    3180
ttcagccggt tccaaatcgg agctgatcat caacgaaggt atgtgaaacg tgtgctcgtg    3240
gcagacggac tcaaagagag cataacacaa tcccctggta gttcatttca atgacctaa    3300
cactcggcaa gctaagcgag acagtgggga cagtgagaaa gagagaacaa gaaaaaaaac    3360
catcatccgt acgacatcat cgctacgtac cggtatttca ggatgaggaa ataaaacgct    3420
aggggaatga aagtgcgaca gaatgataaa acaatcccca cccaggcccc cagcctggac    3480
gaacggatgt agtgtgcgaa gcgagcaaaa aaagtcaaat aaattgaagt ttaaaaatag    3540
attttccccg tccatccgtg gtggagcgta aagcccggcg gacaacttcg agcacggcga    3600
ccgtgcacag tactgtgcca cagttgtagg gacggataag ctccgttcct tttttatcct    3660
ttttttttgg agatttgttt gcgttcgcat cgttagacga gcttagtgcc gtgttgctct    3720
aattgctatt tattataaag cgcttccaaa tagaagatcg gttctctcca tttaatctat    3780
cgcgcctgta cgcctgaaac tatgcactgt gctgtgaaac cgtcaagctc gagcacgacg    3840
aatgccccac cgtaccacgc ccgtggtgcc caaagcgcaa cgcgaattgc atgttaacaa    3900
acctttgcct accatccaat ccgtgtgaaa ttgcccgctc tctttctctc ttttgcgctt    3960
tcggtgtatc gaacggtttt gtcccttttt tttactttgc tcttgatctc ttgctgtgct    4020
cactttcatc tcatgttttg cctgacggtg gtgggttttc gaaaaagag cgatttcttc     4080
tgcgtgtgtg tgtggttttt ttaaataacc gctccaggtc gtgttgaacg ctgcaggacc    4140
gatcggagct agtttattat cagctttagt gtttatccca cccatgcccc acatcacgtc    4200
tgtggagagt gggggaagct taagtccaat gtaatttacc gtgtttctgt cgttcgtcac    4260
cttcttcgtc gatggagatt ggtgcggttg gcacgataaa agcccactgc acgttacgga    4320
ccgagggaaa ggtctttttg taggcctagc aacggtcctc attcaccgca tgggggtgta    4380
gctcagatgg tagagcgctc gcttagcatg tgagaggtac cggatcgat acccggcatc     4440
```

```
tccaacccac acaaaacgtt tttttaagaag attttttaggg aagatattaa cgcgggtaca   4500
ctgtgctcct ctaagttgga agagtagatg agatgatgac aagggagaag gaacatgtgt   4560
acgtgtttga tagcaaacac acaaacaaca atatcatctc tgataataat ctgatgtgtg   4620
atgtgtgtgt attgttgtta tgctgccttt gccatcttgt ccctctctct cctgttcaac   4680
tcctaaaaga attgtttgga gtcctctcag ttcctcgtaa agatcctttc gagattcttc   4740
tttccttttt attatttatt ccacgagcct ctgacataag tagccttccg cttatttcct   4800
tctccttgca cttgtcagtt ccgtgtagag cgtcattttg aggtttacac atttcccacc   4860
gacgcctgat tgttacattg tcatctacat tgctttccgt ttaccgttcc gccctttttt   4920
tttaacgcta ccacagaaaa ggatccggac gttaaggact ttgatctgag cggcatctac   4980
agctcgaagg cggactgggg cgcccagttc cgtgcgccgt cgacgctgca aacgttcgac   5040
gagaatggca ggaacggaaa tccgaacggg cttacccgga agcaggaaat gatggtgcgc   5100
agcgccatca agtactgggt cgagcggcac aagcacgttg tacggtaggt atggtaattt   5160
ctaaggtgtg gtgtaaagcc tccaggttcc atgaaaaagg gatactttac cacagtaaga   5220
gtttgttttg ctggacttac attctttgga gcattgtttg gtgttgtgct gaaaccggtt   5280
gcaatatcgt tttgcgaaga aattatgtgt aaagcgtatt acaatctcat tcctctgtta   5340
atctgtacca attgtgtcag ccccgaccga aagcaggcct aattcgtacc agaaaaacca   5400
caagctgttt gtaagcatcg atacgcccga agctttcaat ccagccaagg cgccacctac   5460
tattgacgtg acttttttgca cgttcacact ctccctctcc cattctttct ataaccaatc   5520
gtcgctcagc cagcatcgcc cggagtgaag ttttttatttg aacgatatca cccgtatcga   5580
ttttccacta aacatgctta aatcgtttca caaagctccc ccaaaatccc atttcaccaa   5640
tccaccaatt tgaagtccgt cgtcctttgt gtccttgtgt ttgtgtgttt gtgtgagctg   5700
gagacatggg ggagtgagta accgaacaac ctcttgccgc tgcttcacga tatcgaacag   5760
caccaagata agcatcccct ttttccctagc cgatgtctcc gatatctcga ttccgcttcc   5820
agcgaggcaa agaaaaaggc gaactggctg acctcacccg gggcgaggaa aaagcgtagg   5880
gattacgtcg agcagcacga gttgtgattt cttcttcttc tggttccata aatcgctgac   5940
ggtttccatt accgcctgcg gagtgcacac acgtgaaggg aaagcgaaaa cgtttagatt   6000
ccagcagcaa cggcagcacc agaagcagca gcagcgcggc aaattgaatc atcctgacgc   6060
gatgagttgt ctgggttttc gggtcggtgg cttacagcac cacaccatct gctgcagcta   6120
atacagctgt aaatttcgtt agacatagac ttgattttac aatattacac acacacttac   6180
acacacagct atagatttgt cgcttggcgt atggctctgt acggcgtgcc gtacatgccg   6240
cgagccgtgt tgctgctggt tgcgatacgg atcacgtccg attcgattca gcctgcgtgt   6300
ttttggtgaa gatccttatc ggtgacccac tttcagtgtg tcgagagcga gggtcactat   6360
ggcgcctgtc agttggaaag ctaggctcga ttcaaagggc cattgtgcca gtgttctttt   6420
taagatagcg ataagctttt gatcgaaata gtaaatcaaa cattgtttct ttttttcctat   6480 tccaaactgt tgccaacctc attattacgt ttttgcagcg ggtgtatagt aaattgcata   6540
ctttaaggcg tgattttcaa atgtagcgtt ccgtatgcag aaacgccatg gattatgcaa   6600
tttaaacaat gctgcttcct taacattcaa ataacggctt attaaggaac ttttttgtgca   6660 atttgttttt aacagcaaat agttagctca gaacgatcac atttagtatc gcttcaacaa   6720
agaactcttt taaacacaca atttgtaatg ccattccctc gagaaagttt cttgtcagtc   6780
ctcctctgca tcacagcaac aaccaaacct gctcatgttt cctgctcgtt tcctagctgt   6840
```

-continued

```
tttgaacgtt atttccgatt cctgtgcttg cccgcttttc ttacaatcaa ccacaatggt    6900
tcagatttcg ctcttatttt attgacccac tgctttcgtg ctgaagcccg tggaaacaat    6960
gcgccaagct cagcatccag ccatgcatgt aaaatgagcc acgcgacaga ttttagacat    7020
cgctttcgct ctgcaccgga ggtggtttta ttcttgtttc cgattcccac gtccattcgt    7080
cctgggtccg tccgccgggc ccgaaaccgt aagccgtgcg gggaattacg caatcgaaac    7140
gagccagaaa atgagcacgc caaatgcaaa gaaaatcccc ttttgagtgg tgctcctgcc    7200
accactcatc tccccaactg gtgggtgaaa accttgtgc gccccttctc tttccagaaa     7260
aaaaacgcct cgctcgcaca aaaacatgct cgcccggtga agctgcgtat gtcgcagaag    7320
ctcaaaccaa cgccgccagc aagcatcaac aatttctatt caaacaccca acgcagcgcc    7380
caaaccgggt gcactgtact cagtagcgaa gatgctcaga ttgtcccgtg cgctgctttc    7440
gatgcccgtt tcggagcggg aagccatcgc ttgccaacgt tggcgatgtc ttttagccgt    7500
ggatttgaat tttctgaata tcacaggcgg gcgcggtttg cctgcaaggt tgttgcttcc    7560
cacacgagca ttgctttccg taccgcggtg gggcgagttt tcaacgcaac cttctacaag    7620
caacgccaca acgcctggga gcgatattta acagaaacaa gaacatcccg aacttcagca    7680
catgccgtga tttgcctgtt ggaaaagctt ttgtgagcgt gtgagttgaa cgagctctat    7740
tttcccagcg atgggtggca tttgtgtggc atgctatcgt cagcttttct tgaatcttta    7800
cctctccatt cgcctccatt agtacacgcg tatggaaaat gggtgcaacg gatcagaacg    7860
gattttccgc gacagactta ataaagggaa agcaacgcgt ttttttgcatg tgtagtgttt    7920
atgagcttta tgccgttact ttgcaattaa aaatagcaaa aataacagt tttttttttgt     7980
aagcggatta caaagaatgt atcagaatat acgtgaaac attcatttca tgctgttaac     8040
gctcaaatag aatagttttg taacacggat tgcataccctt gccggtatcg gttacatttt    8100
cgcctaacag tatgcaatct gtttagcttt gttgtttaat gactgcgttg gtagtacaat    8160
atttattttac accgcgtaat ttatctcaca aattgcaaaa aaatgtcaat ctgtatcgat    8220
tattcacaca aatcagatcc cggaaccagt gtagcccaat gtgctcttat tgaattacca    8280
cgaacaaatc aacctgatgc ccgggtccgt tggcaaacag cttgcgccga agccgctcag    8340
tgtttcgtgc actaccgtgc tgccattttg ctgccctcat cgaacagata aacagaaggg    8400
caactcttgt gagcatcgca atgcccgtct gaagttccgt cgaaaatggg cctaaattca    8460
atttgacgca tttacccgcg aacaattgcg cgaaggctgt caagtgtgtt ccacgaactg    8520
cgacaacaag cacacacaca aacacaaatg ttatcgtttc ggcatgtttc tcggtacaaa    8580
gcgtgtggcg ctatgtggca tgccgattcc cagacagagt gatcgatagt aaatgtagcc    8640
tatccggtag cattcaattt ccttttctat cctcgcaaac aaagcccatt ctggggaggc    8700
gtggtgaagc tttcaaaggc attgtgaaac aaatgtcctg gttcggaggg atgctgggga    8760
aagcaaacac ggtgccgcca tcgctgctac cgtcaatcga tcatgcatga tgtgattaat    8820
atttgtgtta ttcacctgcg tatctatgcg tccgtcgtgt cgttcggatt ccggaagtc     8880
aaggaaaaag cgactccatt tgggattggt ttttgcagcg aaaaatcaaa acattcgcac    8940
aaaccgtcc tccatttcaa atgcctacac ttgtcactgt atatctctct ttctctcgtt     9000
ttgccacgtt gcagtctcgt ttcagcaatc ggagatacgt acggtcctgc cctgctgcta    9060
cacatgctga cctccaccat caagctgacg ctgctcgcct accaggcaac gaaaatcgac    9120
ggtgtcaacg tgtacggatt gaccgtaatc ggatatttgt gctacgcgtt ggctcaggtt    9180
```

-continued

```
ttcctgtttt gcatctttgg caatcggctc atcgaggagg tacgtgcgct cggcgtgttg    9240
ccgtgggaaa gcattctccc tgccccatat cgcttcattc tcccagatca cacatttgca    9300
tcacaaagcc agcacacttt tgcttcgccg ctgccatctc ggcttctgaa tgttttcact    9360
tctcccatac ttctcccgtg cagagctcat ccgtgatgaa ggcggcctat tcctgccact    9420
ggtacgacgg gtccgaggag gcaaaaacct tcgtccagat cgtttgtcag cagtgccaga    9480
aggcgatgac tatttccgga gccaagtttt tcaccgtttc gctcgatctg tttgcttcgg    9540
taagtgtagc ctggtggctg gcacagaaca ggctggcaaa acagggactt tggctctagc    9600
ctgatgggtg gtatatgtgt gtctattttt tgctaccatt ctcgcatccc ttcctttcca    9660
ggttcttgga gccgttgtca cctacttcat ggtgctggtg cagctgaagt aaacagccgt    9720
ggcccggaag gatgtgtttt ttttcgctcg ttcggttgtt tgtttgtgca cactttctct    9780
tggacatttt ctctactgca aaggtttaac aaacagcaac aacaaataat cccaagtttt    9840
cttttacaga tctttgcaaa atgattagat tttaatagat taacagtgct tgattatctg    9900
tcctgtagca accggggctg aagaacgttg atttggtaaa agtacaaaag ggacgttgga    9960
aattgaacca ccagaagagt gatatttatg caaagctcac caagggaaat ctatgtatgt   10020
gtgatttgcg ctcatcaagc actgtatgtg cctttcaact agtgcagcaa taaagagtac   10080
aaatgtttct tagcgcaccg tacattgtcg tttcggcgtt ttaaccgttg ttgataatac   10140
acaaaagatg ataaaaataa ataataacaa aatgttaata tgagtaagta ctaaatagag   10200
aaatcgtttt agtatgatca tacctccaat catttgtttg aaattaactt taattttaac   10260
tcaaattaaa ccgatgtttt actttctgtg agaattattg tggaagaact taatggaagt   10320
ataattaaat tgattgctaa ctttatgcgt ttttcaattt acgaacgcta gtcttcaaac   10380
atcgcttcaa aagtattact accacattat tcatttactt atagttatat ttattgcctc   10440
ttcatctttc catggccaga actactgcag aaaagcttct ttttgctcg ctttccgatg    10500
gttggttgga cgaagttggt aacaaacggc aagcaattag cataaactat tttcgcatcg   10560
agatggaaat gaatgtacca ctagaaccga gtgaaatgaa ttacttttca acttgcacgc   10620
caaaaccatt atctaaagta cgcacaactt aaaaacaaac cccaaattgt cgtccaccct   10680
tcattccact ttcttgctac actttccgac cgagttctgt agcgccagca gcaaaaaaat   10740
acatataaaa ccttcatcac tcaagctgta tcgagccagc gtgggttgtg tttgactgtg   10800
ctgtgaaaga aagaagaaaa aaaaaacact tccacgggaa gctagcaatt ggaaatgcat   10860
aaattaaccg gaagaaattc gcaaaacccc gcaccgacgt accgcaccgc atccgtaccg   10920
ataccggaac aaacggtgtg cgcgaaagaa tccgctagca gccccactgg cacgggtatt   10980
tgcttttggt tctgtgtttt tcttccactg gtttgggtgc ctgggcgaag gctagctcgg   11040
ctactttccc ggggccgcaa ttttctgcag cccaaggcgg cgtgctcgtg gggccaaaag   11100
aat                                                                11103
```

MOSQUITO ARRESTIN 1 POLYPEPTIDES

This application claims benefit of co-pending U.S. patent application Ser. No. 60/264,649 filed Jan. 26, 2001, entitled "Mosquito Olfactory Genes, Polypeptides, and Methods of Use Thereof" which is hereby incorporated by reference. Be it known that I, Laurence J Zwiebel, a citizen of the United States, residing at 2512 Sunset Place, Nashville, Tenn. 37212; have invented a new and useful "Mosquito Arrestin 1 Polypeptide".

GOVERNMENT SUPPORT CLAUSE

This invention was made with federal grant money under NIH grant 1 R01 DC04692-01 and NSF grant 0075338. The United States Government has certain rights in this invention.

A Portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates generally to the field of host identification by insects. Specifically, the present invention relates to the identification and cloning of genes related to mosquito olfaction, identification and purification of polypeptides thereof, and methods of use thereof.

BACKGROUND OF THE INVENTION

The ability of an insect to respond to chemical stimuli is necessary for the insect to reproduce, mate, and feed. For example, insects respond to certain chemical stimuli by moving up a chemical gradient to identify and target a host. Mosquitoes, in particular, are believed to use olfaction to identify and target sources of bloodmeal for reproductive purposes. This behavior contributes to the spread of diseases in humans, such as malaria, encephalitis, and dengue fever; as well as, animal and livestock disease.

Olfaction plays a critical role in insect behaviors among agricultural pests and disease vectors. Hildebrand, et al., 1997, Annu. Rev. Neurosci, 20:595–631. In *Drosophila melanogaster* (the common fruit fly), the olfactory system functions through a rapid cycling between an on and off state of certain regulatory molecules. The olfactory signal transduction cascade is "turned on" by ligand-based activation of an odorant receptor and transduction of the signal by G-protein coupled second messenger pathways Boekhoff et al., 1994, J. Neurosci, 14:3304–9. The "on signal" is rapidly and substantially terminated in the *Drosophila* system through the modification of the odorant receptor such that the G-protein coupled second messenger pathway is deactivated. Dohlman et al., 1991, Annual Review of Biochemistry, 60:653–88. Olfactory transduction is provided by second messenger pathways of G protein-coupled receptors. Reed, R., 1992, Neuron 8:205–209; Bloekhoff, et al, 1994, Neurosci 14:3304–3309.

The structural and functional characteristics of the mosquito olfactory system has not been characterized to date. Given the importance of the controlling this pest and disease vector, what is needed is the identification and characterization of the genes and polypeptides that function for mosquito olfaction and methods of use thereof for mosquito management.

SUMMARY OF THE INVENTION

The present invention provides, in part, eight novel mosquito polypeptides and nucleic acids encoding the polypeptides (collectively referred to herein as "mosquito olfaction molecules"). Seven of the polypeptides are novel mosquito odorant receptors and the eighth is a novel mosquito arrestin molecule (see FIG. 8). The odorant receptor molecules are discovered to function in a ligand-induced signal transduction pathway for the activation of mosquito olfaction. The mosquito arrestin molecule is discovered to function to inhibit the activated signal transduction cascade. Thus, the odorant receptors can be viewed as parts of an "on switch" or an "on signal" and the arrestin molecule can be viewed as an "off switch" or an "off signal" for the odorant detection system of the mosquito. The present invention is not bound by theory or mechanism.

The present invention also provides, in part, a system for disrupting the mosquito olfactory system by disrupting, inhibiting, or otherwise interfering with the function of the off switch for mosquito olfaction. Such interference is contemplated to inhibit or degrade the ability of the mosquito to appropriately respond to chemical clues in the environment used by the mosquito for host identification and targeting. For, example, if the signal cascade cannot be terminated or inhibited, then the mosquito is impaired in following a chemical gradient to a host through sampling of the frequency of ligand-induced activation of the olfaction signal cascade. In this example, the chemical concentration of the odorant is expected to increase with decreasing distance to the target. Thus, receptor activation is expected to increase with decreasing distance to the target. It is a discovery of the present invention, that factors that inhibit the on and off cycling of the mosquito olfactory signal cascade through inhibition of signal deactivation are useful for the control of mosquitoes. Test agents used in a method for identifying mosquito olfaction molecule binding compounds would include, but are not limited to: chemicals, proteins, peptides, organic compounds and lipids. Such factors that inhibit signal deactivation may be peptides and chemicals. Several classes of chemicals that would be selected as targets are the carboxylic acids and steroids that are components of human sweat. Cork, A. (1996). Olfactory sensing is the basis of host location by mosquitoes and other hematophagous Diptera. In Olfaction in Mosquito-Host Interactions, G. R. B. a. G. Cardew, ed. (Chichester, N.Y., Brisbane, Toronto, Singapor: John Wiley & Sons), pp. 71–84. Furthermore, certain aspects of the present invention are contemplated to be effective for insects in general.

Methods are presented for identifying compounds that interfere with the operation of the mosquito olfactory system resulting in an over stimulation of olfactory signaling. One consequence of interfering with the mosquito olfactory system is that the mosquito has a diminished ability to home in on sources of bloodmeal. Additionally, interfering with mosquito insect olfactory systems will inhibit mating and feeding having a significant impact on mosquito populations and is helpful, for example, in nuisance and disease vector control for humans and livestock. Interfering with non-mosquito insect olfaction will similarly have a positive impact in control of other insect populations including for the protection of crops, such as: wheat, corn, rice, cotton, and soybeans. Thus, certain aspects of the present invention provide screening assays for the identification of compositions that will reduce the ability of mosquitoes to locate sources of bloodmeal, such as humans and other mammals, including livestock (cattle, pigs, horses, sheep, etc.), show animals (horses, pigs, sheep, dogs, cats, etc.), and pets (dogs, cats, horses, etc). Certain aspects of the present invention provide a screening assay for the production of "mosquito olfaction molecules."

One aspect of the present invention provides an isolated DNA comprising a nucleotide sequence that encodes arrestin 1 polypeptide (e.g., SEQ ID NO: 2). In certain embodiments, arrestin 1 nucleotide sequence comprises a DNA molecule that hybridizes under stringent conditions to a DNA having a nucleotide sequence consisting of SEQ ID NO: 1, or the complement of SEQ ID NO: 1. Preferably the isolated DNA encodes naturally-occurring *Anopheles gambiae* arrestin 1 polypeptides. In certain embodiments, the nucleotide sequence may be that of SEQ ID NO: 1. In alternate embodiments, the nucleotide sequence may encode a fragment of SEQ ID NO: 2 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 2. In certain embodiments, the isolated polynucleotide comprises a complement to a sequence that encodes a polypeptide having an amino acid sequence selected from the group consisting of SEQ ID NO: 2, and conservatively modified SEQ ID NO: 2. In alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention also provides an isolated DNA comprising a nucleotide sequence that encodes odorant receptor 1 polypeptide (e.g., SEQ ID NO: 4). In certain embodiments, odorant receptor 1 nucleotide sequence comprises a DNA molecule that hybridizes under stringent conditions to a DNA having a nucleotide sequence consisting of SEQ ID NO: 3, or the complement of SEQ ID NO: 3. Preferably the isolated DNA encodes naturally-occurring *Anopheles gambiae* odorant receptor 1 polypeptides. In certain embodiments, the nucleotide sequence may be that of SEQ ID NO: 3. In alternate embodiments, the nucleotide sequence may encode a fragment of SEQ ID NO: 4 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 4. In certain embodiments, the isolated polynucleotide comprises a complement to a sequence that encodes a polypeptide having an amino acid sequence selected from the group consisting of SEQ ID NO: 4, and conservatively modified SEQ ID NO: 4. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention provides an isolated DNA comprising a nucleotide sequence that encodes odorant receptor 2 polypeptide (e.g., SEQ ID NO: 6). In certain embodiments, odorant receptor 2 nucleotide sequence comprises a DNA molecule that hybridizes under stringent conditions to a DNA having a nucleotide sequence consisting of SEQ ID NO: 5, or the complement of SEQ ID NO: 5. Preferably the isolated DNA encodes naturally-occurring *Anopheles gambiae* odorant receptor 2 polypeptides. In certain embodiments, the nucleotide sequence may be that of SEQ ID NO: 5. In alternate embodiments, the nucleotide sequence may encode a fragment of SEQ ID NO: 6 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 6. In certain embodiments, the isolated polynucleotide comprises a complement to a sequence that encodes a polypeptide having an amino acid sequence selected from the group consisting of SEQ ID NO: 6, and conservatively modified SEQ ID NO: 6. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention also provides an isolated DNA comprising a nucleotide sequence that encodes odorant receptor 3 polypeptide (e.g., SEQ ID NO: 8). In certain embodiments, odorant receptor 3 nucleotide sequence comprises a DNA molecule that hybridizes under stringent conditions to a DNA having a nucleotide sequence consisting of SEQ ID NO: 7, or the complement of SEQ ID NO: 7. Preferably the isolated DNA encodes naturally-occurring *Anopheles gambiae* odorant receptor 3 polypeptides. In certain embodiments, the nucleotide sequence may be that of SEQ ID NO: 7. In alternate embodiments, the nucleotide sequence may encode a fragment of SEQ ID NO: 8 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 8. In certain embodiments, the isolated polynucleotide comprises a complement to a sequence that encodes a polypeptide having an amino acid sequence selected from the group consisting of SEQ ID NO: 8, and conservatively modified SEQ ID NO: 8. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention also provides an isolated DNA comprising a nucleotide sequence that encodes odorant receptor 4 polypeptide (e.g., SEQ ID NO: 14). In certain embodiments, odorant receptor 4 nucleotide sequence comprises a DNA molecule that hybridizes under stringent conditions to a DNA having a nucleotide sequence consisting of SEQ ID NO: 13, or the complement of SEQ ID NO: 13. Preferably the isolated DNA encodes naturally-occurring

*Anopheles gambiae* odorant receptor 4 polypeptides. In certain embodiments, the nucleotide sequence may be that of SEQ ID NO: 13. In alternate embodiments, the nucleotide sequence may encode a fragment of SEQ ID NO: 14 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 14. In certain embodiments, the isolated polynucleotide comprises a complement to a sequence that encodes a polypeptide having an amino acid sequence selected from the group consisting of SEQ ID NO: 14, and conservatively modified SEQ ID NO: 14. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention also provides an isolated DNA comprising a nucleotide sequence that encodes odorant receptor 5 polypeptide (e.g., SEQ ID NO: 16). In certain embodiments, odorant receptor 5 nucleotide sequence comprises a DNA molecule that hybridizes under stringent conditions to a DNA having a nucleotide sequence consisting of SEQ ID NO: 15, or the complement of SEQ ID NO: 15. Preferably the isolated DNA encodes naturally-occurring *Anopheles gambiae* odorant receptor 5 polypeptides. In certain embodiments, the nucleotide sequence may be that of SEQ ID NO: 15. In alternate embodiments, the nucleotide sequence may encode a fragment of SEQ ID NO: 16 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 16. In certain embodiments, the isolated polynucleotide comprises a complement to a sequence that encodes a polypeptide having an amino acid sequence selected from the group consisting of SEQ ID NO: 16, and conservatively modified SEQ ID NO: 16. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention also provides an isolated DNA comprising a nucleotide sequence that encodes odorant receptor 6 polypeptide (e.g., SEQ ID NO: 18). In certain embodiments, odorant receptor 6 nucleotide sequence comprises a DNA molecule that hybridizes under stringent conditions to a DNA having a nucleotide sequence consisting of SEQ ID NO: 17, or the complement of SEQ ID NO: 17. Preferably the isolated DNA encodes naturally-occurring *Anopheles gambiae* odorant receptor 6 polypeptides. In certain embodiments, the nucleotide sequence may be that of SEQ ID NO: 17. In alternate embodiments, the nucleotide sequence may encode a fragment of SEQ ID NO: 18 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 18. In certain embodiments, the isolated polynucleotide comprises a complement to a sequence that encodes a polypeptide having an amino acid sequence selected from the group consisting of SEQ ID NO: 18, and conservatively modified SEQ ID NO: 18. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention also provides an isolated DNA comprising a nucleotide sequence that encodes odorant receptor 7 polypeptide (e.g., SEQ ID NO: 20). In certain embodiments, odorant receptor 7 nucleotide sequence comprises a DNA molecule that hybridizes under stringent conditions to a DNA having a nucleotide sequence consisting of SEQ ID NO: 19, or the complement of SEQ ID NO: 19. Preferably the isolated DNA encodes naturally-occurring *Anopheles gambiae* odorant receptor 7 polypeptides. In certain embodiments, the nucleotide sequence may be that of SEQ ID NO: 19. In alternate embodiments, the nucleotide sequence may encode a fragment of SEQ ID NO: 20 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 20. In certain embodiments, the isolated polynucleotide comprises a complement to a sequence that encodes a polypeptide having an amino acid sequence selected from the group consisting of SEQ ID NO: 20, and conservatively modified SEQ ID NO: 20. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention provides a substantially pure arrestin 1 polypeptide that includes amino acid sequence that contains at least a conservatively modified identity with SEQ ID NO: 2 and binds to odorant receptors. The amino acid sequence of arrestin 1 protein can differ from SEQ ID NO: 2 by non-conservative substitutions, deletions, or insertions located at positions that do not destroy the function of the arrestin 1 polypeptide. In alternate embodiments, the polypeptide has an amino acid sequence consisting of SEQ ID NO: 2. The purified polypeptide is a polypeptide that binds specifically to an antibody that binds specifically to mosquito arrestin. In other alternate embodiments, the polypeptide comprises fragments of SEQ ID NO: 2, having at least 20 consecutive residues.

The present invention also provides a substantially pure odorant receptor 1 polypeptide that includes amino acid sequence that contains at least a conservatively modified identity with SEQ ID NO: 4 and binds to arrestin. The amino acid sequence of odorant receptor 1 polypeptide can differ from SEQ ID NO: 4 by non-conservative substitutions, deletions, or insertions located at positions that do not destroy the function of the odorant receptor 1 polypeptide.

In alternate embodiments, the polypeptide has an amino acid sequence consisting of SEQ ID NO: 4. In other alternate embodiments, the polypeptide comprises fragments of SEQ ID NO: 4, having at least 20 consecutive residues.

The present invention provides a substantially pure odorant receptor 2 polypeptide that includes amino acid sequence that contains at least a conservatively modified identity with SEQ ID NO: 6 and binds to arrestin. The amino acid sequence of odorant receptor 2 polypeptide can differ from SEQ ID NO: 6 by non-conservative substitutions, deletions, or insertions located at positions that do not destroy the function of the odorant receptor 2 polypeptide. In alternate embodiments, the polypeptide has an amino acid sequence consisting of SEQ ID NO: 6. In other alternate embodiments, the polypeptide comprises fragments of SEQ ID NO: 6, having at least 20 consecutive residues.

The present invention also provides a substantially pure odorant receptor 3 polypeptide that includes amino acid sequence that contains at least a conservatively modified identity with SEQ ID NO: 8 and binds to arrestin. The amino acid sequence of odorant receptor 3 polypeptide can differ from SEQ ID NO: 8 by non-conservative substitutions, deletions, or insertions located at positions that do not destroy the function of the odorant receptor 3 polypeptide. In alternate embodiments, the polypeptide has an amino acid sequence consisting of SEQ ID NO: 8. In other alternate embodiments, the polypeptide comprises fragments of SEQ ID NO: 8, having at least 20 consecutive residues.

The present invention also provides a substantially pure odorant receptor 4 polypeptide that includes amino acid sequence that contains at least a conservatively modified identity with SEQ ID NO: 14 and binds to arrestin. The amino acid sequence of odorant receptor 4 polypeptide can differ from SEQ ID NO: 14 by non-conservative substitutions, deletions, or insertions located at positions that do not destroy the function of the odorant receptor 4 polypeptide. In alternate embodiments, the polypeptide has an amino acid sequence consisting of SEQ ID NO: 14. In other alternate embodiments, the polypeptide comprises fragments of SEQ ID NO: 14, having at least 20 consecutive residues.

The present invention also provides a substantially pure odorant receptor 5 polypeptide that includes amino acid sequence that contains at least a conservatively modified identity with SEQ ID NO: 16 and binds to arrestin. The amino acid sequence of odorant receptor 5 polypeptide can differ from SEQ ID NO: 16 by non-conservative substitutions, deletions, or insertions located at positions that do not destroy the function of the odorant receptor 5 polypeptide. In alternate embodiments, the polypeptide has an amino acid sequence consisting of SEQ ID NO: 16. In other alternate embodiments, the polypeptide comprises fragments of SEQ ID NO: 16, having at least 20 consecutive residues.

The present invention also provides a substantially pure odorant receptor 6 polypeptide that includes amino acid sequence that contains at least a conservatively modified identity with SEQ ID NO: 18 and binds to arrestin. The amino acid sequence of odorant receptor 6 polypeptide can differ from SEQ ID NO: 18 by non-conservative substitutions, deletions, or insertions located at positions that do not destroy the function of the odorant receptor 6 polypeptide. In alternate embodiments, the polypeptide has an amino acid sequence consisting of SEQ ID NO: 18. In other alternate embodiments, the polypeptide comprises fragments of SEQ ID NO: 18, having at least 20 consecutive residues.

The present invention also provides a substantially pure odorant receptor 7 polypeptide that includes amino acid sequence that contains at least a conservatively modified identity with SEQ ID NO: 20 and binds to arrestin. The amino acid sequence of odorant receptor 7 polypeptide can differ from SEQ ID NO: 20 by non-conservative substitutions, deletions, or insertions located at positions that do not destroy the function of the odorant receptor 7 polypeptide. In alternate embodiments, the polypeptide has an amino acid sequence consisting of SEQ ID NO: 20. In other alternate embodiments, the polypeptide comprises fragments of SEQ ID NO: 20, having at least 20 consecutive residues.

The invention also provides an arrestin 1 antibody, which comprises polyclonal or monoclonal antibodies. The antibody can be conjugated to a detectable label.

Another aspect of the present invention provides an odorant receptor 1 antibody, which comprises polyclonal or monoclonal antibodies. The antibody can be conjugated to a detectable label. Antibody labels and methods are well known in the art.

The present invention also provides an odorant receptor 2 antibody, which comprises polyclonal or monoclonal antibodies. The antibody can be conjugated to a detectable label.

Another aspect of the present invention provides an odorant receptor 3 antibody, which comprises polyclonal or monoclonal antibodies. The antibody can be conjugated to a detectable label.

Another aspect of the present invention provides an odorant receptor 4 antibody, which comprises polyclonal or monoclonal antibodies. The antibody can be conjugated to a detectable label.

Another aspect of the present invention provides an odorant receptor 5 antibody, which comprises polyclonal or monoclonal antibodies. The antibody can be conjugated to a detectable label.

Another aspect of the present invention provides an odorant receptor 6 antibody, which comprises polyclonal or monoclonal antibodies. The antibody can be conjugated to a detectable label.

Another aspect of the present invention provides an odorant receptor 7 antibody, which comprises polyclonal or monoclonal antibodies. The antibody can be conjugated to a detectable label.

The present invention also presents a method of producing arrestin 1 protein. The method includes the following steps: (a) providing a cell transformed with an isolated DNA comprising a nucleotide sequence that encodes an amino acid sequence of SEQ ID NO: 2; (b) culturing the cell; and (c) collecting from the cell or the medium of the cell the polypeptide encoded by the polynucleotide sequence. Certain alternatives to SEQ ID NO: 2 are described above (e.g. conservative variants and hybridization variants).

The present invention also provides a method of manufacturing odorant receptor 1 protein. The method includes the following steps: (a) providing a cell transformed with an isolated DNA comprising a nucleotide sequence that encodes an amino acid sequence of SEQ ID NO: 4; (b) culturing the cell; and (c) collecting from the cell or the medium of the cell the polypeptide encoded by the polynucleotide sequence.

The present invention provides a method of manufacturing odorant receptor 2 protein. The method includes the following steps: (a) providing a cell transformed with an isolated DNA comprising a nucleotide sequence that encodes an amino acid sequence of SEQ ID NO: 6; (b) culturing the cell; and (c) collecting from the cell or the medium of the cell the polypeptide encoded by the polynucleotide sequence.

The present invention also provides a method of manufacturing odorant receptor 3 protein. The method includes the following steps: (a) providing a cell transformed with an isolated DNA comprising a nucleotide sequence that encodes an amino acid sequence of SEQ ID NO: 8; (b) culturing the cell; and (c) collecting from the cell or the medium of the cell the polypeptide encoded by the polynucleotide sequence.

The present invention also provides a method of manufacturing odorant receptor 4 protein. The method includes the following steps: (a) providing a cell transformed with an isolated DNA comprising a nucleotide sequence that encodes an amino acid sequence of SEQ ID NO: 14; (b) culturing the cell; and (c) collecting from the cell or the medium of the cell the polypeptide encoded by the polynucleotide sequence.

The present invention also provides a method of manufacturing odorant receptor 5 protein. The method includes the following steps: (a) providing a cell transformed with an isolated DNA comprising a nucleotide sequence that encodes an amino acid sequence of SEQ ID NO: 16; (b) culturing the cell; and (c) collecting from the cell or the medium of the cell the polypeptide encoded by the polynucleotide sequence.

The present invention also provides a method of manufacturing odorant receptor 6 protein. The method includes the following steps: (a) providing a cell transformed with an isolated DNA comprising a nucleotide sequence that encodes an amino acid sequence of SEQ ID NO: 18; (b) culturing the cell; and (c) collecting from the cell or the medium of the cell the polypeptide encoded by the polynucleotide sequence.

The present invention also provides a method of manufacturing odorant receptor 7 protein. The method includes the following steps: (a) providing a cell transformed with an isolated DNA comprising a nucleotide sequence that encodes an amino acid sequence of SEQ ID NO: 20; (b) culturing the cell; and (c) collecting from the cell or the medium of the cell the polypeptide encoded by the polynucleotide sequence.

The present invention also provides a method for identifying a mosquito olfaction molecule binding compound. The method includes the following steps: (a) providing an isolated mosquito olfaction molecule; (b) contacting a test agent with the isolated mosquito olfaction molecule; and (c) detecting whether the test agent is bound to the isolated mosquito olfaction molecule. Methods of detection are well known in the art. In certain embodiments, the isolated mosquito olfaction molecule further comprises a polypeptide having an amino acid sequence as set forth in SEQ ID NO: 2 or variants thereof as described herein (As used herein this statement means conservatively modified variants, hybridization variants, and variants to which antibodies bind specifically). In alternate embodiments, the isolated mosquito olfaction molecule further comprises a polypeptide having an amino acid sequence selected from the group consisting of SEQ ID NO: 2, SEQ ID NO. 4, SEQ ID NO. 6, SEQ ID NO. 8, SEQ ID NO. 14, SEQ ID NO. 16, SEQ ID NO. 18, SEQ ID NO. 20. conservatively modified SEQ ID NO: 4, conservatively modified SEQ ID NO: 6, conservatively modified SEQ ID NO: 8, conservatively modified SEQ ID NO: 14, conservatively modified SEQ ID NO: 16, conservatively modified SEQ ID NO: 18, and conservatively modified SEQ ID NO: 20. In other embodiments, contacting the test agent with the isolated mosquito olfaction molecule further comprises contacting under native conditions. In alternate embodiments, detecting specific binding of the test agent to the isolated mosquito olfaction molecule further comprises immunoprecipitation.

The present invention also presents a screening method for identifying a compound that inhibits binding of mosquito arrestin to a mosquito odorant receptor. The method includes the following steps: (a) providing an antibody that binds to an isolated mosquito olfaction molecule; (b) providing a mosquito olfaction molecule binding compound; (c) providing a test sample comprising the mosquito arrestin polypeptide and mosquito odorant receptor; (d) combining the mosquito olfaction molecule binding compound, the antibody, and the test sample in reaction conditions that allow a complex to form in the absence of the mosquito olfaction molecule binding compound., wherein the complex includes the antibody, mosquito arrestin and mosquito odorant receptor; and (e) determining whether the mosquito olfaction molecule binding compound decreases the formation of the complex, wherein a decrease indicates that the mosquito olfaction molecule binding compound is a compound that inhibits the binding of mosquito arrestin to mosquito odorant receptor. In certain embodiments, the mosquito odorant receptor further comprises a polypeptide having any of the following sequences: SEQ ID NO: 4, SEQ ID NO: 6, SEQ ID NO: 8, SEQ ID NO: 14, SEQ ID NO: 16, SEQ ID NO: 18, SEQ ID NO: 20, conservatively modified SEQ ID NO: 4, conservatively modified SEQ ID NO: 6, conservatively modified SEQ ID NO: 8, conservatively modified SEQ ID NO: 16, conservatively modified SEQ ID NO: 18, conservatively modified SEQ ID NO: 20 or conservatively modified SEQ ID NO: 14.

Various features and advantages of the invention will be apparent from the following detailed description and from the claims.

BRIEF DESCRIPTION OF THE DRAWINGS

FIG. 5 is a table of preferred codons used to deduce amino acid sequences from nucleotide sequences for *Anopheles gambiae*.

FIG. 6 is a table listing cDNA and polypeptide sequences with corresponding SEQ ID numbers.

FIG. 8 is the nucleotide sequence (SEQ ID NO: 22) of odorant receptor 6 isolated from *Anopheles gambiae*.

FIGS. 9A, 9B, 9C, 9D, 9E, 9F and 9G make up FIG. 9 which is the nucleotide sequence (SEQ ID NO: 23) of odorant receptor 7 isolated from *Anopheles gambiae*.

DETAILED DESCRIPTION OF THE INVENTION

Figure 1:
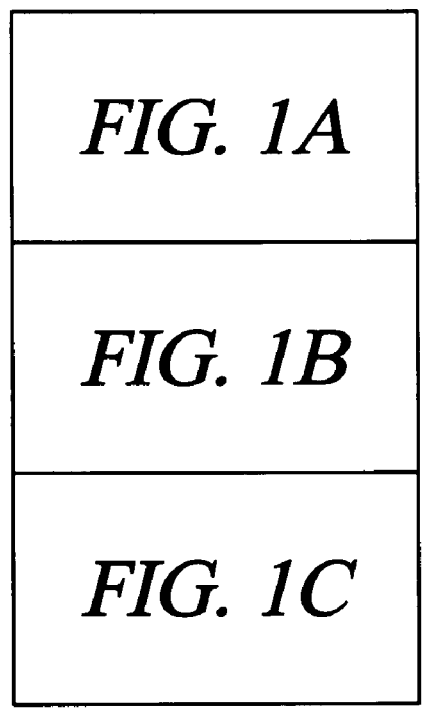
FIGS. 1A, 1B and 1C make up FIG. 1 which is the nucleotide sequence (SEQ ID NO: 9) of odorant receptor 1 isolated from *Anopheles gambiae*.
Figure 2:
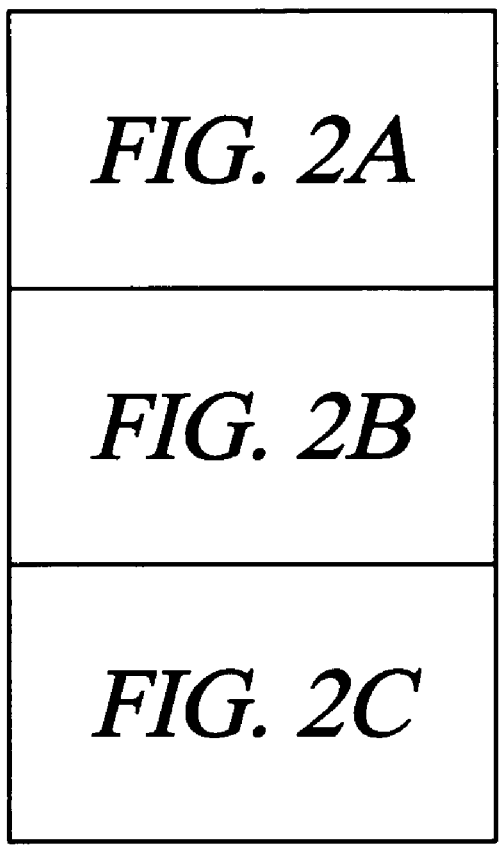
FIGS. 2A, 2B and 2C make up FIG. 2 which is the nucleotide sequence (SEQ ID NO: 10) of odorant receptor 2 isolated from *Anopheles gambiae*.
Figure 3:
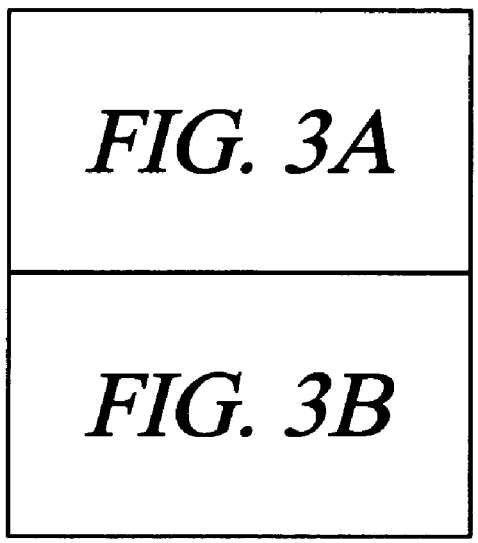
FIGS. 3A and 3B make up FIG. 3 which is the nucleotide sequence (SEQ ID NO: 11) of odorant receptor 3 isolated from *Anopheles gambiae*.
Figure 4:
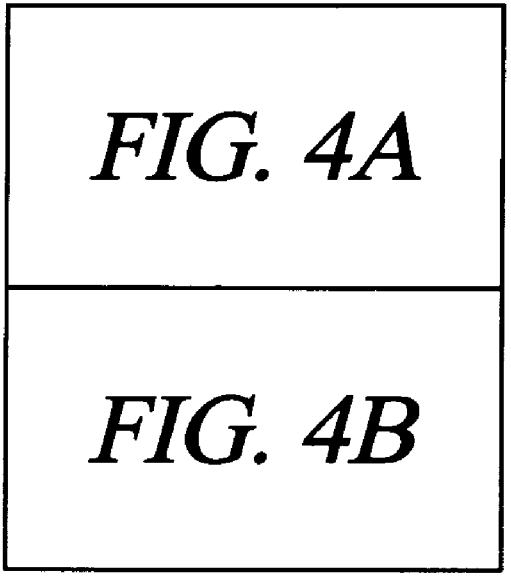
FIGS. 4A and 4B make up FIG. 4 which is the nucleotide sequence (SEQ ID NO: 12) of odorant receptor 4 isolated from *Anopheles gambiae*.
Figure 7:
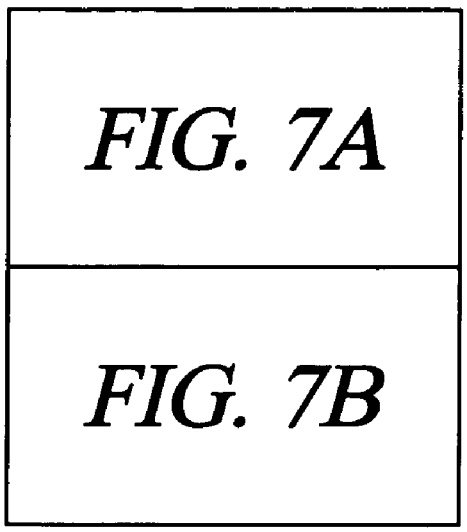
FIGS. 7A and 7B make up FIG. 7 which is the nucleotide sequence (SEQ ID NO: 21) of odorant receptor 5 isolated from *Anopheles gambiae*.

Arrestins interact with odorant receptors to cause changes in cellular function. Interruption of normal arrestin function will lead to over stimulation of the olfaction system. Consequently, substances that block the arrestin-odorant receptor interaction can interfere with a mosquito's ability to home in on sources of bloodmeal, such as humans. Screening for substances that modulate arrestin—odorant receptor interaction is therefore useful for identifying pest control agents and for treatment of malaria. The deduced amino acid sequence and arrestin contains several domains implicated in arrestin function. The motifs potention consensus Src homology 3 (SH3) binding sites. Cohen, et al., 1995, Cell, 80:237. Sequence comparisons with the DDBJ/EMBL/GenBank and SWISSPROT databases were performed using the GCG software. Devereux, et al., 1984, Nucleic Acids Res., 12:387–395. Protein alignment was also performed using the Clustal W software package. Thompson, et al., 1994, Nucleic Acids Res, 22:4673–4680. Additionally, arrestin has been submitted to the GenBank database with accession No. AY017417.

As used herein, "native conditions" means natural conditions as found within the ordinary conditions found within *Anopheles gambiae.*

As used herein, "stringent conditions" means the following: hybridization at 42° C. in the presence of 50% formamide; a first wash at 650° C. with about 2×SSC containing 1% SDS; followed by a second wash at 65° C. with 0.1×SSC. Salt concentrations and temperature may be modified. Such modifications may be found in Sambrook et al., 1989, Molecular Cloning: A Laboratory Manual (2nd Edition), Cold Spring Harbor Press, Cold Spring Harbor, N.Y. The hybridizing part of the nucleic acid is generally at least 15 nucleotides in length.

As used herein, "purified polypeptide" means a polypeptide that is substantially free from compounds normally associated with the polypeptide in the natural state. The absence of such compounds may be determined by detection of protein bands subsequent to SDS-PAGE. Purity may also be assessed in other ways known to those of ordinary skill in the art. The term, as defined herein, is not intended to exclude (1) synthetic or artificial combinations of the polypeptides with other compounds, (2) polypeptides having minor impurities which do not interfere with biological activity.

As used herein, "isolated polynucleotide" means a polynucleotide having a structure that is not identical to any naturally occurring nucleic acid or of any fragment of a naturally occurring genomic nucleic acid spanning more than three separate genes. Thus, the term includes (1) a nucleic acid incorporated into a vector or into the genomic DNA of a prokaryote or eukaryote in a manner such that the resulting molecule is not identical to any naturally occurring vector or genomic DNA; (2) a separate molecule of a cDNA, a genomic fragment, a fragment produced by polymerase chain reaction (PCR), or a restriction fragment; and (3) a recombinant nucleotide sequence that is part of a gene encoding a fusion protein. This definition of "isolated polynucleotide" supersedes and controls all other definitions known in the art.

As used herein, "hybridization probe" means nucleic acid that is labeled for detection, such as labeling with radiation. Hybridization probes are well known in the art.

As used herein, "culturing the cell" means providing culture conditions that are conducive to polypeptide expression. Such culturing conditions are well known in the art.

As used herein, "operably linked" means incorporated into a genetic construct so that expression control sequences effectively control expression of a gene of interest.

As used herein, "protein" means any peptide-linked chain of amino acids, regardless of length or post-translational modification, e.g., glycosylation or phosphorylation.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Preferably, the length of the compared sequences is at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

As used herein, "mosquito olfaction molecule" means a polypeptide that is involved in the modulation of the mosquito olfaction system. By way of illustration, and not limitation, mosquito olfaction molecules have the following characteristics: (1) G protein-coupled seven-transmembrane domain receptors, (2) sequence conservation regarding positions of a subset of introns and the length of the deduced protein, (3) they are selectively expressed in olfactory receptor neurons, and (4) they have highly conserved structural motifs. Odorant receptors 3, 4 and 5 are clustered tightly together within the *A. gambaie* genome. Odorant receptor 5 and odorant receptor 4 are separated by 310 bp while odorant receptor 4 and odorant receptor 3 are separated by 747 bp. An additional characteristic of odorant and taste receptor genes is the close chromosomal linkage. Such linkage has been demonstrated in the *D. melanogaster* and odorant receptor genes from *C. elegans* and mouse. Clyne, et al., 1999, Neuron, 22:327–338; Vosshall, et al., 1999, Cell, 96:725–736; Vosshall, et al., 2000, Cell, 102:147–159; Clyne, et al., 2000, Science, 287:1830–1834; Gao and Chess 1999, Genomics, 60:31–39; Troemel, et al., 1995, Cell, 83:207–218; Xie, et al., 2000, Genome, 11:1070–1080. Fox et. al., 2001, PNAS 98:14693–14697. This group of molecules includes odorant receptor 1 (SEQ ID NO: 4), odorant receptor 2 (SEQ ID NO: 6), odorant receptor 3 (SEQ ID NO: 8), odorant receptor 4 (SEQ ID NO: 14), odorant receptor 5 (SEQ ID NO: 16), odorant receptor 6 (SEQ ID NO: 18), odorant receptor 7 (SEQ ID NO: 20), arrestin 1 (SEQ ID NO: 2) and variants thereof as described herein.

As used herein, "odorant receptor" means any molecule performing the functional role of an odorant receptor, as described herein and in the scientific literature. Examples of odorant receptors included, but are not limited to, odorant receptor 1, odorant receptor 2, odorant receptor 3, odorant receptor 4, odorant receptor 5, odorant receptor 6, and odorant receptor 7.

As used herein, "mosquito olfaction molecule binding compound" means a compound that specifically binds to a mosquito olfaction molecule. Mosquito olfaction molecules additionally include polypeptides having the characteristics noted in the definition of the term.

As used herein, "mosquito olfaction molecule-specific antibody" means an antibody that binds to a mosquito olfaction molecule. The term includes polyclonal and monoclonal antibodies.

As used herein, "substantially pure protein" means a protein separated from components that naturally accompany it. Typically, the protein is substantially pure when it is at least 60%, by weight, free from the proteins and other naturally-occurring organic molecules with which it is naturally associated. In certain embodiments, the purity of the preparation is at least 75%, more preferably at least 90%, 95% and most preferably at least 99%, by weight. A substantially pure mosquito olfaction molecule protein can be obtained, for example, by extraction from a natural source, by expression of a recombinant nucleic acid encoding a mosquito olfaction molecule polypeptide, or by chemical synthesis. Purity can be measured by any appropriate method, e.g., column chromatography, polyacrylamide gel electrophoresis, or HPLC analysis. A chemically-synthesized protein or a recombinant protein produced in a cell type other than the cell type in which it naturally occurs is, by definition, substantially free from components that naturally accompany it. Accordingly, substantially pure proteins include those having sequences derived from eukaryotic organisms but synthesized in *E. coli* or other prokaryotes.

As used herein, "fragment", as applied to a polypeptide (e.g., arrestin 1 polypeptide), means at least about 10 amino acids, usually about 20 contiguous amino acids, preferably at least 40 contiguous amino acids, more preferably at least 50 amino acids, and most preferably at least about 60 to 80 or more contiguous amino acids in length. Such peptides can be generated by methods known to those skilled in the art, including proteolytic cleavage of the protein, de novo synthesis of the fragment, or genetic engineering.

As used herein, "test sample" means a sample that contains arrestin 1, or conservatively modified variant thereof, in combination with at least one of the following: odorant receptor 1, odorant receptor 2, odorant receptor 3, odorant receptor 5, odorant receptor 6, odorant receptor 7, odorant receptor 4, conservatively modified variants of the above, or other odorant receptors known in the art.

As used herein, "vector" means a replicable nucleic acid construct, e.g., a plasmid or viral nucleic acid. Preferably, expression is controlled by an expression control sequence.

As used herein, "conservatively modified" applies to both amino acid and nucleic acid sequences. Regarding nucleic acid sequences, conservatively modified refers to those nucleic acids which encode identical or conservatively modified variants of the amino acid sequences. Because of the degeneracy of the genetic code, a large number of functionally identical nucleic acids encode any given protein. For example, the codons GCA, GCC, GCG and GCU all encode the amino acid alanine. Thus, at every position where an alanine is specified by a codon, the codon can be altered to any of the corresponding codons described without altering the encoded polypeptide. Every nucleic acid sequence herein which encodes a polypeptide also describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for it's native substrate. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See also, Creighton (1984) Proteins W. H. Freeman and Company.

As used herein, "immunogenic fragment" means the fragment of a polypeptide that is capable of eliciting an immunogenic response.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Structure and Function

The genes disclosed herein have homology to corresponding arrestin and odorant receptor *Drosophila melanogaster* genes. Fox, et al., 2001, PNAS 98:14693–14697. The genes disclosed herein have the utility disclosed within this patent application.

A full-length *Anopheles gambiae* arrestin 1 cDNA has been cloned and sequenced. The arrestin 1 cDNA clone contains 1964 bp and includes a complete open reading frame that encodes a protein 383 amino acids in length, as seen in FIG. 1. The open reading frame from the methionine includes 383 amino acids, yielding a slightly basic polypeptide (PI=8.0) with a predicted molecular weight of 42.8 KD.

A full-length *Anopheles gambiae* odorant receptor 1 genomic DNA has been sequenced. The odorant receptor 1 genomic DNA contains 3895 bp and includes a deduced open reading frame that encodes a protein 394 amino acids in length.

A full-length *Anopheles gambiae* odorant receptor 2 genomic DNA has been sequenced. The odorant receptor 2 genomic DNA contains 4985 bp and includes a deduced open reading frame that encodes a protein 380 amino acids in length.

A full-length *Anopheles gambiae* odorant receptor 3 genomic DNA has been sequenced. The odorant receptor 3 genomic DNA contains 2083 bp and includes a deduced open reading frame that encodes a protein 411 amino acids in length.

A full-length *Anopheles gambiae* odorant receptor 4 genomic DNA has been sequenced. The odorant receptor 4 genomic DNA contains 2374 bp and includes a deduced open reading frame that encodes a protein 394 amino acids in length.

A full-length *Anopheles gambiae* odorant receptor 5 genomic DNA has been sequenced. The odorant receptor 5 genomic DNA contains 2272 bp and includes a deduced open reading frame that encodes a protein 391 amino acids in length.

A partial *Anopheles gambiae* odorant receptor 6 genomic DNA has been sequenced. The odorant receptor 6 genomic DNA contains 931 bp and includes a deduced open reading frame that encodes a protein 157 amino acids in length.

A full-length *Anopheles gambiae* odorant receptor 7 genomic DNA has been sequenced. The odorant receptor 7 genomic DNA contains 11,103 bp and includes a deduced open reading frame that encodes a protein 401 amino acids in length.

Expression Control Sequences and Vectors

The mosquito olfaction molecules of this invention can be used in a method to identify a mosquito olfaction molecule binding compound. If desired, the mosquito olfaction molecule binding compounds may be further tested for ability to inhibit binding of arrestin to an odorant receptor. Methods for this test are described herein. In certain embodiments, the DNA that encodes the arrestin 1 polypeptide ("ARR1 DNA") may be cloned into an expression vector, i.e., a vector wherein ARR1 DNA is operably linked to expression control sequences. The need for expression control sequences will vary according to the type of cell in which the ARR1 DNA is to be expressed. Generally, expression control sequences include a transcriptional promoter, enhancer, suitable mRNA ribosomal binding sites, and sequences that terminate transcription and translation. One of ordinary skill in the art can select proper expression control sequences. Standard methods can be used by one skilled in the art to construct expression vectors. See generally, Sambrook et al., 1989, Molecular Cloning: A Laboratory Manual (2nd Edition), Cold Spring Harbor Press, Cold Spring Harbor, N.Y. Vectors useful in this invention include, but are not limited to plasmid vectors and viral vectors.

All other nucleic acid sequences disclosed herein may also be operably linked to expression control sequences. The expression control sequences described above may be used. As mentioned above, methods known to those of ordinary skill in the art may be used to insert nucleic acid sequences into expression control sequences. Methods known to those of ordinary skill in the art may be used to introduce the nucleic acid and expression control sequence into eukaryotic and/or prokaryotic cells. An example of prokaryotic cells is BL21 (DE3)pLysS bacteria. An example of eukaryotic cells is Sf9.

In certain embodiments of the invention, ARR1 DNA is introduced into, and expressed in, a prokaryotic cell, e.g., BL21 (DE3)pLysS bacteria.

In certain embodiments of the invention, the ARR1 DNA is introduced into, and expressed in, a eukaryotic cell in vitro. Eukaryotic cells useful for expressing ARR1 DNA in vitro include, but are not limited to Sf9 cells. Transfection of the eukaryotic cell can be transient or stable.

Mosquito Olfaction Molecule-Specific Antibody

An animal is immunized with a mosquito olfaction molecule (e.g., arrestin 1 polypeptide). The animal produces antibodies to the mosquito olfaction molecule. The production and collection of the polyclonal antibodies was performed by Lampire Biological Laboratories, Inc. of Pipersville, Pa. 18947, using techniques known in the art.

Mosquito Olfaction Molecule Antibody Label

In some embodiments of the invention, the mosquito olfaction molecule-specific antibody includes a detectable label. Many detectable labels can be linked to, or incorporated into, an antibody of this invention. The following are examples of useful labels: radioactive, non-radioactive isotopic, fluorescent, chemiluminescent, paramagnetic, enzyme, or calorimetric.

Examples of useful enzyme labels include malate hydrogenase, staphylococcal dehydrogenase, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, and glucoamylase, acetylcholinesterase. Examples of useful radioisotopic labels include $^3H$, $^{131}I$, $^{125}I$, $^{32}P$, $^{35}S$, and $^{14}C$. Examples of useful fluorescent labels include fluorescein, rhodamine, phycoerythrin, phycocyanin, allophycocyanin, and fluorescamine. Examples of useful chemiluminescent label types include luminal, isoluminal, aromatic acridinium ester, imidazole, acridinium salt, oxalate ester, luciferin, luciferase, and aequorin.

Antibody labels can be coupled to, or incorporated into antibodies by use of common techniques known to those of ordinary skill in the art. Typical techniques are described by Kennedy et al., 1976, Clin. Chim. Acta, 70:1–31; and Schurs et al., 1977, Clin. Chim. Acta, 81: 1–40. Useful chemical coupling methods include those that use glutaraldehyde, perioddate, dimaleimide and m-maleimido-benzyl-N-hydroxy-succinimide ester.

Screening Assays

The present invention provides, in part, a screen for mosquito olfaction molecule binding compounds with the ability to interrupt the interaction of arrestin with an odorant receptor. Identifying that a test agent will bind a mosquito olfaction molecule is one part. Once a test agent has demonstrated its ability to bind a mosquito olfaction molecule, it is properly called a mosquito olfaction molecule binding compound. Since it is possible for a mosquito olfaction molecule binding compound to bind without necessarily interrupting the arrestin-odorant receptor interaction, it is proper to further assay in order to determine that the interaction is disrupted. The ability of the mosquito olfaction molecule binding compound to interrupt the arrestin-odorant receptor interaction may be assayed.

In certain embodiments, a test agent is identified as a mosquito olfaction molecule binding compound by the following method. One of the mosquito olfaction molecules is immobilized (e.g., arrestin 1). Polypeptides can be immobilized using methods known in the art. Such methods include the use of Affigel (Biorad) or activated agarose or sepharose to which significant amounts of polypeptides can be directly coupled. The immobilized polypeptide (e.g., arrestin 1) is contacted with the test agent. Unbound test agent can be removed by washing with binding buffer. Then, the bound test agent is eluted by a salt gradient. The material that is bound to the immobilized polypeptide may be purified by SDS-PAGE. Other methods known by one of ordinary skill in the art for identifying an interaction between two proteins include affinity purification, co-immunoprecipitation, and far-western blotting.

In certain embodiments, the following method is used to screen for substances capable of interrupting arrestin-odorant receptor interaction. The following method of detecting protein-protein interaction will also provide information regarding the lack of protein-protein interactions. The two-hybrid method is a well known genetic assay used to detect protein-protein interactions in vivo. See, e.g., Bartel et al., 1993, In Cellular Interactions in Development: A Practical Approach, Oxford University Press, Oxford, pp. 153–179; Chien et al., 1991, Proc. Natl. Acad. Sci. USA, 88:9578–9582; Fields et al., 1989, Nature, 340:245–247; Fritz et al., 1992, Curr. Biol., 2:403–405; Guarente, L., 1993, Proc. Natl. Acad. Sci. USA, 90:1639–1641. There are multiple combinations available between arrestin and the seven odorant receptors. A GAL4 binding domain is linked to an arrestin fragment (e.g., arrestin 1 polypeptide) and a GAL4 transactivation domain is linked to an odorant receptor fragment (e.g., odorant receptor 1 polypeptide). A GAL4 binding site is linked to a reporter gene such as lacZ. All three elements are contacted in the presence and absence of a mosquito olfaction molecule binding compound. The level of expression of the reporter gene is monitored. A decrease in the level of expression of lacZ means that the mosquito olfaction molecule binding compound interrupts the interaction of arrestin with the odorant receptor.

In an alternate embodiment, the following is a method that will identify whether a mosquito olfaction molecule binding compound will interrupt the interaction between arrestin and an odorant receptor. The following method of co-immunoprecipitation may make use of the available panel of antibodies to any arrestin or odorant receptor. Since this method makes use of antibodies that demonstrate the ability to immunoprecipitate the mosquito olfaction molecule and other proteins to which it is bound, the ability of a mosquito olfaction molecule binding compound to inhibit the interaction of the mosquito olfaction molecule will serve as the measure of the compound's interruption ability.

Also disclosed herein is a method of modulating arrestin 1 biological activity. In certain embodiments, the method comprises administering an arrestin 1 biological activity-modulating amount of a mosquito olfaction molecule binding compound. Upon administration, arrestin 1 is contacted with the mosquito olfaction molecule binding compound. Such contact results in modulating arrestin 1 biological activity. The mosquito olfaction molecule binding compound may be administered as an aerosol, solid, or liquid, such that delivery occurs through contact with the body of the target subject. For example, administration may occur by absorption through the exterior surfaces of the target subject, ie. mosquitoes, or by intake through other apertures of the target subject [proboscis (or other feeding aperture), or spiracles (or other respiratory apertures]. An activity-modulating amount of mosquito olfaction molecule binding compound is an amount that is sufficient to prohibit at least about 50% of the arrestin 1 (SEQ ID NO: 2) molecules from interacting with any odorant receptors.

All citations and references described in this patent application are hereby incorporated herein by reference, in their entirety. Also incorporated in this specification are the exhibits filed herewith. The present invention is further illustrated by the following specific examples. The examples are provided for illustration only and are not to be construed as limiting the scope or content of the invention in any way.

EXAMPLE 1

Protein Expression

A cDNA encoding arrestin 1 is subcloned into the pBlueScript II (KS) vector (Novagen, Madison, Wis.) at the BamHI/NdeI restriction sites for DNA sequencing. The cDNA encoding arrestin 1 is subsequently subcloned into the bacterial expression plasmid pET15b (Novagen, Madison, Wis.). The bacterial expression plasmid containing the arrestin 1 cDNA is transformed into BL21 (DE3)pLysS bacteria (Novagen, Madison, Wis.) for high levels of arrestin 1 expression. Methods are known in the art for isolating the expressed protein.

Expression of other nucleic acids disclosed herein is achieved by using the above-referenced method. Once the odorant receptor is in protein form, it may be used as described within this application.

EXAMPLE 2

Mosquito Olfaction Molecule Specific Antibody

The cDNA encoding arrestin 1 is subcloned into the bacterial expression plasmid pET15b (Novagen, Madison, Wis.). The vector is transformed into BL21 (DE3)pLysS bacteria (Novagen, Madison, Wis.) for high levels of arrestin 1 expression. Rapid purification is performed using His-Bind affinity Resin (Novagen, Madison, Wis.). Native recombinant arrestin 1 is then denatured using gel purification on SDS-polyacrylamide gel electrophoresis followed by staining with 0.05% Coomassie Brilliant Blue (Sigma-Aldrich, St. Louis, Mo.). Polyclonal antibodies were generated in rabbits by Lampire Biological Laboratories, Inc. of Pipersville, Pa. 18947. Polyclonal antibodies may be generated for any of the odorant receptors disclosed herein.

EXAMPLE 3

Identification of a Mosquito Olfaction Molecule Binding Compound

Arrestin 1 polypeptide is expressed in and purified from BL21 (DE3)pLysS bacteria (Novagen, Madison, Wis.). Arrestin 1 is incubated with a test agent in Phosphate Buffered Saline (pH 7.5), 0.1% Tween-20, and 0.1% broad spectrum protease inhibitors for 90 minutes at 4° C. Anti-arrestin 1 polyclonal sera is added to the reaction at a dilution of 1:2000 and incubated for an additional 60 minutes. The complexes, consisting of either polypeptide-antibody or test agent-polypeptide-antibody are isolated by the addition of $1 \times 10^7$ Dynalbeads M280 (sheep anti-Rabbit IgG) followed by incubation at the same temperature for an additional 60 minutes. Isolation of the complexes is completed by using the DYNAL Magnetic Particle Concentrator (Dynal Inc., Lake Success, N.Y.). The complexes are washed three times with broad spectrum protease inhibitors. Content of the complexes is assayed by SDS-PAGE followed by silver staining and western blotting. Common methods are known by those of ordinary skill in the art for silver staining and western blotting. See generally, Sambrook et al., 2001, Molecular Cloning: A Laboratory Manual (3rd Edition), Cold Spring Harbor Press, Cold Spring Harbor, N.Y. Obviously, the presence of the test agent, polypeptide, and antibody indicates that the test agent binds to the polypeptide.

EXAMPLE 4

Identification of a Compound that Inhibits Binding of Arrestin to an Odorant Receptor Arrestin 1 polypeptide and odorant receptor 1 polypeptide are expressed in and purified from BL21 (DE3)pLysS bacteria (Novagen, Madison, Wis.). Arrestin 1 polypeptide and odorant receptor 1 polypeptide are incubated with a mosquito olfaction molecule binding compound in Phosphate Buffered Saline (pH 7.5), 0.1% Tween-20, and 0.1% broad spectrum protease inhibitors for 90 minutes at 4° C. Anti-arrestin 1 polyclonal sera is added to the reaction at a dilution of 1:2000 and incubated for an additional 60 minutes. The complexes, consisting of either antibody-arrestin 1-odorant receptor 1 or antibody-arrestin 1, are isolated by the addition of 1×10⁷ Dynalbeads M280 (sheep anti-Rabbit IgG) followed by incubation at the same temperature for an additional 60 minutes (Dynal Inc., Lake Success, N.Y.). Once the isolation of the complexes is completed by using the DYNAL Magnetic Particle Concentrator, (Dynal Inc., Lake Success, N.Y.), the complexes are washed three times with broad spectrum protease inhibitors. The content of the complexes is assayed by SDS-PAGE followed by silver staining and western blotting. Common methods are known by those of ordinary skill in the art for silver staining and western blotting. See generally, Sambrook et al., 2001, Molecular Cloning: A Laboratory Manual (3rd Edition), Cold Spring Harbor Press, Cold Spring Harbor, N.Y.

EXAMPLE 5

Far Western Blotting to Analyze Components of a Protein Mixture

The protein sample is fractionated on an SDS-PAGE gel. After electrophoresis at a voltage and time that is known in the art, the proteins are transferred from the gels onto a solid support membrane by electroblotting. Transferred membranes may be stained with Ponceau S to facilitate location and identification of specific proteins. Nonspecific sites on the membranes are blocked with standard blocking reagents, and the membranes are then incubated with a radiolabeled non-antibody protein probe. After washing, proteins that bind to the probe are detected by autoradiography.

The content of the solutions used within this protocol are disclosed in Wiley's Current Protocols in Cell Biology.

The protein sample to be analyzed is resuspended in 1×SDS sample buffer. Approximately 50 to 100 ug can be loaded in each lane of the gel. The samples are separated with SDS-PAGE. The proteins are transferred to nitrocellulose by electroblotting.

After transfer, stain the membrane for 5 min in ~100 ml freshly diluted 1× Ponceau S staining solution. The membrane is then destained by washing it in several changes of deionized water until the proteins are clearly visible. Continue to destain for an additional 5 min in water until the red staining fades.

The membrane is then blocked for 2 hr in 200 ml blocking buffer I at room temperature with gentle agitation. Incubate the membrane in 200 ml of blocking buffer II for 2 hours and rinse the membrane briefly in 100 ml of 1×PBS.

Prior to probing, the membrane is preincubated for 10 min in 50 ml of 1× probe dilution buffer without the probe at room temperature. The probe is added to the membrane and incubated for 2 hours at room temperature. The membrane is washed with 200 ml 1×PBS for 5 min, room temperature. Repeat the wash step three additional times. Air dry the filter and expose to x-ray film with intensifying screen. An overnight exposure is typically sufficient.

What is claimed is:

1. A purified polypeptide comprising the amino acid sequence of SEQ ID NO: 2.

2. A purified polypeptide comprising a fragment of at least 40 consecutive amino acids of SEQ ID NO:2.

* * * * *